(12) United States Patent
Baik et al.

(10) Patent No.: US 8,044,062 B2
(45) Date of Patent: Oct. 25, 2011

(54) SUBSTITUTED PYRIDO[2,3-D]PYRIMIDIN-7(8H)-ONE INHIBITORS OF PHOSPATIDYLINOSITOL 3-KINASE ALPHA

(75) Inventors: Tae-Gon Baik, Foster City, CA (US); Chris A. Buhr, Redwood City, CA (US); Katherine Lara, San Mateo, CA (US); Sunghoon Ma, Foster City, CA (US); Morrison Mac, San Francisco, CA (US); John M. Nuss, Danville, CA (US); Longcheng Wang, Palo Alto, CA (US); Yong Wang, Foster City, CA (US); Bryan K. S. Yeung, Chromos (SG)

(73) Assignee: Exelixis, Inc., South San Francisco, CA (US)

( * ) Notice: Subject to any disclaimer, the term of this patent is extended or adjusted under 35 U.S.C. 154(b) by 834 days.

(21) Appl. No.: 11/988,848

(22) PCT Filed: Oct. 9, 2006

(86) PCT No.: PCT/US2006/039734
§ 371 (c)(1),
(2), (4) Date: Jan. 15, 2008

(87) PCT Pub. No.: WO2007/044813
PCT Pub. Date: Apr. 19, 2007

(65) Prior Publication Data
US 2009/0270430 A1    Oct. 29, 2009

Related U.S. Application Data

(60) Provisional application No. 60/724,571, filed on Oct. 7, 2005, provisional application No. 60/743,719, filed on Mar. 23, 2006.

(51) Int. Cl.
C07D 471/04        (2006.01)
A61K 31/519       (2006.01)
A61P 35/00         (2006.01)
(52) U.S. Cl. .................. 514/264.11; 544/279
(58) Field of Classification Search ............. 544/279; 514/264.11
See application file for complete search history.

(56) References Cited

U.S. PATENT DOCUMENTS

| | | | |
|---|---|---|---|
| 2004/0009993 A1 | 1/2004 | Angiolini et al. | |
| 2005/0182078 A1 | 8/2005 | Barvian et al. | |
| 2010/0227861 A1* | 9/2010 | Bearss et al. | 514/233.2 |

FOREIGN PATENT DOCUMENTS

| | | |
|---|---|---|
| EP | 1 277 738 A1 | 1/2003 |
| EP | 1 364 950 A1 | 11/2003 |
| JP | 2004-083587 | 3/2004 |
| WO | WO 96/34867 | 11/1996 |
| WO | WO 98/33798 | 8/1998 |
| WO | WO 01/55148 A1 | 8/2001 |
| WO | WO 01/70741 A1 | 9/2001 |
| WO | WO 03/088972 A1 | 10/2003 |
| WO | WO 03/093290 A2 | 11/2003 |
| WO | WO 2005105801 | * 5/2004 |
| WO | WO 2005105097 | * 6/2004 |
| WO | WO 2004/063195 A1 | 7/2004 |
| WO | WO 2004/089930 A1 | 10/2004 |
| WO | WO 2005/040337 A2 | 5/2005 |
| WO | WO 2005/082903 A1 | 9/2005 |
| WO | WO 2005/105801 A1 | 11/2005 |
| WO | WO 2006/065703 A1 | 6/2006 |

OTHER PUBLICATIONS

Griesser, Chapter 8, The Importance of Solvates (pp. 211-230), Polymorphism: In the Pharmaceutical Industry, Hilfiker, 2006.*
Wikipedia, Acyl, last modified Mar. 11, 2010.*
IUPAC, http://www.iupac.org/goldbook/A00123.pdf, downloaded Oct. 29, 2010.*
Hawley's Condensed Chem. Dict., 14th Ed., 2002.*
Hackh's Chem. Dict., 3rd Ed., 1944, p. 18WO 2005106097.*
Angiolini, M., et al., "Solid-phase synthesis of pyrido[2,3-d]pyrimidin-7-ones," Tetrahedron Letters, (2005), vol. 46, pp. 8749-8752.
Barvian, M., et al., "Pyrido[2,3-d]pyrimidin-7-one inhibitors of cyclin-dependent kinases," J. Med. Chem., (2000) vol. 43, pp. 4606-4616.
Boschelli, D.H., et al., "Synthesis and tyrosine kinase inhibitory activity of a series of 2-amino-8H-pyrido[2,3-d]pyrimidines: identification of potent, selective platelet-derived growth factor receptor tyrosine kinase inhibitors," J. Med. Chem., (1998) vol. 41, pp. 4365-4377.
Hamby, J.M., et al., "Structure-activity relationships for a novel series of pyrido[2,3-*d*]pyrimidine tyrosine kinase inhibitors," J. Med. Chem., (1997) vol. 40, pp. 2296-2303.
Klutchko, S.R., et al., "2-Substituted aminopyrido[2,3-*d*]pyrimidin-7(8H)-ones. Structure-activity relationships against selected tyrosine kinases and in vitro and in vivo anticancer activity," J. Med Chem., (1998), vol. 41, pp. 3276-3292.
Toogood, P.L. et al., "Discovery of a potent and selective inhibitor of cyclin-dependent kinase 4/6," J. Med. Chem., (2005) vol. 48, pp. 2388-2406.

(Continued)

Primary Examiner — James O Wilson
Assistant Examiner — Cecilia M Jaisle
(74) Attorney, Agent, or Firm — Honigman Miller Schwartz & Cohn LLP; Heidi M. Berven; Jonathan P. O'Brien

(57) ABSTRACT

The invention is directed to Compounds of Formula I:

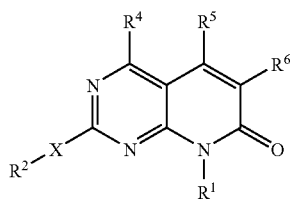

and pharmaceutically acceptable salts or solvates thereof, as well as methods of making and using the compounds.

37 Claims, No Drawings

OTHER PUBLICATIONS

Trumpp-Kallmeyer, S., et al., "Development of a binding model to protein tyrosine kinases for substituted pyrido[2,3-d]pyrimidine inhibitors," J. Med. Chem., (1998) vol. 41, pp. 1752-1763.

Database Registry, CAS registration No. 400881-06-3, (date of publication Mar. 14, 2002), Chemical Abstracts Service, STN North America, Columbus, Ohio, www.cas.org/stn.html.

Database Registry, CAS registration No. 400878-58-2, (date of publication Mar. 14, 2002), Chemical Abstracts Service, STN North America, Columbus, Ohio, www.cas.org/stn.html.

Database Registry, CAS registration No. 374910-33-5 (date of publication Dec. 13, 2001), Chemical Abstracts Service, STN North America, Columbus, Ohio, www.cas.org/stn.html.

Database Registry, CAS registration No. 294874-94-5 (date of publication Oct. 12, 2000), Chemical Abstracts Service, STN North America, Columbus, Ohio, www.cas.org/stn.html.

Database Registry, CAS registration No. 405295-77-4 (date of publication Apr. 16, 2002), Chemical Abstracts Service, STN North America, Columbus, Ohio, www.cas.org/stn.html.

* cited by examiner

SUBSTITUTED PYRIDO[2,3-D]PYRIMIDIN-7(8H)-ONE INHIBITORS OF PHOSPATIDYLINOSITOL 3-KINASE ALPHA

CROSS REFERENCE TO RELATED APPLICATIONS

The Applicants claim priority under 35 U.S.C. 119(e) to Provisional Applications No. 60/724,571 filed on Oct. 7, 2005 and No. 60/743,719 filed on Mar. 23, 2006, the disclosures of which are incorporated herein by reference in its entirety.

BACKGROUND OF THE INVENTION

1. Field of the Invention

This invention relates to the field of protein kinases and inhibitors thereof. In particular, the invention relates to inhibitors of phosphatidylinositol 3-kinase (PI3K) signaling pathways, and methods of their use.

2. Summary of the Related Art

The connection between abnormal protein phosphorylation and the cause or consequence of diseases has been known for over 20 years. Accordingly, protein kinases have become a very important group of drug targets. See Cohen, Nature, 1:309-315 (2002). Various protein kinase inhibitors have been used clinically in the treatment of a wide variety of diseases, such as cancer and chronic inflammatory diseases, including diabetes and stroke. See Cohen, Eur. J. Biochem., 268:5001-5010 (2001).

The protein kinases are a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al. Pharmaceutical Research, 17(11):1345-1353 (2000). Viral infections and the conditions related thereto have also been associated with the regulation of protein kinases. Park et al. Cell 101 (7), 777-787 (2000).

Phosphatidylinositol 3-kinase (PI3Kα), a dual specificity protein kinase, is composed of an 85 kDa regulatory subunit and a 110 kDa catalytic subunit. The protein encoded by this gene represents the catalytic subunit, which uses ATP to phosphorylate PtdIns, PtdIns4P and PtdIns(4,5)P2. PTEN, a tumor suppressor which inhibits cell growth through multiple mechanisms, can dephosphorylate PIP3, the major product of PIK3CA. PIP3, in turn, is required for translocation of protein kinase B (AKT1, PKB) to the cell membrane, where it is phosphorylated and activated by upstream kinases. The effect of PTEN on cell death is mediated through the PIK3CA/AKT1 pathway.

PI3Kα has been implicated in the control of cytoskeletal reorganization, apoptosis, vesicular trafficking, proliferation and differentiation processes. Increased copy number and expression of PIK3CA is associated with a number of malignancies such as ovarian cancer (Campbell et al., *Cancer Res* 2004, 64, 7678-7681; Levine et al., *Clin Cancer Res* 2005, 11, 2875-2878; Wang et al., *Hum Mutat* 2005, 25, 322; Lee et al., *Gynecol Oncol* 2005, 97, 26-34), cervical cancer, breast cancer (Bachman, et al. *Cancer Biol Ther* 2004, 3, 772-775; Levine, et al., supra; Li et al., *Breast Cancer Res Treat* 2006, 96, 91-95; Saal et al., *Cancer Res* 2005, 65, 2554-2559; Samuels and Velculescu, *Cell Cycle* 2004, 3, 1221-1224), colorectal cancer (Samuels, et al. *Science* 2004, 304, 554; Velho et al. *Eur J Cancer* 2005, 41, 1649-1654), endometrial cancer (Oda et al. *Cancer Res.* 2005, 65, 10669-10673), gastric carcinomas (Byun et al., *Int J Cancer* 2003, 104, 318-327; Li et al., supra; Velho et al., supra; Lee et al., *Oncogene* 2005, 24, 1477-1480), hepatocellular carcinoma (Lee et al., id.), small and non-small cell lung cancer (Tang et al., *Lung Cancer* 2006, 51, 181-191; Massion et al., *Am J Respir Crit. Care Med* 2004, 170, 1088-1094), thyroid carcinoma (Wu et al., *J Clin Endocrinol Metab* 2005, 90, 4688-4693), acute myelogenous leukemia (AML) (Sujobert et al., *Blood* 1997, 106, 1063-1066), chronic myelogenous leukemia (CML) (Hickey and Cotter *J Biol Chem* 2006, 281, 2441-2450), and glioblastomas (Hartmann et al. *Acta Neuropathol* (Berl) 2005, 109, 639-642; Samuels et al., supra).

In view of the important role of PI3Kα in biological processes and disease states, inhibitors of this protein kinase are desirable.

SUMMARY OF THE INVENTION

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

The invention provides compounds that inhibit, regulate, and/or modulate PI3K that are useful in the treatment of hyperproliferative diseases, such as cancer, in humans. This invention also provides methods of making the compound, methods of using such compounds in the treatment of hyperproliferative diseases in humans and to pharmaceutical compositions containing such compounds.

A first aspect of the invention provides a compound of Formula I:

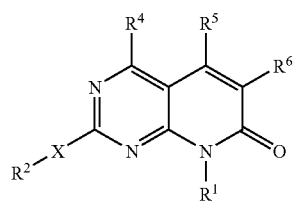

or a pharmaceutically acceptable salt or solvate thereof, wherein $R^1$ is hydrogen, optionally substituted alkyl, optionally substituted cycloalkyl, optionally substituted cycloalkylalkyl, optionally substituted aryl, optionally substituted arylalkyl, optionally substituted heterocycloalkyl, optionally substituted heterocycloalkylalkyl, optionally substituted heteroaryl or optionally substituted heteroarylalkyl;

$R^2$ is hydrogen or alkyl where the alkyl is optionally substituted with 1, 2, 3, 4, or 5 $R^8$ groups;

X is —$NR^3$—;

$R^3$ hydrogen;

$R^4$ is optionally substituted alkyl;

$R^5$ is hydrogen; and $R^6$ is phenyl, acyl, or heteroaryl wherein the phenyl and heteroaryl are optionally substituted with 1, 2, 3, 4, or 5 $R^9$ groups;

each $R^8$, when present, is independently hydroxy, halo, alkoxy, haloalkoxy, amino, alkylamino, dialkylaminoalkyl, or alkoxyalkylamino; and each $R^9$, when present, is independently halo, alkyl, haloalkyl, alkoxy, haloalkoxy, cyano, amino, alkylamino, dialkylamino, alkoxyalkyl, carboxyalkyl, alkoxycarbonyl, aminoalkyl, cycloalkyl, aryl, arylalkyl, aryloxy, heterocycloalkyl, or heteroaryl and where the cycloalkyl, aryl, heterocycloalkyl, and heteroaryl, each either alone or as part of another group within $R^9$, are independently optionally substituted with 1, 2, 3, or 4 groups selected from halo, alkyl, haloalkyl, hydroxy, alkoxy, haloalkxy, amino, alkylamino, and dialkylamino.

A second aspect of the invention provides a compound of Formula II:

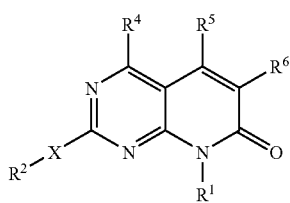

II or a pharmaceutically acceptable salt or solvate thereof, wherein $R^1$ is hydrogen, optionally substituted alkyl, optionally substituted $C_3$-$C_7$ cycloalkyl, optionally substituted aryl, optionally substituted arylalkyl, optionally substituted heterocycloalkyl, optionally substituted heterocycloalkylalkyl, optionally substituted heteroaryl or optionally substituted heteroarylalkyl;

X is S, $SO_2$, or —$NR^3$—;

$R^2$ is hydrogen, haloalkyl, optionally substituted alkyl, optionally substituted $C_3$-$C_7$ cycloalkyl, optionally substituted aryl, optionally substituted arylalkyl, optionally substituted heterocycloalkyl, optionally substituted heterocycloalkylalkyl, optionally substituted heterocycloalkylaryl- or optionally substituted heteroaryl; $R^2$ is optionally further substituted with one or more $R^8$ groups;

$R^3$, $R^{3a}$, and $R^{3b}$ are independently hydrogen, optionally substituted alkyl, optionally substituted $C_3$-$C_7$ cycloalkyl, optionally substituted aryl, optionally substituted heterocycloalkyl or optionally substituted heteroaryl;

$R^4$ is hydrogen, halo, haloalkyl, haloalkoxy, —$NR^{3a}$—, optionally substituted alkyl, optionally substituted $C_1$-$C_6$ alkoxy, optionally substituted $C_1$-$C_6$ alkoxyalkyl, optionally substituted aminoalkyl, optionally substituted $C_3$-$C_7$ cycloalkyl, optionally substituted aryl, or optionally substituted heteroaryl;

$R^5$ is hydrogen, halo, haloalkyl, haloalkoxy, optionally substituted $C_1$-$C_6$ alkyl, optionally substituted $C_1$-$C_6$ alkoxy, optionally substituted $C_1$-$C_6$ alkoxyalkyl, optionally substituted aminoalkyl, optionally substituted $C_3$-$C_7$ cycloalkyl, optionally substituted aryl, optionally substituted aryl $C_1$-$C_6$ alkyl or optionally substituted heteroaryl; and $R^6$ is hydrogen, halo, haloalkyl, haloalkoxy, —$NR^{3b}$—, optionally substituted $C_1$-$C_6$ alkyl, optionally substituted $C_1$-$C_6$ alkoxy, optionally substituted $C_1$-$C_6$ alkoxyalkyl, optionally substituted acyl, optionally substituted aminoalkyl, optionally substituted $C_3$-$C_7$ cycloalkyl, optionally substituted aryl, optionally substituted arylalkyl, optionally substituted heterocycloalkyl, or optionally substituted heteroaryl; substitutable $R^6$ groups are optionally further substituted with 1, 2, 3, 4, or 5 $R^9$ groups;

each $R^8$, when present, is independently hydroxy, halo, haloalkyl, haloalkoxy, optionally substituted alkyl, optionally substituted $C_1$-$C_6$ alkoxy, optionally substituted $C_1$-$C_6$ alkoxyalkyl, optionally substituted $C_1$-$C_6$ alkoxyalkylaminoalkyl, $C_1$-$C_6$ alkylcarboxyheterocycloalkyl, oxy $C_1$-$C_6$alkylheterocycloalkyl, optionally substituted aminoalkyl, optionally substituted $C_3$-$C_7$ cycloalkyl, optionally substituted aryl, optionally substituted aryl $C_1$-$C_6$ alkyl, optionally substituted heterocycloalkyl, optionally substituted heterocycloalkylalkyl, optionally substituted heteroaryl or optionally substituted heteroarylalkyl;

each $R^9$, when present, is independently halo, haloalkyl, haloalkoxy, optionally substituted $C_1$-$C_6$ alkyl, optionally substituted $C_1$-$C_6$ alkoxy, optionally substituted $C_1$-$C_6$ alkoxyalkyl, optionally substituted $C_1$-$C_6$ carboxyalkyl, optionally substituted alkoxycarbonyl, optionally substituted aminoalkyl, optionally substituted $C_3$-$C_7$ cycloalkyl, optionally substituted aryl, optionally substituted aryl $C_1$-$C_6$ alkyl, optionally substituted aryloxy, optionally substituted heterocycloalkyl, or optionally substituted heteroaryl.

In a third aspect, the invention is directed to a pharmaceutical composition which comprises a compound of Formula I or a pharmaceutically acceptable salt thereof and a pharmaceutically acceptable carrier, excipient, or diluent.

In a fourth aspect, the invention comprises a method of inhibiting PI3K, comprising contacting a cell with a compound of Formula I or II or a pharmaceutically acceptable salt or solvate thereof, or with a pharmaceutical composition comprising a therapeutically effective amount of a compound of Formula I or II and a pharmaceutically acceptable carrier, excipient, or diluent.

In a fifth aspect of the invention is a method of inhibiting the in vivo activity of PI3Kα, the method comprising administering to a patient an effective PI3Kα-inhibiting-inhibiting amount of a compound of Formula I or II, or a pharmaceutically acceptable salt, solvate, or a pharmaceutical composition thereof.

In a sixth aspect, the Invention provides a method for treating a disease, disorder, or syndrome which method comprises administering to a patient a therapeutically effective amount of a compound of Formula I or II or a pharmaceutically acceptable salt or solvate thereof, or a pharmaceutical composition comprising a therapeutically effective amount of a compound of Formula I or II and a pharmaceutically acceptable carrier, excipient, or diluent.

A seventh aspect of the invention is directed to a process of preparing a compound of Formula I, comprising:
(a) reacting an intermediate of formula 7(a):

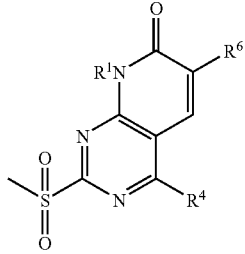

7(a)

where $R^6$ is phenyl or heteroaryl each optionally substituted with 1, 2, 3, 4, or 5 $R^9$ groups (as defined in the Summary of the Invention) and $R^1$ and $R^4$ are as defined in the Summary of the Invention; with an intermediate of formula $R^2NH_2$ (where $R^2$ is as defined in the Summary of the Invention) to yield a Compound of Formula I(a):

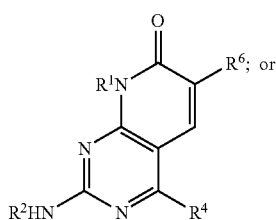

I(a)

(b) reacting an intermediate of formula 18:

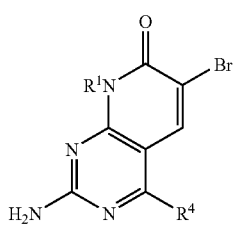

18 where $R^1$ and $R^4$ are as defined in the Summary of the Invention; with tributyl-1-ethylvinyltin or with an intermediate of formula $R^6B(OH)_2$ where $R^6$ is phenyl or heteroaryl each optionally substituted with 1, 2, 3, 4, or 5 $R^9$ groups (as defined in the Summary of the Invention) to yield, respectively, a Compound of Formula I(a) or I(b):

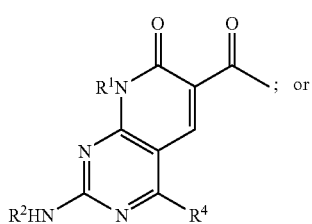

I(b)

(c) reacting an intermediate of formula 25(a):

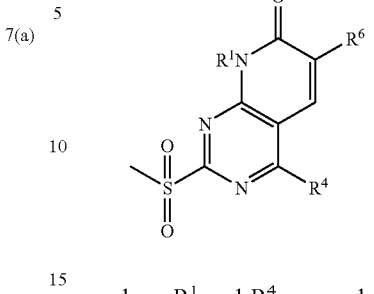

25(a)

where $R^1$ and $R^4$ are as defined in the Summary of the Invention; with an intermediate of $R^2NH_2$ (where $R^2$ is as defined in the Summary of the Invention) to yield a Compound of Formula I(a); and
(d) optionally further resolving individual isomers; and
(e) optionally further modifying one of the $R^1$, $R^2$, $R^4$, and $R^6$ groups.

DETAILED DESCRIPTION OF THE INVENTION

Abbreviations and Definitions

The following abbreviations and terms have the indicated meanings throughout:

| Abbreviation | Meaning |
|---|---|
| Ac | acetyl |
| br | broad |
| ° C. | degrees Celsius |
| c- | cyclo |
| CBZ | CarboBenZoxy = benzyloxycarbonyl |
| d | doublet |
| dd | doublet of doublet |
| dt | doublet of triplet |
| DCM | dichloromethane |
| DME | 1,2-dimethoxyethane |
| DMF | N,N-dimethylformamide |
| DMSO | dimethyl sulfoxide |
| dppf | 1,1'-bis(diphenylphosphano)ferrocene |
| EI | Electron Impact ionization |
| g | gram(s) |
| h or hr | hour(s) |
| HPLC | high pressure liquid chromatography |
| L | liter(s) |
| M | molar or molarity |
| m | Multiplet |
| mg | milligram(s) |
| MHz | megahertz (frequency) |
| Min | minute(s) |
| mL | milliliter(s) |
| μL | microliter(s) |
| μM | Micromole(s) or micromolar |
| mM | Millimolar |
| mmol | millimole(s) |
| mol | mole(s) |
| MS | mass spectral analysis |
| N | normal or normality |
| nM | Nanomolar |
| NMR | nuclear magnetic resonance spectroscopy |
| q | Quartet |
| RT | Room temperature |
| s | Singlet |
| t or tr | Triplet |
| TFA | trifluoroacetic acid |
| THF | tetrahydrofuran |
| TLC | thin layer chromatography |

The symbol "—" means a single bond, "=" means a double bond, "≡" means a triple bond, "- - - -" means a single or double bond. The symbol "⌇⌇⌇" refers to a group on a double-bond as occupying either position on the terminus of a double bond to which the symbol is attached; that is, the geometry, E- or Z-, of the double bond is ambiguous. When a group is depicted removed from its parent formula, the "〜" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

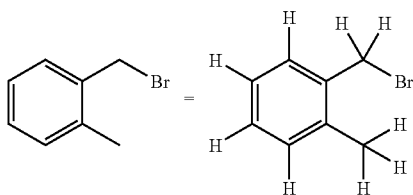

If a group "R" is depicted as "floating" on a ring system, as for example in the formula:

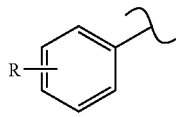

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

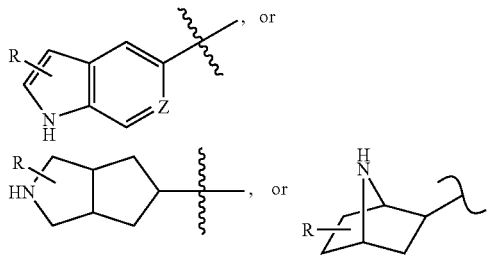

then, unless otherwise defined, a substituent "R" may reside on any atom of the fused ring system, assuming replacement of a depicted hydrogen (example the —NH— in the formula above), implied hydrogen (for example as in the formula above, where the hydrogens are not shown but understood to be present), or expressly defined hydrogen (for example where in the formula above, "Z" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the formula:

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

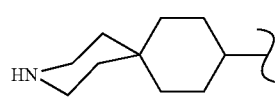

"Acyl" means a —C(O)R radical where R is optionally substituted alkyl, optionally substituted alkenyl, cycloalkyl, cycloalkylalkyl, aryl, aralkyl, heteroaryl, heteroaralkyl, heterocycloalkyl, or heterocycloalkylalkyl, as defined herein, e.g., acetyl, trifluoromethylcarbonyl, or 2-methoxyethylcarbonyl, and the like.

"Acylamino" means a —NRR' radical where R is hydrogen, hydroxy, alkyl, or alkoxy and R' is acyl, as defined herein.

"Acyloxy" means an —OR radical where R is acyl, as defined herein, e.g. cyanomethylcarbonyloxy, and the like.

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., surgery, radiation, and chemotherapy, etc.), "administration" and its variants are each understood to include concurrent and sequential introduction of the compound or prodrug thereof and other agents.

"Alkenyl" means a means a linear monovalent hydrocarbon radical of one to six carbon atoms or a branched monovalent hydrocarbon radical of three to 6 carbon atoms which radical contains at least one double bond, e.g., ethenyl, propenyl, 1-but-3-enyl, and 1-pent-3-enyl, and the like.

"Alkoxy" means an —OR group where R is alkyl group as defined herein. Examples include methoxy, ethoxy, propoxy, isopropoxy, and the like.

"Alkoxyalkyl" means an alkyl group, as defined herein, substituted with at least one, preferably one, two, or three, alkoxy groups as defined herein. Representative examples include methoxymethyl and the like.

"Alkoxyalkylamino" means an —NRR' group where R is hydrogen, alkyl, or alkoxyalkyl and R' is alkoxyalkyl, as defined herein.

"Alkoxyalkylaminoalkyl" means an alkyl group substituted with at least one, specifically one or two, alkoxyalkylamino group(s), as defined herein.

"Alkoxycarbonyl" means a —C(O)R group where R is alkoxy, as defined herein.

"Alkyl" means a linear saturated monovalent hydrocarbon radical of one to six carbon atoms or a branched saturated monovalent hydrocarbon radical of three to 6 carbon atoms, e.g., methyl, ethyl, propyl, 2-propyl, butyl (including all isomeric forms), or pentyl (including all isomeric forms), and the like.

"Alkylamino" means an —NHR group where R is alkyl, as defined herein.

"Alkylaminoalkyl" means an alkyl group substituted with one or two alkylamino groups, as defined herein.

"Alkylaminoalkyloxy" means an —OR group where R is alkylaminoalkyl, as defined herein.

"Alkylcarbonyl" means a —C(O)R group where R is alkyl, as defined herein.

"Alkynyl" means a linear monovalent hydrocarbon radical of one to six carbon atoms or a branched monovalent hydrocarbon radical of three to 6 carbon atoms which radical contains at least one triple bond, e.g., ethynyl, propynyl, butynyl, pentyN-2-yl and the like.

"Amino" means —NH$_2$.

"Aminoalkyl" means an alkyl group substituted with at least one, specifically one, two or three, amino groups.

"Aminoalkyloxy" means an —OR group where R is aminoalkyl, as defined herein.

"Aryl" means a monovalent six- to fourteeN-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Representative examples include phenyl, naphthyl, and indanyl, and the like.

"Arylalkyl" means an alkyl radical, as defined herein, substituted with one or two aryl groups, as defined herein, e.g., benzyl and phenethyl, and the like.

"Aryloxy" means an —OR group where R is aryl, as defined herein.

"Carboxyalkyl" means an alkyl group, as defined herein, substituted with at least one, specifically one or two, —C(O)OH group(s).

"Cycloalkyl" means a monocyclic or fused bicyclic, saturated or partially unsaturated (but not aromatic), monovalent hydrocarbon radical of three to ten carbon ring atoms. Fused bicyclic hydrocarbon radical includes bridged ring systems. Unless stated otherwise, the valency of the group may be located on any atom of any ring within the radical, valency rules permitting. One or two ring carbon atoms may be replaced by a —C(O)—, —C(S)—, or —C(=NH)— group. More specifically, the term cycloalkyl includes, but is not limited to, cyclopropyl, cyclobutyl, cyclopentyl, cyclohexyl, cyclohexyl, or cyclohex-3-enyl, and the like.

"Cycloalkylalkyl" means an alkyl group substituted with at least one, specifically one or two, cycloalkyl group(s) as defined herein.

"Dialkylamino" means a —NRR' radical where R and R' are alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl group substituted with one or two dialkylamino groups, as defined herein.

"Dialkylaminoalkyloxy" means an —OR group where R is dialkylaminoalkyl, as defined herein. Representative examples include 2-(N,N-diethylamino)-ethyloxy, and the like.

"Fused-polycyclic" or "fused ring system" means a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic. In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Halogen" or "halo" refers to fluorine, chlorine, bromine or iodine.

"Haloalkoxy" means an —OR group where R' is haloalkyl as defined herein, e.g., trifluoromethoxy or 2,2,2-trifluoroethoxy, and the like.

"Haloalkyl" mean an alkyl group substituted with one or more halogens, specifically one to five halo atoms, e.g., trifluoromethyl, 2-chloroethyl, and 2,2-difluoroethyl, and the like.

"Heteroaryl" means a monocyclic, fused bicyclic, or fused tricyclic, monovalent radical of 5 to 14 ring atoms containing one or more, specifically one, two, three, or four ring heteroatoms independently selected from —O—, —S(O)$_N$— (n is 0, 1, or 2), —N—, —N(R$^x$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^x$ is hydrogen, alkyl, hydroxy, alkoxy, acyl, or alkylsulfonyl. Fused bicyclic radical includes bridged ring systems. Unless stated otherwise, the valency may be located on any atom of any ring of the heteroaryl group, valency rules permitting. When the point of valency is located on the nitrogen, R$^x$ is absent. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridiN-3-yl, phthalaziN-3-yl, phthalaziN-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinoliN-4-yl or tetrahydroisoquinoliN-6-yl, and the like), pyrrolo[3,2-c]pyridinyl (including, for example, pyrrolo[3,2-c]pyridiN-2-yl or pyrrolo[3,2-c]pyridiN-7-yl, and the like), benzopyranyl, thiazolyl, isothiazolyl, thiadiazolyl, benzothiazolyl, benzothienyl, and the derivatives thereof, or N-oxide or a protected derivative thereof.

"Heteroarylalkyl" means an alkyl group, as defined herein, substituted with at least one, specifically one or two heteroaryl group(s), as defined herein.

"Heteroatom" refers to O, S, N, or P.

"Heterocycloalkyl" means a saturated or partially unsaturated (but not aromatic) monovalent monocyclic group of 3 to 8 ring atoms or a saturated or partially unsaturated (but not aromatic) monovalent fused bicyclic group of 5 to 12 ring atoms in which one or more, specifically one, two, three, or four ring heteroatoms independently selected from O, $S(O)_n$ (n is 0, 1, or 2), N, $N(R^y)$ (where $R^y$ is hydrogen, alkyl, hydroxy, alkoxy, acyl, or alkylsulfonyl), the remaining ring atoms being carbon. One or two ring carbon atoms may be replaced by a —C(O)—, —C(S)—, or —C(=NH)— group. Fused bicyclic radical includes bridged ring systems. Unless otherwise stated, the valency of the group may be located on any atom of any ring within the radical, valency rules permitting. When the point of valency is located on a nitrogen atom, $R^y$ is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, and tetrahydropyranyl, and the derivatives thereof and N-oxide or a protected derivative thereof.

"Heterocycloalkylalkyl" means an alkyl radical, as defined herein, substituted with one or two heterocycloalkyl groups, as defined herein, e.g., morpholinylmethyl, N-pyrrolidinylethyl, and 3-(N-azetidinyl)propyl, and the like.

"Heterocycloalkylalkyloxy means an —OR group where R is heterocycloalkylalkyl, as defined herein.

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

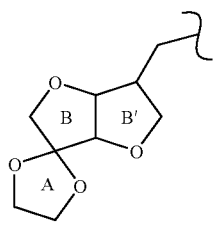

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted aryl$C_{1-8}$ alkyl," optional substitution may occur on both the "$C_{1-8}$ alkyl" portion and the "aryl" portion of the molecule may or may not be substituted. A list of exemplary optional substitutions is presented below in the definition of "substituted."

"Optionally substituted alkoxy" means an —OR group where R is optionally substituted alkyl, as defined herein.

"Optionally substituted alkyl" means an alkyl radical, as defined herein, optionally substituted with one or more group(s), specifically one, two, three, four, or five groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, halo, carboxy, alkylcarbonylamino, alkylcarbonyloxy, alkyl-$S(O)_{0-2}$—, alkenyl-$S(O)_{0-2}$—, aminosulfonyl, alkylaminosulfonyl, dialkylaminosulfonyl, alkylsulfonyl-$NR^c$— (where $R^c$ is hydrogen, alkyl, optionally substituted alkenyl, hydroxy, alkoxy, alkenyloxy, or cyanoalkyl), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —$C(O)NR^aR^b$ (where $R^a$ and $R^b$ are independently hydrogen, alkyl, optionally substituted alkenyl, hydroxy, alkoxy, alkenyloxy, or cyanoalkyl).

"Optionally substituted alkenyl" means an alkyl radical, as defined herein, optionally substituted with one or more group(s), specifically one, two, three, four, or five groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, halo, carboxy, alkylcarbonylamino, alkylcarbonyloxy, alkyl-$S(O)_{0-2}$—, alkenyl-$S(O)_{0-2}$—, aminosulfonyl, alkylaminosulfonyl, dialkylaminosulfonyl, alkylsulfonyl-$NR^c$— (where $R^c$ is hydrogen, alkyl, optionally substituted alkenyl, hydroxy, alkoxy, alkenyloxy, or cyanoalkyl), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —$C(O)NR^aR^b$ (where $R^a$ and $R^b$ are independently hydrogen, alkyl, optionally substituted alkenyl, hydroxy, alkoxy, alkenyloxy, or cyanoalkyl).

"Optionally substituted amino" refers to the group —N(H)R or —N(R)R where each R is independently selected from the group: optionally substituted alkyl, optionally substituted alkoxy, optionally substituted aryl, optionally substituted heterocycloalkyl, optionally substituted heteroaryl, acyl, carboxy, alkoxycarbonyl, —$S(O)_2$-(optionally substituted alkyl), —$S(O)_2$-optionally substituted aryl), —$S(O)_2$-(optionally substituted heterocycloalkyl), —$S(O)_2$-(optionally substituted heteroaryl), and —$S(O)_2$-(optionally substituted heteroaryl). For example, "optionally substituted amino" includes diethylamino, methylsulfonylamino, and furanyl-oxy-sulfonamino.

"Optionally substituted aminoalkyl" means an alkyl group, as defined herein, substituted with at least one, specifically one or two, optionally substituted amino group(s), as defined herein.

"Optionally substituted aryl" means an aryl group, as defined herein, optionally substituted with one, two, or three substituents independently selected from acyl, acylamino, acyloxy, optionally substituted alkyl, optionally substituted alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, or aryl is pentafluorophenyl. Within the optional substituents on "aryl", the alkyl and alkenyl, either alone or as part of another group (including, for example, the alkyl in alkoxycarbonyl), are independently optionally substituted with one, two, three, four, or five halo.

"Optionally substituted arylalkyl" means an alkyl group, as defined herein, substituted with optionally substituted aryl, as defined herein.

"Optionally substituted cycloalkyl" means a cycloalkyl group, as defined herein, substituted with one, two, or three groups independently selected from acyl, acyloxy, acylamino, optionally substituted alkyl, optionally substituted alkenyl, alkoxy, alkenyloxy, alkoxycarbonyl, alkenyloxycarbonyl, alkylthio, alkylsulfinyl, alkylsulfonyl, aminosulfonyl, alkylaminosulfonyl, dialkylaminosulfonyl, alkylsulfonylamino, halo, hydroxy, amino, alkylamino, dialkylamino, aminocarbonyl, alkylaminocarbonyl, dialkylaminocarbonyl, nitro, alkoxyalkyloxy, aminoalkoxy, alkylaminoalkoxy, dialkylaminoalkoxy, carboxy, and cyano. Within the above optional substitutents on "cycloalkyl", the alkyl and alkenyl, either alone or as part of another substituent on the cycloalkyl ring, are independently optionally substituted with one, two, three, four, or five halo, e.g. haloalkyl, haloalkoxy, haloalkenyloxy, or haloalkylsulfonyl.

"Optionally substituted cycloalkylalkyl" means an alkyl group substituted with at least one, specifically one or two, optionally substituted cycloalkyl groups, as defined herein.

"Optionally substituted heteroaryl" means a heteroaryl group optionally substituted with one, two, or three substituents independently selected from acyl, acylamino, acyloxy, optionally substituted alkyl, optionally substituted alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, alkylaminoalkoxy, and dialkylaminoalkoxy. Within the optional substituents on "heteroaryl", the alkyl and alkenyl, either alone or as part of another group (including, for example, the alkyl in alkoxycarbonyl), are independently optionally substituted with one, two, three, four, or five halo.

"Optionally substituted heteroarylalkyl" means an alkyl group, as defined herein, substituted with at least one, specifically one or two, optionally substituted heteroaryl group(s), as defined herein.

"Optionally substituted heterocycloalkyl" means a heterocycloalkyl group, as defined herein, optionally substituted with one, two or three substituents independently selected from acyl, acylamino, acyloxy, optionally substituted alkyl, optionally substituted alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, or aryl is pentafluorophenyl. Within the optional substituents on "heterocycloalkyl", the alkyl and alkenyl, either alone or as part of another group (including, for example, the alkyl in alkoxycarbonyl), are independently optionally substituted with one, two, three, four, or five halo.

"Optionally substituted heterocycloalkylalkyl" means an alkyl group, as defined herein, substituted with at least one, specifically one or two, optionally substituted heterocycloalkyl group(s) as defined herein.

"Yield" for each of the reactions described herein is expressed as a percentage of the theoretical yield.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilms' tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), HodgkiN's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

Embodiments of the Invention

One embodiment (A) of the Invention is directed to a Compound of Formula I where $R^1$ is hydrogen, optionally substituted alkyl, optionally substituted cycloallyl, optionally substituted cycloalkylalkyl, optionally substituted aryl, optionally substituted arylalkyl, optionally substituted heterocycloalkyl, optionally substituted heterocycloalkylalkyl, optionally substituted heteroaryl or optionally substituted heteroarylalkyl. Specifically, $R^1$ is hydrogen, optionally substituted alkyl, optionally substituted cycloalkyl, optionally substituted arylalkyl, or optionally substituted heterocycloalkylalkyl. More specifically, $R^1$ is hydrogen, alkyl, alkyl substituted with one or two hydroxy, alkyl substituted with alkoxy, cycloalkyl, arylalkyl, or heterocycloalkylalkyl. Even more specifically, $R^1$ is hydrogen, methyl, ethyl, propyl, isopropyl, 2-hydroxypropyl, 3-hydroxypropyl, 2-ethoxyethyl, 3-methoxypropyl, 3-ethoxypropyl, 3-isopropoxypropyl, cyclopropyl, cyclobutyl, cyclopentyl, cyclohexyl, benzyl, or 2-piperidin-1-ylethyl. Yet even more specifically, $R^1$ is ethyl, isopropyl, cyclopentyl, or cyclohexyl. Yet even more specifically, $R^1$ is ethyl.

Another embodiment (B) of the Invention is directed to a Compound of Formula I where $R^2$ is hydrogen or alkyl where the alkyl is optionally substituted with 1, 2, 3, 4, or 5 $R^8$ groups. Specifically, $R^2$ is hydrogen or alkyl where the alkyl is optionally substituted with one, two, or three $R^8$ groups. More specifically, $R^2$ is hydrogen or alkyl where the alkyl is optionally substituted with one, two, or three $R^8$ groups; and each $R^8$, when present, is independently selected from amino, alkylamino, dialkylamino, and halo. Even more specifically, $R^2$ is hydrogen, methyl, ethyl, propyl, isopropyl, tert-butyl, 3-aminopropyl, 3-(N-methylamino)-propyl, 3-(N,N-dimethylamino)-propyl, 2-fluoroethyl, or 2,2,2-trifluoroethyl. Yet even more specifically, $R^2$ is hydrogen or ethyl. Yet even more preferably, $R^2$ is hydrogen.

In another embodiment of the Invention, $R^2$ is hydrogen.

In another embodiment of the invention, $R^2$ is alkyl optionally substituted with 1, 2, 3, 4, or 5, $R^8$ groups. Specifically, $R^2$ is alkyl where the alkyl is optionally substituted with one, two, or three $R^8$ groups; and each $R^8$, when present, is independently selected from amino, alkylamino, dialkylamino, and halo. Even more specifically, $R^2$ is methyl, ethyl, propyl, isopropyl, tert-butyl, 3-aminopropyl, 3-(N-methylamino)-propyl, 3-(N,N-dimethylamino)-propyl, 2-fluoroethyl, or 2,2,2-trifluoroethyl. Yet even more specifically, $R^2$ is ethyl.

Another embodiment (C) of the Invention is directed to a Compound of Formula I where $R^4$ is optionally substituted alkyl. Specifically, $R^4$ is methyl or ethyl. More specifically, $R^4$ is methyl.

Another embodiment (D) of the Invention is directed to a Compound of Formula I where $R^6$ is acyl. More specifically, $R^6$ is alkylcarbonyl. Even more specifically, $R^6$ is acetyl.

Another embodiment (E) of the Invention is directed to a Compound of Formula I where $R^6$ is phenyl optionally substituted with 1, 2, 3, 4, or 5 $R^9$ groups. Specifically, $R^6$ is phenyl optionally substituted with one or two $R^9$ groups; and each $R^9$, when present, is independently selected from aryl, halo, alkoxy, aryloxy, and haloalkyl. More specifically, $R^6$ is phenyl optionally substituted with one or two $R^9$ groups; and each $R^9$, when present, is independently selected from phenyl, fluoro, chloro, methoxy, phenyloxy, and trifluoromethyl. Even more specifically, $R^6$ is phenyl, phenyl substituted with phenyl, fluorophenyl, difluorophenyl, chlorophenyl, dichlorophenyl, phenyl substituted with chloro and fluoro, methoxyphenyl, dimethoxyphenyl, phenyloxyphenyl, or trifluoromethylphenyl. Yet even more specifically, $R^6$ is phenyl, 2-phenyl-phenyl, 3-phenyl-phenyl, 4-phenyl-phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 3-chloro-4-fluorophenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 4-phenyloxyphenyl, 2-trifluoromethylphenyl, 3-trifluoromethylphenyl, or 4-trifluoromethylphenyl.

Another embodiment (F) of the Invention is directed to a Compound of Formula I where $R^6$ is phenyl substituted with 1, 2, 3, 4, or 5 $R^9$ groups.

Another embodiment (G) of the Invention is directed to a Compound of Formula I where $R^6$ is heteroaryl optionally substituted with 1, 2, 3, 4, or 5 $R^9$ groups.

A more specific embodiment (G1) of embodiment G is a Compound of Formula I where $R^6$ is a 6-membered heteroaryl optionally substituted with one or two $R^9$. More specifically, $R^6$ is pyridinyl, pyrazinyl, pyrimidinyl, or pyridazinyl each of which is optionally substituted with one $R^9$ where $R^9$, when present, is halo. Even more specifically, $R^6$ is pyridiN-2-yl, pyridiN-3-yl, pyridiN-4-yl, 3-fluoropyridiN-4-yl, pyrazin-2-yl, pyrazin-3-yl, pyrimidin-2-yl, pyrimidin-4-yl, pyrimidin-5-yl, pyridazin-3-yl, or pyridazin-4-yl, each of which is optionally substituted with one or two $R^9$.

In an even more specific embodiment (G2) of embodiment G is a Compound of Formula I where $R^6$ is pyrazinyl, pyrimidinyl, or pyridazinyl each of which is optionally substituted with one $R^9$ where $R^9$, when present, is halo. Even more specifically, $R^6$ is pyrazin-2-yl, pyrazin-3-yl, pyrimidin-2-yl, pyrimidin-4-yl, pyrimidin-5-yl, pyridazin-3-yl, or pyridazin-4-yl.

A more specific embodiment (G3) of embodiment G is a Compound of Formula I where $R^6$ is 5-membered heteroaryl optionally substituted with one or two $R^9$. Specifically $R^6$ is pyrazolyl, imidazolyl, thienyl, thiazolyl, oxazolyl, isoxazolyl, oxadiazolyl, furanyl, pyrrolyl, triazolyl, or tetrazolyl, each of which is optionally substituted with one $R^9$ where $R^9$, when present, is alkyl, arylalkyl, cyano, aryl, alkoxycarbonyl, or halo. More specifically, $R^6$ is pyrazol-1-yl, pyrazol-3-yl, pyrazol-4-yl, pyrazol-5-yl, imidazol-1-yl, imidazol-2-yl, imidazol-4-yl, imidazol-5-yl, thien-2-yl, thien-3-yl, thiazol-2-yl, thiazol-4-yl, thiazol-5-yl, oxazol-2-yl, oxazol-4-yl, oxazol-5-yl, isoxazol-3-yl, isoxazol-4-yl, isoxazol-5-yl, 1,2,3-oxadiazol-4-yl, 1,2,3-oxadiazol-5-yl, 1,3,4-oxadiazol-2-yl, 1,2,4-oxadiazol-3-yl, 1,2,4-oxadiazol-5-yl, furan-2-yl, furan-3-yl, pyrrol-1-yl, pyrrol-2-yl, pyrrol-3-yl, triazol-1-yl, triazol-4-yl, triazol-5-yl, tetrazol-1-yl, or tetrazol-5-yl; each of which is optionally substituted with one $R^9$ where $R^9$, when present, is methyl, benzyl, cyano, phenyl, N-tert-butoxycarbonyl, or chloro. Even more specifically, $R^6$ is pyrazol-3-yl, pyrazol-4-yl, pyrazol-5-yl, imidazol-2-yl, imidazol-4-yl, imidazol-5-yl, thien-2-yl, thien-3-yl, thiazol-2-yl, thiazol-4-yl, thiazol-5-yl, oxazol-2-yl, oxazol-4-yl, oxazol-5-yl, isoxazol-3-yl, isoxazol-4-yl, isoxazol-5-yl, 1,2,3-oxadiazol-4-yl, 1,2,3-oxadiazol-5-yl, 1,3,4-oxadiazol-2-yl, 1,2,4-oxadiazol-3-yl, 1,2,4-oxadiazol-5-yl, furan-2-yl, furan-3-yl, pyrrol-2-yl, pyrrol-3-yl, triazol-4-yl, triazol-5-yl, or tetrazol-5-yl; each of which is optionally substituted with one $R^9$ where $R^9$, when present, is methyl, benzyl, cyano, phenyl, N-tert-butoxycarbonyl, or chloro.

A more specific embodiment (G4) of embodiment G is a Compound of Formula I where $R^6$ is thienyl, pyrrolyl, furanyl, pyrazolyl, thiazolyl, isoxazolyl, imidazolyl, triazolyl, or tetrazolyl, each of which is optionally substituted with one $R^9$ where $R^9$, when present, is methyl, benzyl, cyano, phenyl, N-tert-butoxycarbonyl, or chloro. Specifically, $R^6$ is thien-2-yl, thien-3-yl, pyrrol-2-yl, furan-2-yl, furan-3-yl, pyrazol-3-yl, pyrazol-4-yl, pyrazol-5-yl, thiazol-2-yl, thiazol-5-yl, isoxazol-4-yl, imidazol-5-yl, triazol-5-yl, tetrazol-5-yl, each of which is optionally substituted with one $R^9$ where $R^9$, when present, is methyl, benzyl, cyano, phenyl, N-tert-butoxycarbonyl, or chloro. More specifically, $R^6$ is thien-2-yl, thien-3-yl, 5-cyano-thien-2-yl, 4-methyl-thien-2-yl, 4-methyl-thien-3-yl, 5-chloro-thien-5-yl, 5-phenyl-thien-2-yl, pyrrol-2-yl, N-tert-butoxycarbonyl-pyrrol-2-yl, N-methyl-pyrrol-2-yl, furan-2-yl, furan-3-yl, pyrazol-3-yl, pyrazol-4-yl, N-benzyl-pyrazol-4-yl, pyrazol-5-yl, thiazol-2-yl, thiazol-5-yl, isoxazol-4-yl, imidazol-5-yl, triazol-5-yl, tetrazol-5-yl, A more specific embodiment (G5) of embodiment G is a Compound of Formula I where $R^6$ is thien-2-yl, thien-3-yl, pyrrol-2-yl, furan-2-yl, furan-3-yl, pyrazol-3-yl, pyrazol-4-yl, pyrazol-5-yl, thiazol-2-yl, thiazol-5-yl, isoxazol-4-yl, imidazol-5-yl, triazol-5-yl, or tetrazol-5-yl, each of which is optionally substituted with one $R^9$ where $R^9$, when present, is methyl, benzyl, cyano, phenyl, N-tert-butoxycarbonyl, or chloro.

A more specific embodiment (G6) of embodiment G is a Compound of Formula I where $R^6$ is indolyl, benzimidazolyl, benzofuranyl, benzoxazolyl, or benzoisoxazolyl each of which is optionally substituted with 1, 2, 3, 4, or 5 $R^9$ groups. Specifically, $R^6$ is indol-2-yl, indol-3-yl, indol-4-yl, indol-5-yl, indol-6-yl, indol-7-yl, benzimidazol-2-yl, benzimidazol-4-yl, benzimidazol-5-yl, benzimidazol-6-yl, benzimidazol-7-yl, benzofuran-2-yl, benzofuran-3-yl, benzofuran-4-yl, benzofuran-5-yl, benzofuran-6-yl, benzofuran-7-yl, benzoxazol-2-yl, benzoxazol-4-yl, benzoxazol-5-yl, benzoxazol-6-yl, benzoxazol-7-yl, benzoisoxazol-3-yl, benzoisoxazol-4-yl, benzoisoxazol-5-yl, benzoisoxazol-6-yl, or benzoisoxazol-7-yl; each of which is optionally substituted with 1, 2, 3, 4, or 5 $R^9$ groups. More specifically, $R^6$ is indol-6-yl.

Another embodiment of the Invention (H) is a Compound of Formula 1 where $R^1$ is hydrogen, optionally substituted alkyl, optionally substituted cycloalkyl, optionally substituted heterocycloalkylalkyl, or optionally substituted arylalkyl; X is —NH—; $R^2$ is hydrogen or alkyl where the alkyl is optionally substituted with one or two $R^8$ groups; $R^4$ is alkyl; $R^5$ is hydrogen; $R^6$ is phenyl or heteroaryl wherein the phenyl and heteroaryl are optionally substituted with one, two, or three $R^9$ groups; each $R^8$, when present, is independently amino, alkylamino, dialkylamino, or halo; and each $R^9$, when present, is independently alkyl, arylalkyl, cyano, aryl, alkoxycarbonyl, or halo.

Another embodiment of the Invention (J) is a Compound of Formula 1 where $R^6$ is pyrazol-3-yl, pyrazol-4-yl, pyrazol-5-yl, imidazol-2-yl, imidazol-4-yl, imidazol-5-yl, thien-2-yl, thien-3-yl, thiazol-2-yl, thiazol-4-yl, thiazol-5-yl, oxazol-2-yl, oxazol-4-yl, oxazol-5-yl, isoxazol-3-yl, isoxazol-4-yl, isoxazol-5-yl, 1,2,3-oxadiazol-4-yl, 1,2,3-oxadiazol-5-yl, 1,3,4-oxadiazol-2-yl, 1,2,4-oxadiazol-3-yl, 1,2,4-oxadiazol-5-yl, furan-2-yl, furan-3-yl, pyrrol-2-yl, pyrrol-3-yl, triazol-4-yl, triazol-5-yl, or tetrazol-5-yl; each of which is optionally substituted with 1, 2, 3, 4, or 5 $R^9$ groups.

Another embodiment (K) of the Invention is a Compound of Formula I where $R^1$ is alkyl or cycloalkyl; $R^4$ is methyl; and $R^6$ is heteroaryl optionally substituted with one or two $R^9$ groups. Specifically, each $R^9$, when present, is independently alkyl, arylalkyl, cyano, aryl, alkoxycarbonyl, or halo. Specifically, $R^6$ is pyrazol-3-yl, pyrazol-4-yl, pyrazol-5-yl, imidazol-2-yl, imidazol-4-yl, imidazol-5-yl, thien-2-yl, thien-3-yl, thiazol-2-yl, thiazol-4-yl, thiazol-5-yl, oxazol-2-yl, oxazol-4-yl, oxazol-5-yl, isoxazol-3-yl, isoxazol-4-yl, isoxazol-5-yl, 1,2,3-oxadiazol-4-yl, 1,2,3-oxadiazol-5-yl, 1,3,4-oxadiazol-2-yl, 1,2,4-oxadiazol-3-yl, 1,2,4-oxadiazol-5-yl, furan-2-yl, furan-3-yl, pyrrol-2-yl, pyrrol-3-yl, triazol-4-yl, triazol-5-yl, or tetrazol-5-yl; each of which is optionally substituted with one $R^9$ where $R^9$, when present, is methyl, benzyl, cyano, phenyl, or N-tert-butoxycarbonyl.

A more specific embodiment (K1) of embodiment K is a Compound of Formula I where $R^2$ is hydrogen.

A more specific embodiment (K2) of embodiment K is a Compound of Formula I where $R^2$ is methyl or ethyl.

Another embodiment (L) of the Invention is a Compound of Formula I where $R^1$ is alkyl or cycloalkyl; $R^4$ is methyl; and $R^6$ is phenyl optionally substituted with one or two $R^9$ groups. Specifically each $R^9$, when present, is independently halo, alkoxy, or haloalkyl.

Another embodiment (M) of the Invention is a Compound of Formula I where $R^1$ is alkyl or cycloalkyl; $R^4$ is methyl; and $R^2$ is hydrogen.

Another embodiment (N) of the Invention is a Compound of Formula I where $R^1$ is alkyl or cycloalkyl; $R^4$ is methyl; and $R^2$ is optionally substituted alkyl.

Another embodiment (P) of the Invention is a method of treating disease, disorder, or syndrome where the disease is associated with uncontrolled, abnormal, and/or unwanted cellular activities effected directly or indirectly by PI3Kα which method comprises administering to a human in need thereof a therapeutically effective amount of a compound of Formula I or II or a pharmaceutically acceptable salt, solvate, or a pharmaceutical composition thereof. Specifically, the Compound is of Formula I.

Another embodiment (Q) of the invention is directed to a method of treating a disease, disorder, or syndrome which method comprises administering to a patient a therapeutically effective amount of a compound of Formula I or a pharmaceutically acceptable salt or solvate thereof, or a pharmaceutical composition comprising a therapeutically effective amount of a compound of Formula I and a pharmaceutically acceptable carrier, excipient, or diluent. Specifically, the disease is cancer. More specifically, the cancer is breast cancer, colon cancer, rectal cancer, endometrial cancer, gastric carcinoma, glioblastoma, hepatocellular carcinoma, small cell lung cancer, non-small cell lung cancer, melanoma, ovarian cancer, cervical cancer, pancreatic cancer, prostate carcinoma, acute myelogenous leukemia (AML), chronic myelogenous leukemia (CML), or thyroid carcinoma. Even more specifically, the cancer is ovarian cancer, cervical cancer, breast cancer, colon cancer, rectal cancer, or glioblastoma.

Another embodiment (R) of the Invetnion is directed to a method of treating a disease, disorder, or syndrome which method comprises administering to a patient a therapeutically effective amount of a compound of Formula II or a pharmaceutically acceptable salt or solvate thereof, or a pharmaceutical composition comprising a therapeutically effective amount of a compound of Formula II and a pharmaceutically acceptable carrier, excipient, or diluent. Specifically, the disease is cancer. More specifically, the cancer is breast cancer, colon cancer, rectal cancer, endometrial cancer, gastric carcinoma, glioblastoma, hepatocellular carcinoma, small cell lung cancer, non-small cell lung cancer, melanoma, ovarian cancer, cervical cancer, pancreatic cancer, prostate carcinoma, acute myelogenous leukemia (AML), chronic myelogenous leukemia (CML), or thyroid carcinoma. Even more specifically, the cancer is ovarian cancer, cervical cancer, breast cancer, colon cancer, rectal cancer, or glioblastomas.

Another aspect of the invention is a method of inhibiting proliferative activity in a cell, the method comprising administering to a cell or a plurality of cells an effective amount of a compound of Formula I or II, or a pharmaceutically acceptable salt, solvate, or prodrug thereof, or a pharmaceutical composition thereof. Specifically, the Compound is of Formula I.

Another aspect of the invention is directed to employing the compounds of the invention in a method of screening for candidate agents that bind to, for example PI3Kα. The protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro proteiN-protein binding assays, electrophoretic mobility shift assays, immunoassays for protein binding, functional assays (phosphorylation assays, etc.) and the like.

The determination of the binding of the candidate agent to, for example, PI3Kα can be done in a number of ways. In one example, the candidate agent (the compound of the invention) is labeled, for example, with a fluorescent or radioactive moiety and binding determined directly. For example, this may be done by attaching all or a portion of the PI3Kα protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

The term "labeled" as used herein is meant to include both direct and indirect labeling with a compound that provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, PI3Kα protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. The terms "candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to PI3Kα.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise carbocyclic or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to PI3Kα, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to PI3Kα protein for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to PI3Kα and thus is capable of binding to, and potentially modulating, the activity of the PI3Kα. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to PI3Kα with a higher affinity. Thus, if the candidate agent is labeled, the presence of the label on the support, coupled with a lack of competitor binding, may indicate the candidate agent is capable of binding to PI3Kα.

It may be of value to identify the binding site of PI3Kα. This can be done in a variety of ways. In one embodiment, once PI3Kα is identified as binding to the candidate agent, the PI3Kα is fragmented or modified and the assays repeated to identify the necessary components for binding.

Modulation is tested by screening for candidate agents capable of modulating the activity of PI3Kα comprising the steps of combining a candidate agent with PI3Kα, as above, and determining an alteration in the biological activity of the PI3Kα. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native PI3Kα, but cannot bind to modified PI3Kα.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which may be used to facilitate optimal proteiN-protein binding and/or reduce non-specific or background interactions. Also reagents that otherwise improve the efficiency of the assay, such as protease inhibitors, nuclease inhibitors, anti-microbial agents, etc., may be used. The mixture of components can be added in any order that provides for the requisite binding.

One of ordinary skill in the art would understand that certain crystallized, proteiN-ligand complexes, in particular PI3Kα-ligand-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

Representative Compounds

Representative compounds of Formula I and/or II are depicted below. The examples are merely illustrative and do not limit the scope of the invention in any way. Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Names were generated using ACD/Labs naming software 8.00 release, product version 8.08.

TABLE 1

| Example | Structure | Name |
|---|---|---|
| 1 | 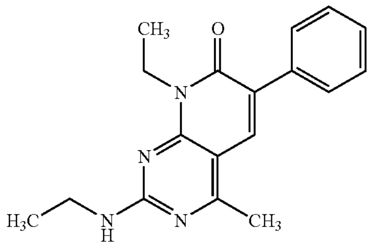 | 8-ethyl-2-(ethylamino)-4-methyl-6-phenylpyrido[2,3-d]pyrimidin-7(8H)-one |
| 2 | 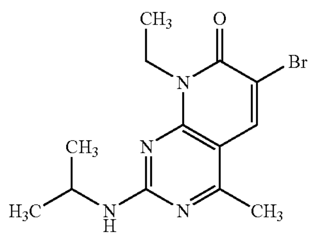 | 6-bromo-8-ethyl-4-methyl-2-[(1-methylethyl)amino]pyrido[2,3-d]pyrimidin-7(8H)-one |
| 3 | 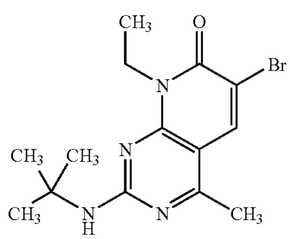 | 6-bromo-2-[(1,1-dimethylethyl)amino]-8-ethyl-4-methylpyrido[2,3-d]pyrimidin-7(8H)-one |
| 4 | 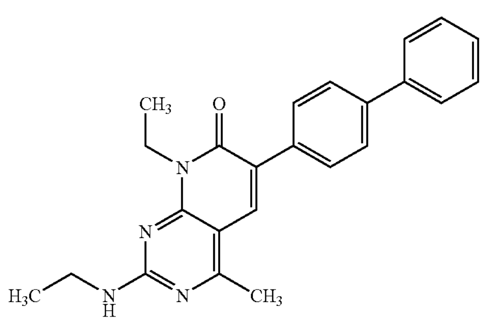 | 6-biphenyl-4-yl-8-ethyl-2-(ethylamino)-4-methylpyrido[2,3-d]pyrimidin-7(8H)-one |
| 5 | 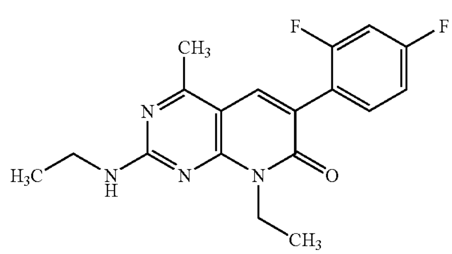 | 6-(2,4-difluorophenyl)-8-ethyl-2-(ethylamino)-4-methylpyrido[2,3-d]pyrimidin-7(8H)-one |
| 6 | 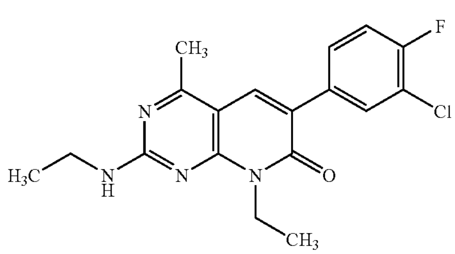 | 6-(3-chloro-4-fluorophenyl)-8-ethyl-2-(ethylamino)-4-methylpyrido[2,3-d]pyrimidin-7(8H)-one |

TABLE 1-continued

| Example | Structure | Name |
|---|---|---|
| 7 | 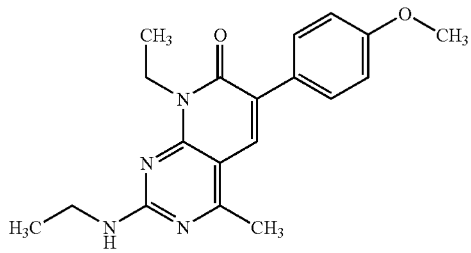 | 8-ethyl-2-(ethylamino)-4-methyl-6-[4-(methyloxy)phenyl]pyrido[2,3-d]pyrimidin-7(8H)-one |
| 8 | 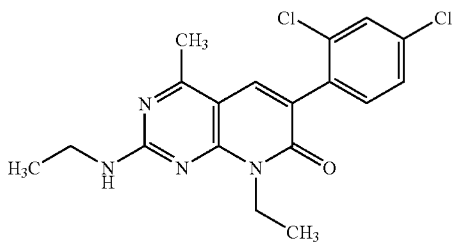 | 6-(2,4-dichlorophenyl)-8-ethyl-2-(ethylamino)-4-methylpyrido[2,3-d]pyrimidin-7(8H-one |
| 9 | 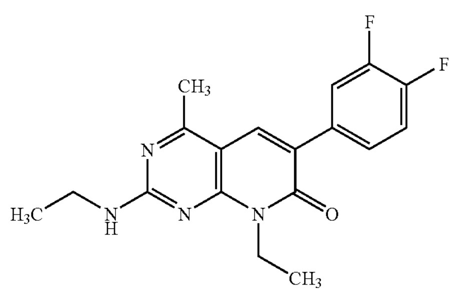 | 6-(3,4-difluorophenyl)-8-ethyl-2-(ethylamino)-4-methylpyrido[2,3-d]pyrimidin-7(8H)-one |
| 10 | 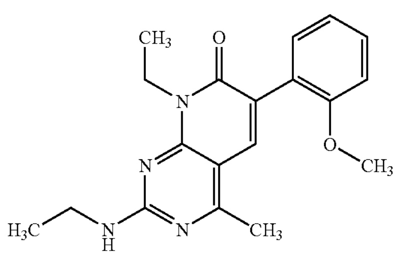 | 8-ethyl-2-(ethylamino)-4-methyl-6-[2-(methyloxy)phenyl]pyrido[2,3-d]pyrimidin-7(8H)-one |
| 11 | 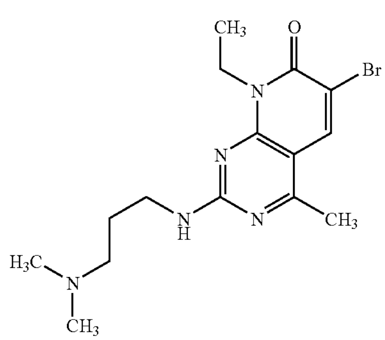 | 6-bromo-2-{[3-(dimethylamino)propyl]amino}-8-ethyl-4-methylpyrido[2,3-d]pyrimidin-7(8H)-one |

TABLE 1-continued

| Example | Structure | Name |
|---|---|---|
| 12 | 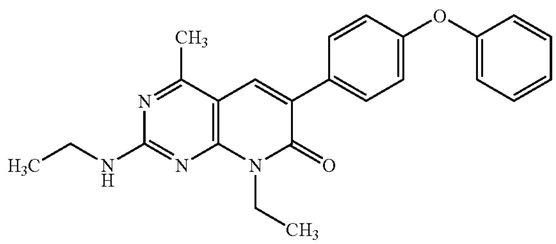 | 8-ethyl-2-(ethylamino)-4-methyl-6-[4-(phenyloxy)phenyl]pyrido[2,3-d]pyrimidin-7(8H)-one |
| 13 | 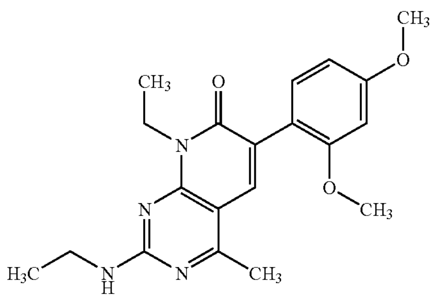 | 6-[2,4-bis(methyloxy)phenyl]-8-ethyl-2-(ethylamino)-4-methylpyrido[2,3-d]pyrimidin-7(8H)-one |
| 14 | 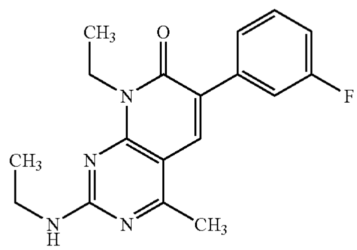 | 8-ethyl-2-(ethylamino)-6-(3-fluorophenyl)-4-methylpyrido[2,3-d]pyrimidin-7(8H)-one |
| 15 | 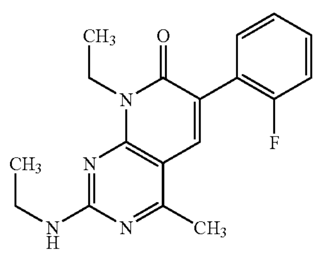 | 8-ethyl-2-(ethylamino)-6-(2-fluorophenyl)-4-methylpyrido[2,3-d]pyrimidin-7(8H)-one |
| 16 | 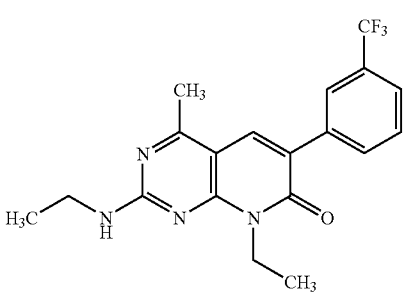 | 8-ethyl-2-(ethylamino)-4-methyl-6-[3-(trifluoromethyl)phenyl]pyrido[2,3-d]pyrimidin-7(8H)-one |
| 17 | 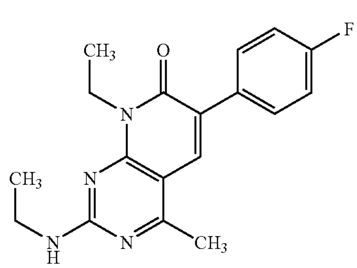 | 8-ethyl-2-(ethylamino)-6-(4-fluorophenyl)-4-methylpyrido[2,3-d]pyrimidin-7(8H)-one |

TABLE 1-continued

| Example | Structure | Name |
|---|---|---|
| 18 | 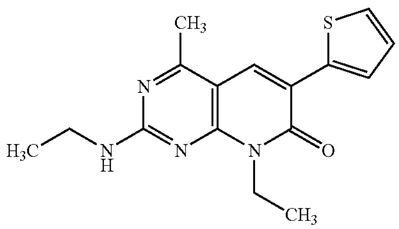 | 8-ethyl-2-(ethylamino)-4-methyl-6-(2-thienyl)pyrido[2,3-d]pyrimidin-7(8H)-one |
| 19 | 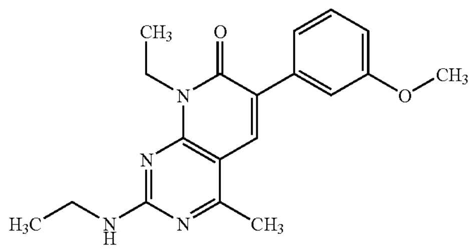 | 8-ethyl-2-(ethylamino)-4-methyl-6-[3-(methyloxy)phenyl]pyrido[2,3-d]pyrimidin-7(8H)-one |
| 20 | 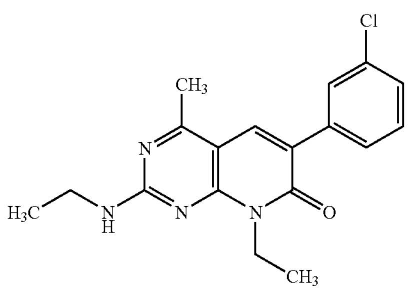 | 6-(3-chlorophenyl)-8-ethyl-2-(ethylamino)-4-methylpyrido[2,3-d]pyrimidin-7(8H)-one |
| 21 | 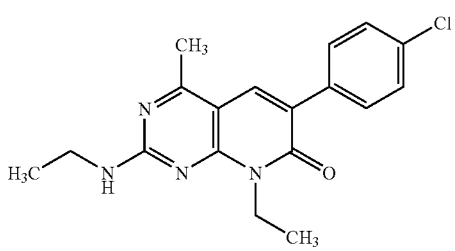 | 6-(4-chlorophenyl)-8-ethyl-2-(ethylamino)-4-methylpyrido[2,3-d]pyrimidin-7(8H)-one |
| 22 | 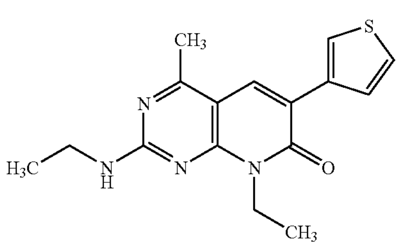 | 8-ethyl-2-(ethylamino)-4-methyl-6-(3-thienyl)pyrido[2,3-d]pyrimidin-7(8H)-one |
| 23 | 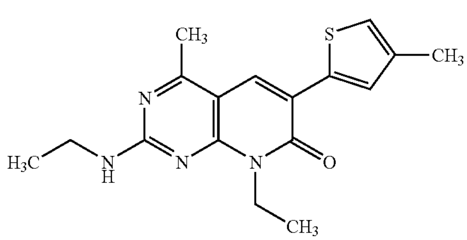 | 8-ethyl-2-(ethylamino)-4-methyl-6-(4-methyl-2-thienyl)pyrido[2,3-d]pyrimidin-7(8H)-one |

TABLE 1-continued

| Example | Structure | Name |
| --- | --- | --- |
| 24 | 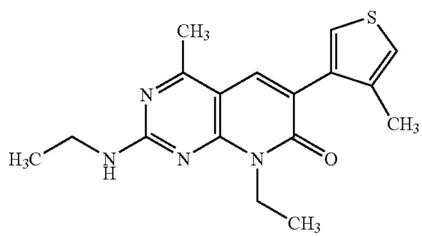 | 8-ethyl-2-(ethylamino)-4-methyl-6-(4-methyl-3-thienyl)pyrido[2,3-d]pyrimidin-7(8H)-one |
| 25 | 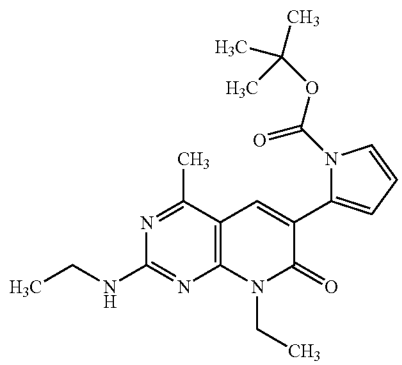 | 1,1-dimethylethyl 2-[8-ethyl-2-(ethylamino)-4-methyl-7-oxo-7,8-dihydropyrido[2,3-d]pyrimidin-6-yl]-1H-pyrrole-1-carboxylate |
| 26 | 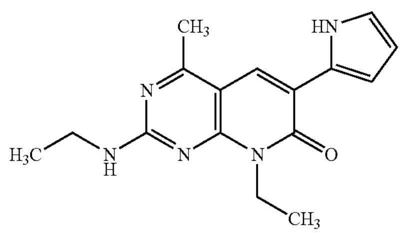 | 8-ethyl-2-(ethylamino)-4-methyl-6-(1H-pyrrol-2-yl)pyrido[2,3-d]pyrimidin-7(8H)-one |
| 27 | 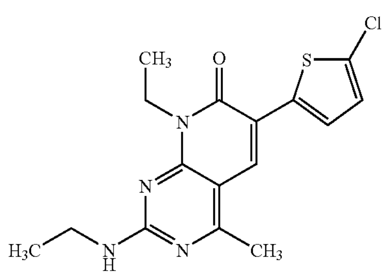 | 6-(5-chloro-2-thienyl)-8-ethyl-2-(ethylamino)-4-methylpyrido[2,3-d]pyrimidin-7(8H)-one |
| 28 | 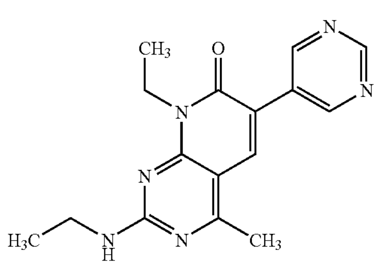 | 8-ethyl-2-(ethylamino)-4-methyl-6-pyrimidin-5-ylpyrido[2,3-d]pyrimidin-7(8H)-one |

TABLE 1-continued

| Example | Structure | Name |
|---|---|---|
| 29 | 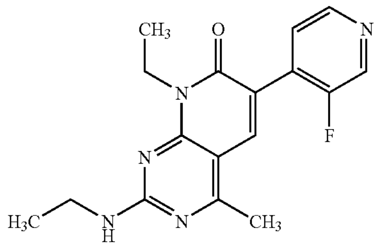 | 8-ethyl-2-(ethylamino)-6-(3-fluoropyridiN-4-yl)-4-methylpyrido[2,3-d]pyrimidin-7(8H)-one |
| 30 | 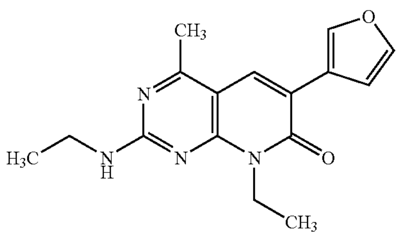 | 8-ethyl-2-(ethylamino)-6-furan-3-yl-4-methylpyrido[2,3-d]pyrimidin-7(8H)-one |
| 31 | 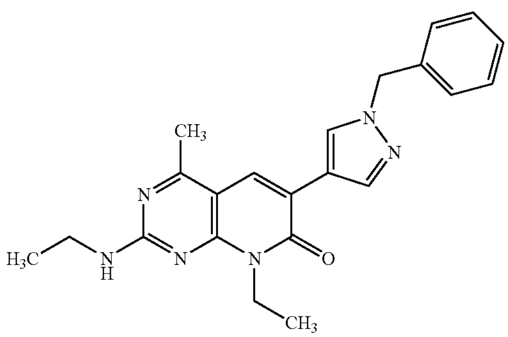 | 8-ethyl-2-(ethylamino)-4-methyl-6-[1-(phenylmethyl)-1H-pyrazol-4-yl]pyrido[2,3-d]pyrimidin-7(8H)-one |
| 32 | 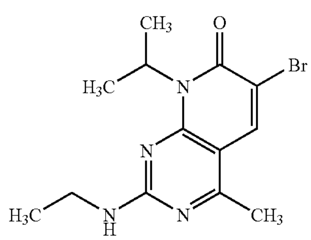 | 6-bromo-2-(ethylamino)-4-methyl-8-(1-methylethyl)pyrido[2,3-d]pyrimidin-7(8H)-one |
| 33 | 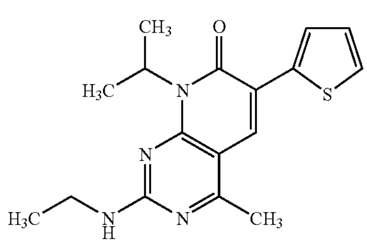 | 2-(ethylamino)-4-methyl-8-(1-methylethyl)-6-(2-thienyl)pyrido[2,3-d]pyrimidin-7(8H)-one |
| 34 | 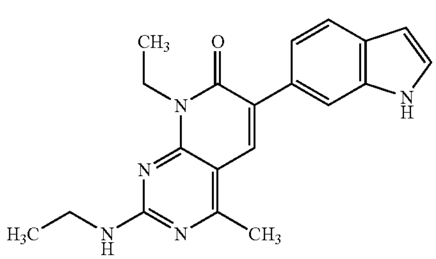 | 8-ethyl-2-(ethylamino)-6-(1H-indol-6-yl)-4-methylpyrido[2,3-d]pyrimidin-7(8H)-one |

TABLE 1-continued

| Example | Structure | Name |
|---|---|---|
| 35 | 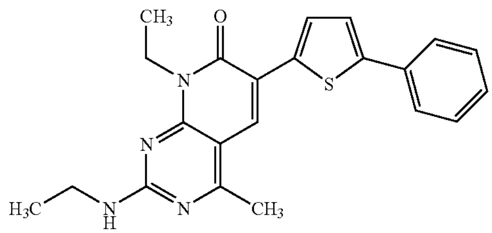 | 8-ethyl-2-(ethylamino)-4-methyl-6-(5-phenyl-2-thienyl)pyrido[2,3-d]pyrimidin-7(8H)-one |
| 36 | 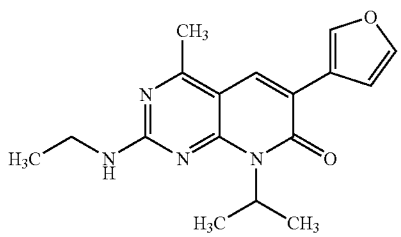 | 2-(ethylamino)-6-furan-3-yl-4-methyl-8-(1-methylethyl)pyrido[2,3-d]pyrimidin-7(8H)-one |
| 37 | 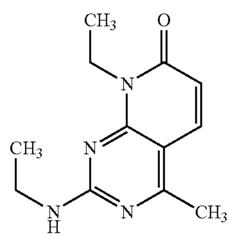 | 8-ethyl-2-(ethylamino)-4-methylpyrido[2,3-d]pyrimidin-7(8H)-one |
| 38 | 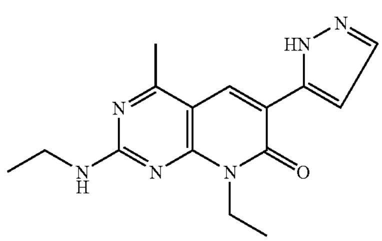 | 8-ethyl-2-(ethylamino)-4-methyl-6-(1H-pyrazol-5-yl)pyrido[2,3-d]pyrimidin-7(8H)-one |
| 39 | 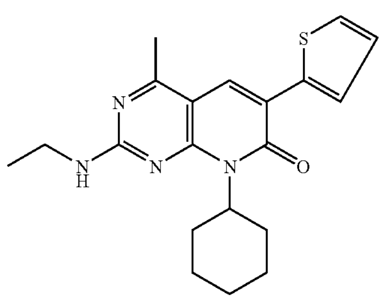 | 8-cyclohexyl-2-(ethylamino)-4-methyl-6-(2-thienyl)pyrido[2,3-d]pyrimidin-7(8H)-one |
| 40 | 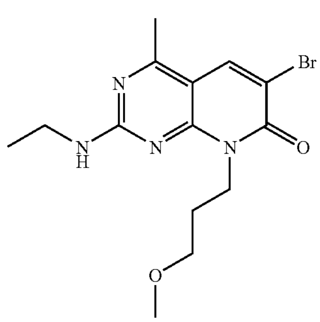 | 6-bromo-2-(ethylamino)-4-methyl-8-[3-(methyloxy)propyl]pyrido[2,3-d]pyrimidin-7(8H)-one |

TABLE 1-continued

| Example | Structure | Name |
|---|---|---|
| 41 | 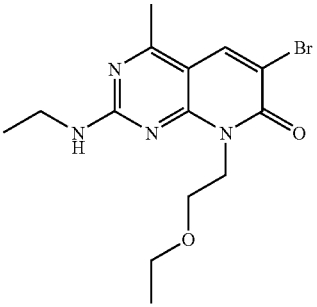 | 6-bromo-2-(ethylamino)-8-[2-(ethyloxy)ethyl]-4-methylpyrido[2,3-d]pyrimidin-7(8H)-one |
| 42 | 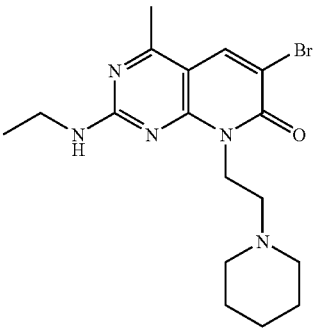 | 6-bromo-2-(ethylamino)-4-methyl-8-(2-piperidin-1-ylethyl)pyrido[2,3-d]pyrimidin-7(8H)-one |
| 43 | 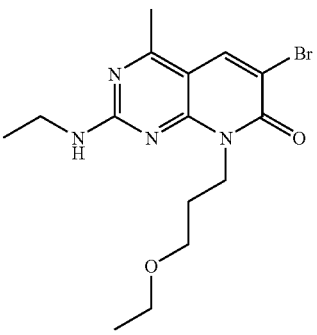 | 6-bromo-2-(ethylamino)-8-[3-(ethyloxy)propyl]-4-methylpyrido[2,3-d]pyrimidin-7(8H)-one |
| 44 | 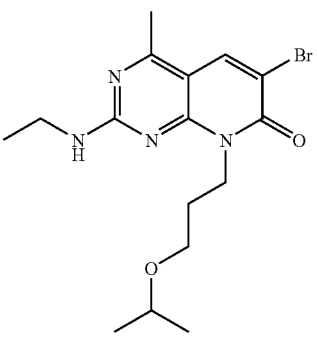 | 6-bromo-2-(ethylamino)-4-methyl-8-{3-[(1-methylethyl)oxy]propyl}pyrido[2,3-d]pyrimidin-7(8H)-one |
| 45 | 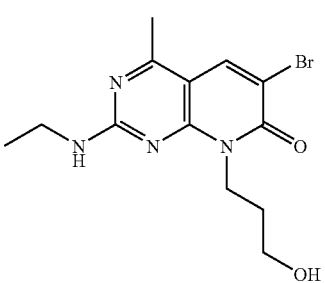 | 6-bromo-2-(ethylamino)-8-(3-hydroxypropyl)-4-methylpyrido[2,3-d]pyrimidin-7(8H)-one |

TABLE 1-continued

| Example | Structure | Name |
|---|---|---|
| 46 | 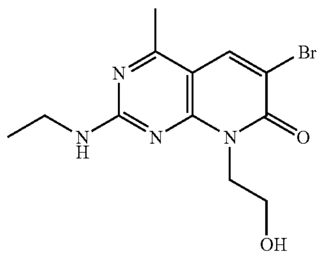 | 6-bromo-2-(ethylamino)-8-(2-hydroxyethyl)-4-methylpyrido[2,3-d]pyrimidin-7(8H)-one |
| 47 | 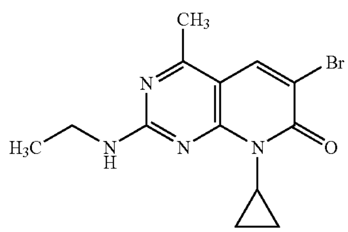 | 6-bromo-8-cyclopropyl-2-(ethylamino)-4-methylpyrido[2,3-d]pyrimidin-7(8H)-one |
| 48 | 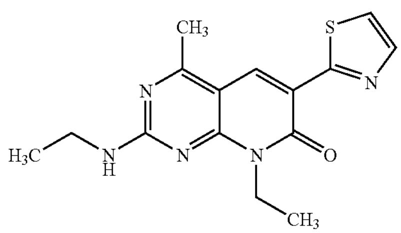 | 8-ethyl-2-(ethylamino)-4-methyl-6-(1,3-thiazol-2-yl)pyrido[2,3-d]pyrimidin-7(8H)-one |
| 49 | 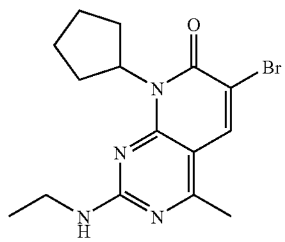 | 6-bromo-8-cyclopentyl-2-(ethylamino)-4-methylpyrido[2,3-d]pyrimidin-7(8H)-one |
| 50 | 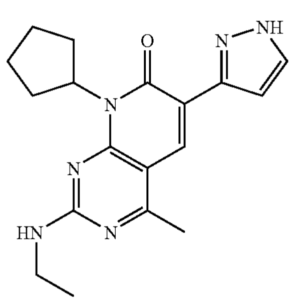 | 8-cyclopentyl-2-(ethylamino)-4-methyl-6-(1H-pyrazol-3-yl)pyrido[2,3-d]pyrimidin-7(8H)-one |
| 51 | 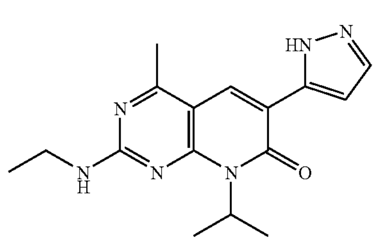 | 2-(ethylamino)-4-methyl-8-(1-methylethyl)-6-(1H-pyrazol-5-yl)pyrido[2,3-d]pyrimidin-7(8H)-one |

TABLE 1-continued

| Example | Structure | Name |
|---|---|---|
| 52 | 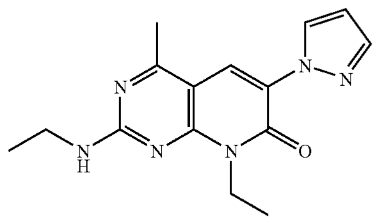 | 8-ethyl-2-(ethylamino)-4-methyl-6-(1H-pyrazol-1-yl)pyrido[2,3-d]pyrimidin-7(8H)-one |
| 53 | 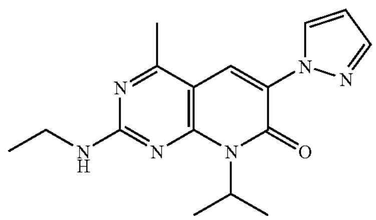 | 2-(ethylamino)-4-methyl-8-(1-methylethyl)-6-(1H-pyrazol-1-yl)pyrido[2,3-d]pyrimidin-7(8H)-one |
| 54 | 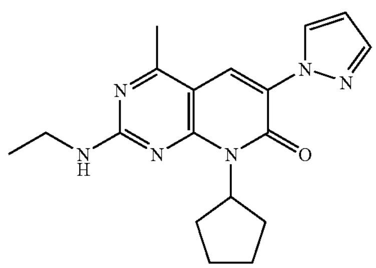 | 8-cyclopentyl-2-(ethylamino)-4-methyl-6-(1H-pyrazol-1-yl)pyrido[2,3-d]pyrimidin-7(8H)-one |
| 55 | 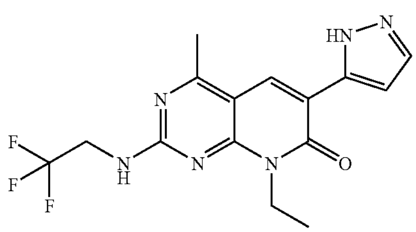 | 8-ethyl-4-methyl-6-(1H-pyrazol-5-yl)-2-[(2,2,2-trifluoroethyl)amino]pyrido[2,3-d]pyrimidin-7(8H)-one |
| 56 | 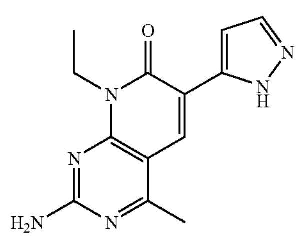 | 2-amino-8-ethyl-4-methyl-6-(1H-pyrazol-5-yl)pyrido[2,3-d]pyrimidin-7(8H)-one |
| 57 | 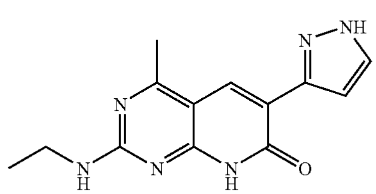 | 2-(ethylamino)-4-methyl-6-(1H-pyrazol-3-yl)pyrido[2,3-d]pyrimidin-7(8H)-one |

TABLE 1-continued

| Example | Structure | Name |
|---|---|---|
| 58 | 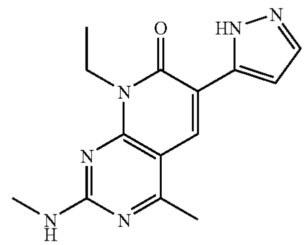 | 8-ethyl-4-methyl-2-(methylamino)-6-(1H-pyrazol-5-yl)pyrido[2,3-d]pyrimidin-7(8H)-one |
| 59 | 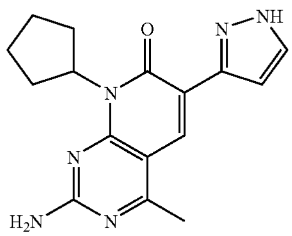 | 2-amino-8-cyclopentyl-4-methyl-6-(1H-pyrazol-3-yl)pyrido[2,3-d]pyrimidin-7(8H)-one |
| 60 | 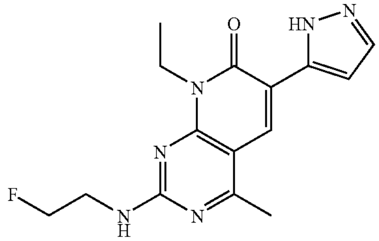 | 8-ethyl-2-[(2-fluoroethyl)amino]-4-methyl-6-(1H-pyrazol-5-yl)pyrido[2,3-d]pyrimidin-7(8H)-one |
| 61 | 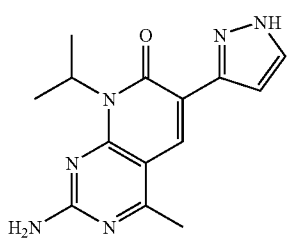 | 2-amino-4-methyl-8-(1-methylethyl)-6-(1H-pyrazol-3-yl)pyrido[2,3-d]pyrimidin-7(8H)-one |
| 62 | 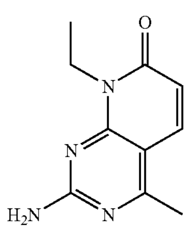 | 2-amino-8-ethyl-4-methylpyrido[2,3-d]pyrimidin-7(8H)-one |
| 63 | 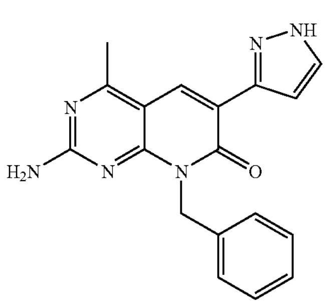 | 2-amino-4-methyl-8-(phenylmethyl)-6-(1H-pyrazol-3-yl)pyrido[2,3-d]pyrimidin-7(8H)-one |

TABLE 1-continued

| Example | Structure | Name |
|---|---|---|
| 64 | 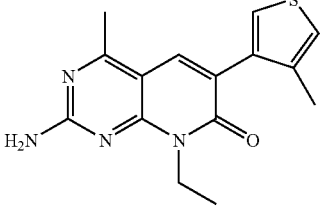 | 2-amino-8-ethyl-4-methyl-6-(4-methyl-3-thienyl)pyrido[2,3-d]pyrimidin-7(8H)-one |
| 65 | 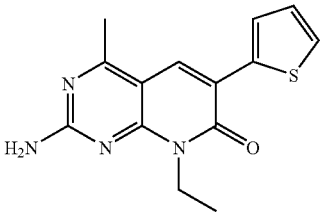 | 2-amino-8-ethyl-4-methyl-6-(2-thienyl)pyrido[2,3-d]pyrimidin-7(8H)-one |
| 66 | 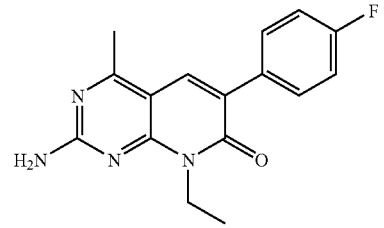 | 2-amino-8-ethyl-6-(4-fluorophenyl)-4-methylpyrido[2,3-d]pyrimidin-7(8H)-one |
| 67 | 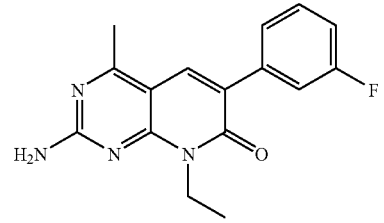 | 2-amino-8-ethyl-6-(3-fluorophenyl)-4-methylpyrido[2,3-d]pyrimidin-7(8H)-one |
| 68 | 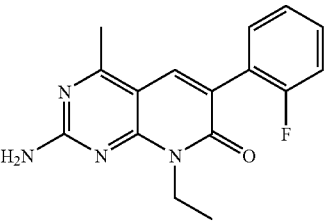 | 2-amino-8-ethyl-6-(2-fluorophenyl)-4-methylpyrido[2,3-d]pyrimidin-7(8H)-one |
| 69 | 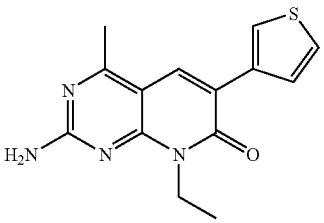 | 2-amino-8-ethyl-4-methyl-6-(3-thienyl)pyrido[2,3-d]pyrimidin-7(8H)-one |

TABLE 1-continued

| Example | Structure | Name |
| --- | --- | --- |
| 70 | 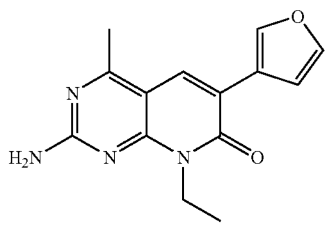 | 2-amino-8-ethyl-6-furan-3-yl-4-methylpyrido[2,3-d]pyrimidin-7(8H)-one |
| 71 | 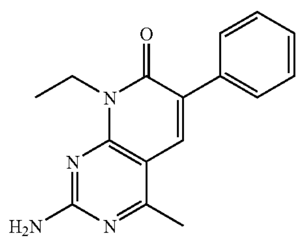 | 2-amino-8-ethyl-4-methyl-6-phenylpyrido[2,3-d]pyrimidin-7(8H)-one |
| 72 | 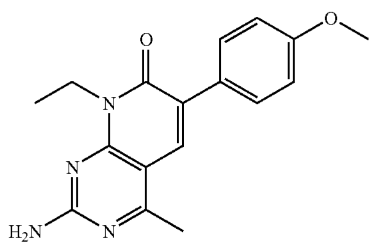 | 2-amino-8-ethyl-4-methyl-6-[4-(methyloxy)phenyl]pyrido[2,3-d]pyrimidin-7(8H)-one |
| 73 | 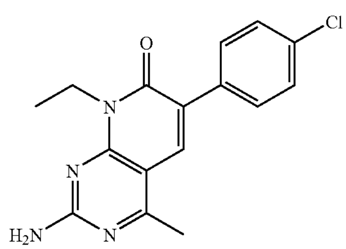 | 2-amino-6-(4-chlorophenyl)-8-ethyl-4-methylpyrido[2,3-d]pyrimidin-7(8H)-one |
| 74 | 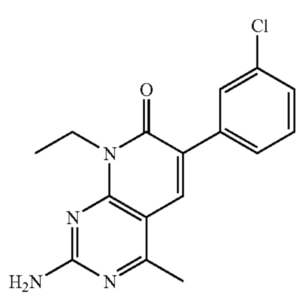 | 2-amino-6-(3-chlorophenyl)-8-ethyl-4-methylpyrido[2,3-d]pyrimidin-7(8H)-one |
| 75 | 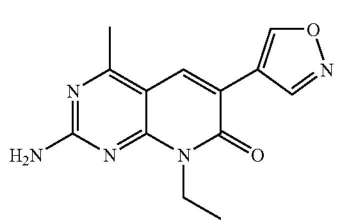 | 2-amino-8-ethyl-6-isoxazol-4-yl-4-methylpyrido[2,3-d]pyrimidin-7(8H)-one |

TABLE 1-continued

| Example | Structure | Name |
|---|---|---|
| 76 | 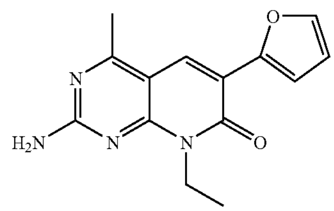 | 2-amino-8-ethyl-6-furan-2-yl-4-methylpyrido[2,3-d]pyrimidin-7(8H)-one |
| 77 | 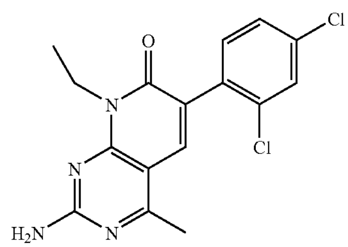 | 2-amino-6-(2,4-dichlorophenyl)-8-ethyl-4-methylpyrido[2,3-d]pyrimidin-7(8H)-one |
| 78 | 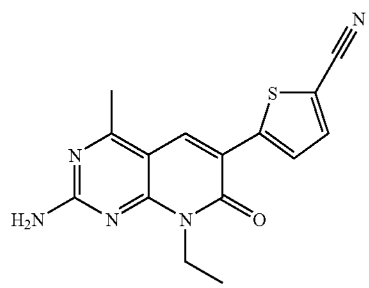 | 5-(2-amino-8-ethyl-4-methyl-7-oxo-7,8-dihydropyrido[2,3-d]pyrimidin-6-yl)thiophene-2-carbonitrile |
| 79 | 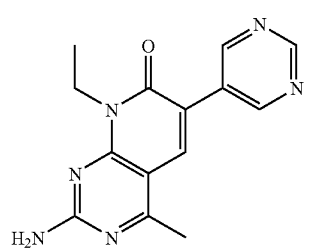 | 2-amino-8-ethyl-4-methyl-6-pyrimidin-5-ylpyrido[2,3-d]pyrimidin-7(8H)-one |
| 80 | 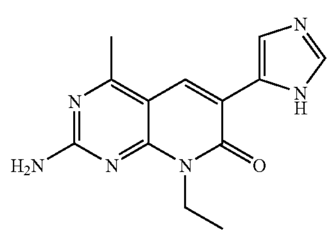 | 2-amino-8-ethyl-6-(1H-imidazol-5-yl)-4-methylpyrido[2,3-d]pyrimidin-7(8H)-one |
| 81 | 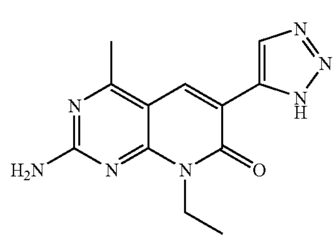 | 2-amino-8-ethyl-4-methyl-6-(1H-1,2,3-triazol-5-yl)pyrido[2,3-d]pyrimidin-7(8H)-one |

TABLE 1-continued

| Example | Structure | Name |
|---|---|---|
| 82 | 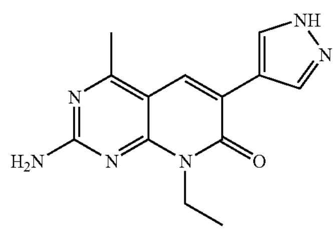 | 2-amino-8-ethyl-4-methyl-6-(1H-pyrazol-4-yl)pyrido[2,3-d]pyrimidin-7(8H)-one |
| 83 | 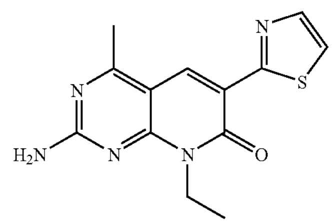 | 2-amino-8-ethyl-4-methyl-6-(1,3-thiazol-2-yl)pyrido[2,3-d]pyrimidin-7(8H)-one |
| 84 | 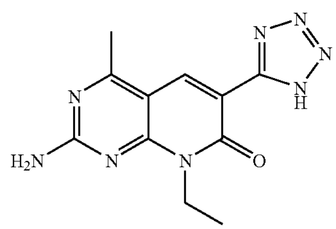 | 2-amino-8-ethyl-4-methyl-6-(1H-tetrazol-5-yl)pyrido[2,3-d]pyrimidin-7(8H)-one |
| 85 | 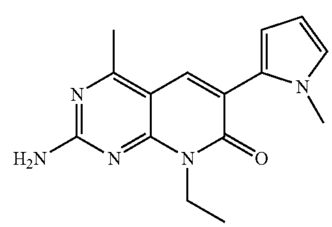 | 2-amino-8-ethyl-4-methyl-6-(1-methyl-1H-pyrrol-2-yl)pyrido[2,3-d]pyrimidin-7(8H)-one |
| 86 | 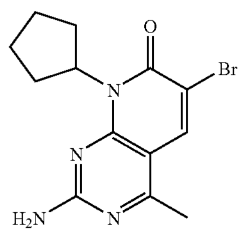 | 2-amino-6-bromo-8-cyclopentyl-4-methylpyrido[2,3-d]pyrimidin-7(8H)-one |
| 87 | 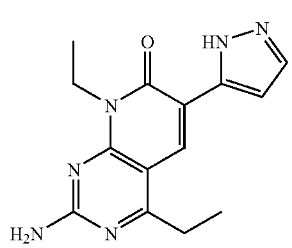 | 2-amino-4,8-diethyl-6-(1H-pyrazol-5-yl)pyrido[2,3-d]pyrimidin-7(8H)-one |

TABLE 1-continued

| Example | Structure | Name |
|---|---|---|
| 88 | 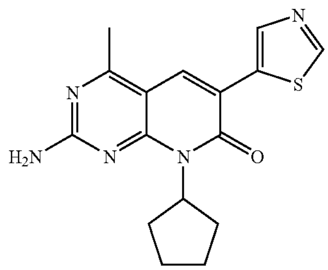 | 2-amino-8-cyclopentyl-4-methyl-6-(1,3-thiazol-5-yl)pyrido[2,3-d]pyrimidin-7(8H)-one |

General Administration

In one aspect, the invention provides pharmaceutical compositions comprising an inhibitor of PI3K according to the invention and a pharmaceutically acceptable carrier, excipient, or diluent. In certain other specific embodiments, administration is by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, specifically in unit dosage forms suitable for simple administration of precise dosages.

The compositions will include a conventional pharmaceutical carrier or excipient and a compound of the invention as the/an active agent, and, in addition, may include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

The choice of formulation depends on various factors such as the mode of drug administration (e.g., for oral administration, formulations in the form of tablets, pills or capsules) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol- and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Compressed gases may be used to disperse a compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see RemingtoN's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts or solvates, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

If formulated as a fixed dose, such combination products employ the compounds of this invention within the dosage range described above and the other pharmaceutically active agent(s) within its approved dosage range. Compounds of the instant invention may alternatively be used sequentially with known pharmaceutically acceptable agent(s) when a combination formulation is inappropriate.

Representative pharmaceutical formulations containing a compound of Formula I are described below in the Pharmaceutical Composition Examples.

Utility

Certain compounds of this invention have been tested using the assay described in Biological Example 1 and have been determined to be PI3K inhibitors. As such compounds of Formula I are useful for treating diseases, particularly cancer in which PI3K activity contributes to the pathology and/or symptomatology of the disease. For example, cancer in which PI3K activity contributes to its pathology and/or symptomatology include breast cancer, colon cancer, rectal cancer, endometrial cancer, gastric carcinoma, glioblastoma, hepatocellular carcinoma, small cell lung cancer, non-small cell lung cancer, melanoma, ovarian cancer, cervical cancer, pancreatic cancer, prostate carcinoma, acute myelogenous leukemia (AML), chronic myelogenous leukemia (CML), or thyroid carcinoma Suitable in vitro assays for measuring PI3K activity and the inhibition thereof by compounds are known in the art. For further details of an in vitro assay for measuring PI3K activity see Biological Examples, Example 1 infra. Following the examples disclosed herein, as well as that disclosed in the art, a person of ordinary skill in the art can determine the inhibitory activity of a compound of this invention.

Assays for measurement of in vitro efficacy in treatment of cancer are known in the art. In addition, cell-based tumor models are described in Biological Examples, Example 2, 3, and 4 infra.

Suitable in vivo models for cancer are known to those of ordinary skill in the art. For further details of in vivo models for prostate adenocarcinoma, glioblastoma, lung carcinoma, and melanoma, see Biological Examples 5, 6, 7, 8, 9, and 10, infra.

General Synthesis

Compounds of this invention can be made by the synthetic procedures described below. The starting materials and reagents used in preparing these compounds are either available from commercial suppliers such as Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4$^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure and over a temperature range from about −78° C. to about 150° C., more specifically from about 0° C. to about 125° C. and more specifically at about room (or ambient) temperature, e.g., about 20° C. Unless otherwise stated (as in the case of an hydrogenation), all reactions are performed under an atmosphere of nitrogen.

Prodrugs can be prepared by techniques known to one skilled in the art. These techniques generally modify appropriate functional groups in a given compound. These modified functional groups regenerate original functional groups by routine manipulation or in vivo. Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium. Series, and in Bioreversible Carriers in Drug Design, ed. Edward B. Roche, American Pharmaceutical Association and Pergamon Press, 1987, both of which are incorporated herein by reference for all purposes.

The compounds of the invention, or their pharmaceutically acceptable salts, may have asymmetric carbon atoms or quaternized nitrogen atoms in their structure. Compounds of Formula I that may be prepared through the syntheses described herein may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention. Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention. In particular, imidazol-5-yl and pyrazol-5-yl each can also exist in their respective tautomeric forms imidazol-4-yl and pyrazol-3-yl. Regardless of which structure or which terminology is used, each tautomer is included within the scope of the Invention.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. When compounds of Formula I contain groups such as hydroxy, carboxy, thiol or any group containing a nitrogen atom(s), these groups can be protected with a suitable "protecting group" or "protective group". A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of Formula I can be prepared by methods well known in the art.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The chemistry for the preparation of the compounds of this invention is known to those skilled in the art. In fact, there may be more than one process to prepare the compounds of the invention. For specific examples, see M. Barvian et al. J. Med. Chem. 2000, 43, 4606-4616; S, N. VanderWei et al. J. Med. Chem. 2005, 48, 2371-2387; P. L. Toogood et al. J. Med. Chem. 2005, 48, 2388-2406; J. Kasparec et al. Tetrahedron Letters 2003, 44, 4567-4570; and references cited therein. See also U.S. Pre-grant publication US2004/0009993 A1 (M. Angiolini et al.), which is incorporated herein by reference, and references cited therein. The following examples illustrate but do not limit the invention. All references cited herein are incorporated by reference in their entirety.

A compound of the invention where $R^1$ is optionally substituted alkyl, $R^2$ is hydrogen or optionally substituted alkyl, $R^4$ is methyl or ethyl, $R^6$ is phenyl or heteroaryl each of which is optionally substituted with 1, 2, 3, 4, or 5 $R^9$ groups (as defined in the Summary of the Invention), and $R^2$ is hydrogen can be prepared according to Scheme 1.

Scheme 1

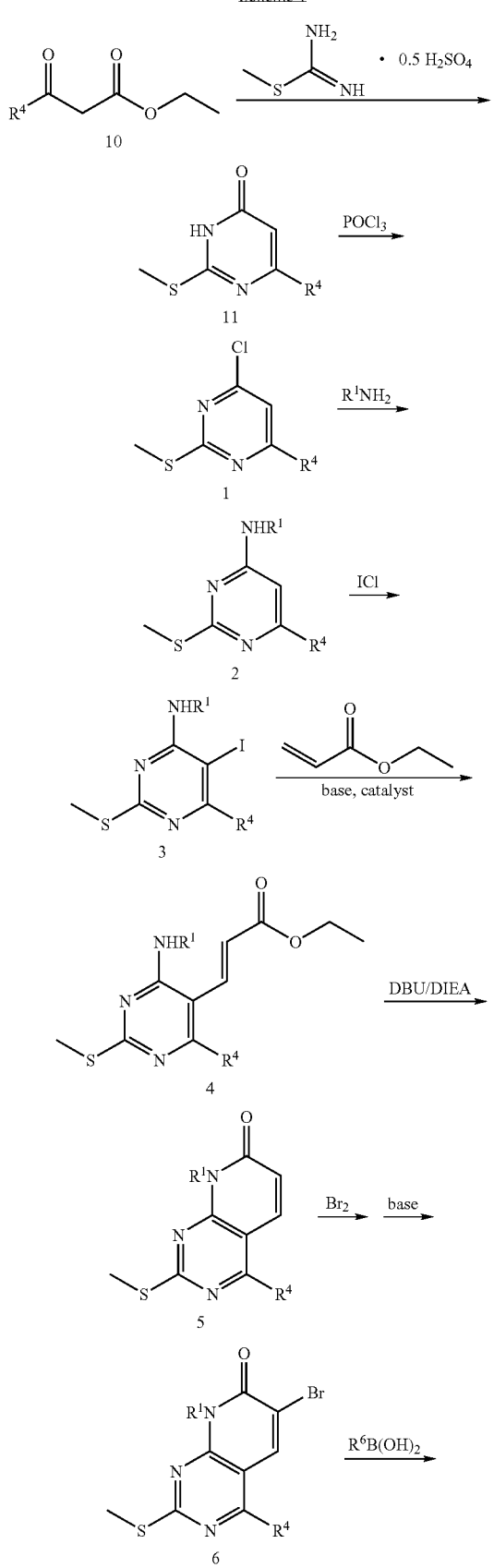

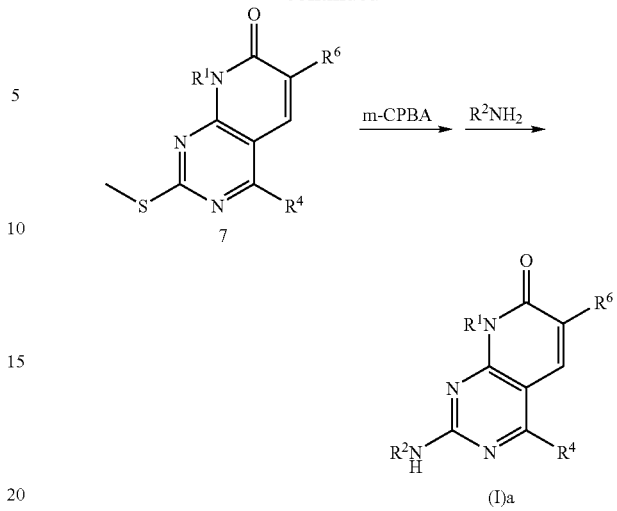

To a solution of commercially available 2-methyl-2-thiopseudourea sulfate in a solvent such as water is added a base such as sodium carbonate and an intermediate of formula 10 at room temperature. The reaction mixture is stirred for overnight or less. After neutralizing, 11 is collected through filtration and followed by drying under vacuum. 11 is then treated with $POCl_3$ and the reaction is heated to reflux for approximately 2 h and then concentrated under vacuum to dryness. 1 can be used directly in the next reaction without further purification.

An intermediate of formula 2 is prepared by reacting an intermediate of formula 1 with a primary amine $R^1NH_2$ in a solvent such as water and with heating. 2 is then treated with iodine monochloride in a solvent such as methanol at around 0° C. and allowed to react for approximately overnight or less as needed for the reaction to go to completion to form 3. After completion the residue is triturated with acetone. The intermediate 3 is then reacted in a solvent, such as DMA, with ethyl acrylate in the presence of a base, such as triethylamine, and in the presence of a catalyst, such as $Pd(OAc)_2$, and (+)BINAP. The reaction is heated to approximately 100° C. and allowed to react for approximately overnight or less as needed for the reaction to go to completion to form 4. 4 is then optionally purified by column chromatography.

5 is prepared by treating 4 with DBU in the presence of a base such as DIPEA at room temperature. Then the reaction mixture is heated to reflux and reacted for approximately 15 h. After evaporation of solvent, the residue is triturated with acetone and collected by filtration to yield 5.

6 is prepared by reacting 5 with a brominating agent such as $Br_2$ in a solvent such as DCM at room temperature. Then the reaction mixture is stirred for approximately overnight. The resulting product is filtered and then suspended in a solvent such as DCM and treated with a base such as triethylamine. The mixture is then washed with water and dried over a drying agent such as $Na_2SO_4$ to yield 6.

A Suzuki coupling is then performed using 6 reacting with a boronic acid (or ester) of formula $R^6B(OH)_2$ in a solvent(s) such as a $DME-H_2O$ mixture, in the presence of a catalyst such as Pd(dpppf) and a base such as triethylamine at room temperature. The reaction mixture is heated to reflux for approximately 4 h. After cooling to room temperature, the reaction mixture is partitioned with water and ethyl acetate. After separation, the organic layer is dried over a drying agent such as $Na_2SO_4$ to yield 7.

The methylthio group of 7 is then oxidized with m-CPBA in a solvent such as DCM at room temperature allowing to stir for approximately 4 h. After removal of the solvent under reduced pressure, the product is treated with an amine of formula R²NH₂ in a solvent such as dioxane and stirred at room temperature for approximately overnight to yield a Compound of Formula I.

Alternatively, a compound of the invention where R¹ is optionally substituted alkyl, R⁴ is methyl or ethyl, R⁶ is phenyl or heteroaryl each of which is optionally substituted with 1, 2, 3, 4, or 5 R⁹ groups (as defined in the Summary of the Invention), and R² is hydrogen can be prepared according to Scheme 2.

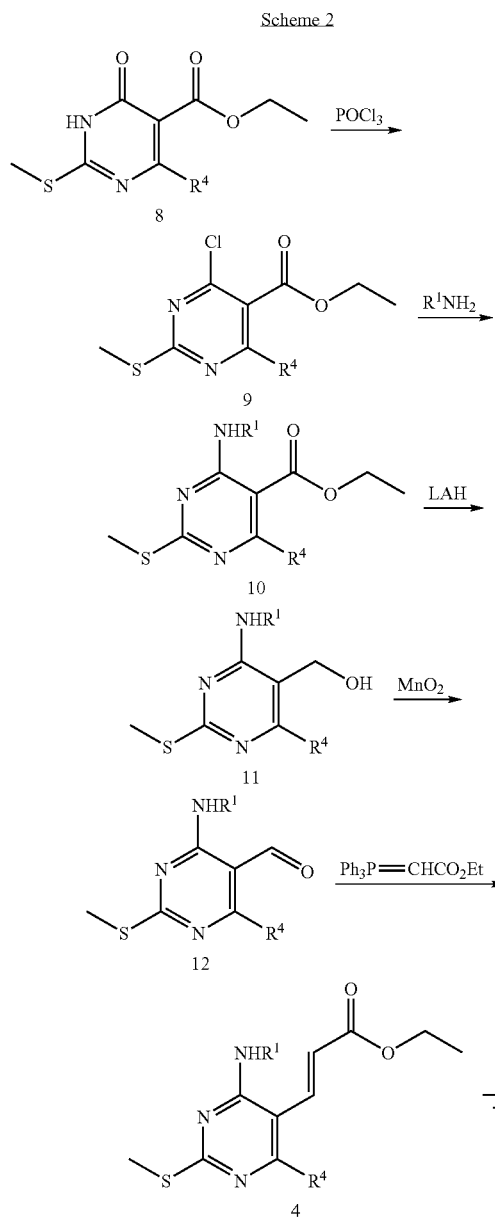

An intermediate of formula 9 is prepared by reacting an intermediate of formula 8 with neat POCl₃ and heating. 9 is then treated with a primary amine R¹NH₂ in a solvent such as water or THF and triethylamine at 0° C. to form 10. After removal of the solvent under reduced pressure, the intermediate 10 is then reacted with lithium aluminum hydride in a solvent such as THF at 0° C. After quenching and aqueous workup, solvent removal provided crystalline 11 without further purification. Treatment of 11 with manganese (II) dioxide in a solvent such as methylene chloride or chloroform at room temperature provided aldehyde 12 upon filtration and solvent removal. A Wittig reaction with aldehyde 12 can be employed with (carbethoxymethylene)triphenylphosphorane in refluxing THF to provide the common intermediate 4. 4 can then be used to prepare a Compound of Formula I using the procedures described in Scheme 1.

A compound of the invention where R¹ is optionally substituted alkyl, R⁴ is methyl or ethyl, R⁶ is phenyl or heteroaryl each of which is optionally substituted with 1, 2, 3, 4, or 5 R⁹ groups (as defined in the Summary of the Invention), and R² is hydrogen can be prepared according to Scheme 3.

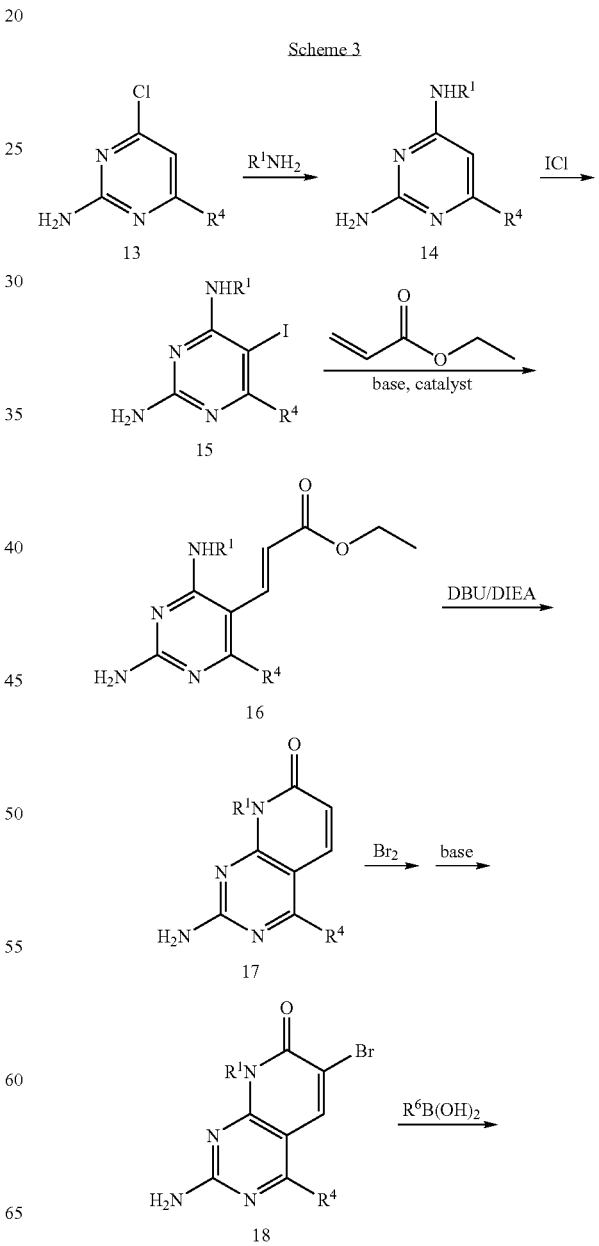

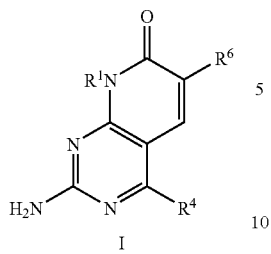

An intermediate of formula 14 is prepared by reacting an intermediate of formula 13 with a primary amine $R^1NH_2$ in a solvent such as water and with heating. 14 is then treated with iodine monochloride in a solvent such as methanol at around 0° C. and allowed to react for approximately overnight or less as needed for the reaction to go to completion to form 15. After completion the residue is triturated with acetone. The intermediate 15 is then reacted in a solvent, such as DMA, with ethyl acrylate in the presence of a base, such as triethylamine, and in the presence of a catalyst, such as $Pd(OAc)_2$, and (+)BINAP. The reaction is heated to approximately 100° C. and allowed to react for approximately overnight or less as needed for the reaction to go to completion to form 16. 16 is then optionally purified by column chromatography. A Compound of Formula I can then be prepared from 16 by using the same reaction conditions as described in Scheme 1 (starting at the point of the preparation of 5 from 4).

A compound of the invention where $R^1$ is optionally substituted alkyl, $R^4$ is methyl or ethyl, $R^6$ is phenyl or heteroaryl each of which is optionally substituted with 1, 2, 3, 4, or 5 $R^9$ groups (as defined in the Summary of the Invention), and $R^2$ is hydrogen can alternatively be prepared according to Scheme 4.

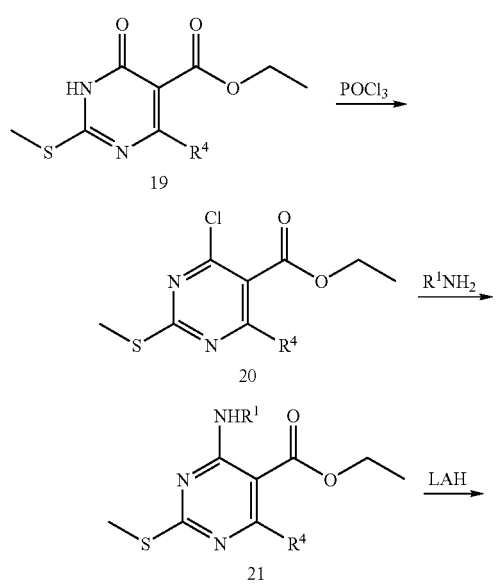

Scheme 4

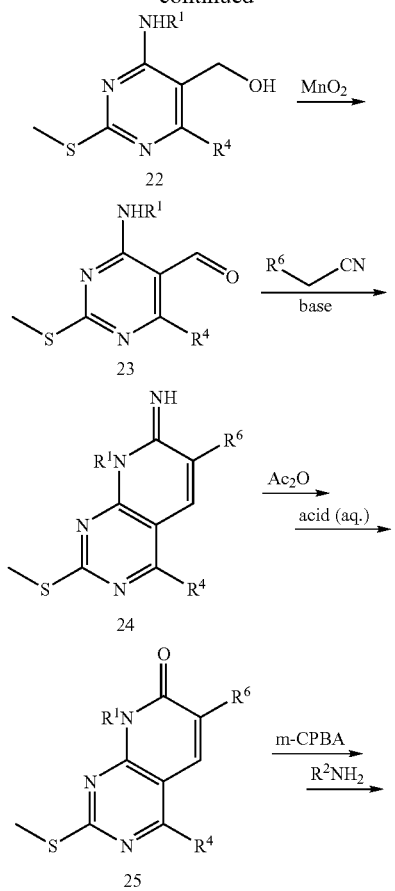

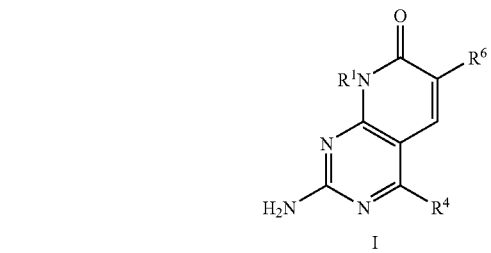

An intermediate of formula 20 is prepared by reacting an intermediate of formula 19 with neat $POCl_3$ and heating. 20 is then treated with a primary amine $R^1NH_2$ in a solvent such as water or THF and triethylamine at 0° C. to form 21. After removal of the solvent under reduced pressure, the intermediate 21 is then reacted with lithium aluminum hydride in a solvent such as THF at 0° C. After quenching and aqueous workup, solvent removal provided crystalline 22 without further purification. Treatment of 22 with manganese (II) dioxide in a solvent such as methylene chloride or chloroform at room temperature provided aldehyde 23 upon filtration and solvent removal. A Knovenegal-type condensation with 23 and an arylacetonitrile in the presence of a base such as potassium carbonate or sodium hydroxide in a protic solvent provides the cyclized imine 24. Acetylation of the imine with acetic anhydride is required prior to hydrolysis which takes place in the presence of aqueous acid and heating to afford 25. Subsequently, 25 can be oxidized to the corresponding sulfone with m-CPBA at room temperature and displaced with ammonium to provide I.

SYNTHETIC EXAMPLES

Example 1

2-amino-8-ethyl-4-methyl-6-(1H-pyrazol-5-yl)pyrido[2,3-d]pyrimidin-7(8H)-one

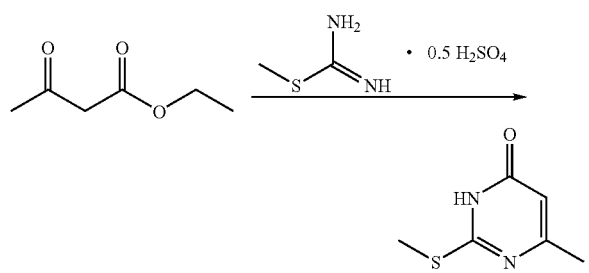

To a solution of 2-methyl-2-thiopseudourea sulfate (Aldrich, 58.74 g, 0.422 mol) in water (1000 mL) were added sodium carbonate (81.44 g, 0.768 mol) and ethyl acetoacetate (50 g, 0.384 mol) at room temperature. The reaction mixture was stirred overnight. After neutralizing to pH=8, the solid was collected through filtration followed by drying under vacuum overnight to afford 6-methyl-2-(methylthio)pyrimidin-4(3H)-one (57.2 g, 95% yield) of product. $^1$H NMR (400 MHz, DMSO-d6): δ 12.47 (bs, 1H), 5.96 (bs, 1H), 2.47 (s, 3H), 2.17 (s, 3H).

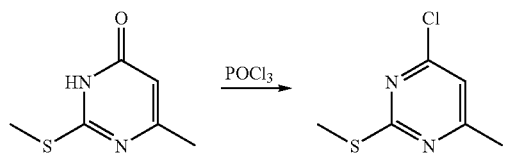

To the round bottom flask containing 6-methyl-2-(methylthio)pyrimidin-4(3H)-one (19 g, 121.6 mmol) was added POCl$_3$ (30 mL). The reaction mixture was heated to reflux for 2 h and then concentrated on a rotary evaporator to dryness. The crude 4-chloro-6-methyl-2-(methylthio)pyrimidine was used directly in the next reaction without further purification.

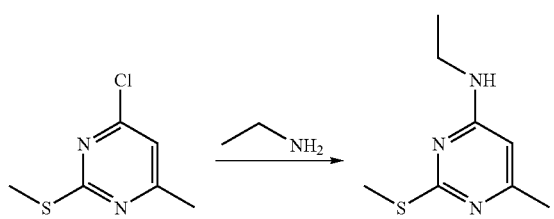

To the 4-chloro-6-methyl-2-(methylthio)pyrimidine from above was added 30 mL of a solution of 70% ethylamine in water. The reaction mixture was heated to 50° C. for 3 h. After completion, excess ethylamine was evaporated on rotary evaporator under vacuum. The solid was filtered and dried under vacuum to afford N-ethyl-6-methyl-2-(methylthio)pyrimidin-4-amine (20 g, 90% yield).

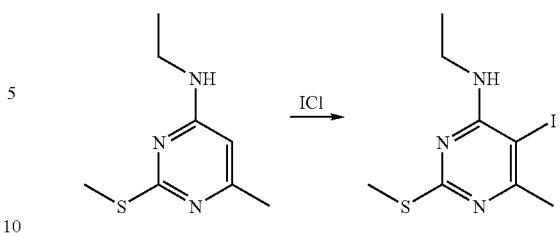

To the solution of N-ethyl-6-methyl-2-(methylthio)pyrimidin-4-amine (20 g, 121.6 mmol) in methanol was added iodine monochloride (26.58 g, 163.7 mmol) in small portions at 0° C. Then the reaction mixture was stirred overnight. After evaporation of solvent, the residue was triturated with acetone. The product N-ethyl-5-iodo-6-methyl-2-(methylthio)pyrimin-4-amine (25.2 g, 75% yield) was collected by filtration. $^1$H NMR (400 MHz, CDCl$_3$): δ 5.37 (bs, 1H), 3.52 (q, J=7.2 Hz, 1H), 2.50 (s, 3H), 1.26 (t, J=7.2 Hz, 3H).

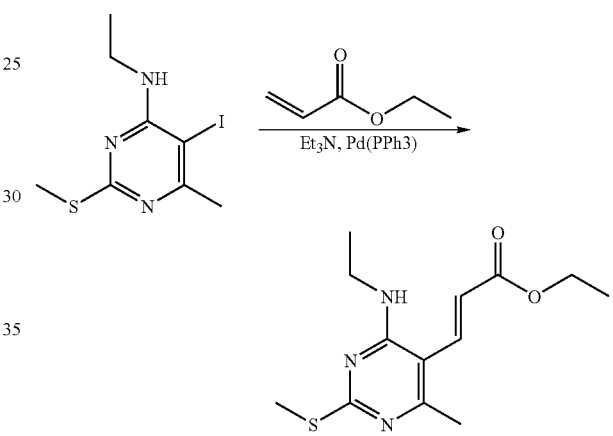

To the solution of N-ethyl-5-iodo-6-methyl-2-(methylthio)pyrimin-4-amine (25.2 g, 81.48 mmol) in DMA (260 mL) were added ethyl acrylate (12.23 g, 122.2 mmol), Pd(OAc)$_2$ (3.65 g, 16.25 mmol), (+)BINAP and triethyl amine (24.68 g, 244.4 mmol). Then the reaction mixture was heated to 100° C. and reacted overnight. After evaporation of solvent, the residue was diluted with water and the aqueous layer was extracted with ethyl acetate. The product (E)-ethyl-3-(4-(ethylamino)-6-methyl-2-(methylthio)pyrimidin-5-yl)acrylate (16.8 g, 73% yield) was isolated by silica gel column chromatography with 6-8% ethyl acetate in hexane as eluent. $^1$H NMR (400 MHz, CDCl$_3$): δ 7.65 (d, J=16.4 Hz, 1H), 6.20 (d, J=16.4 Hz, 1H), 5.15 (bs, 1H), 4.28 (q, J=7.2 Hz, 2H), 3.54 (q, J=7.2 Hz, 2H), 2.53 (s, 3H), 2.37 (s, 3H), 1.35 (t, J=7.2 Hz, 3H), 1.24 (t, J=7.2 Hz, 3H).

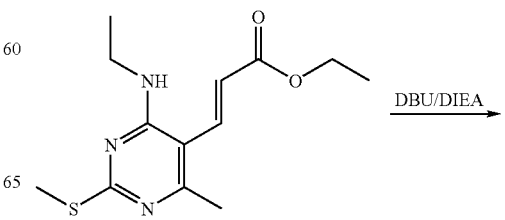

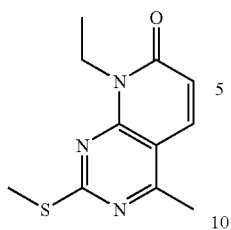

To a solution of (E)-ethyl-3-(4-(ethylamino)-6-methyl-2-(methylthio)pyrimidin-5-yl)acrylate (16.8 g, 59.8 mmol) in DIPEA was added 1,8-diazabicyclo[5.4.0]undec-7-ene (DBU, 18.21 g, 119.6 mmol) at room temperature. Then the reaction mixture was heated to reflux and reacted for 15 h. After evaporation of solvent, the residue was triturated with acetone. The product 8-ethyl-4-methyl-2-(methylthio)pyrido[2,3-d]pyrimidin-7(8H)-one (10.77 g, 77% yield) was collected by filtration. $^1$H NMR (400 MHz, CDCl$_3$): δ 7.78 (d, J=9.6 Hz, 1H), 6.63 (d, J=9.6 Hz, 1H), 4.5 (q, J=7.2 Hz, 2H), 2.67 (s, 3H), 2.62 (s, 3H), 1.33 (t, J=7.2 Hz, 3H).

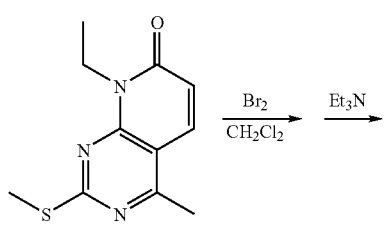

To a solution of 8-ethyl-4-methyl-2-(methylthio)pyrido[2,3-d]pyrimidin-7(8H)-one (6.31 g, 26.84 mmol) in DCM was added Br$_2$ (4.79 g, 29.52 mmol) dropwise at room temperature. Then the reaction mixture was stirred at room temperature overnight. After filtration the solid was suspended in DCM (100 mL), and triethylamine (20 mL) was added. The mixture was washed with water and dried with Na$_2$SO$_4$, and the product 6-bromo-8-ethyl-4-methyl-2-(methylthio)pyrido[2,3-d]pyrimidin-7(8H)-one (6.96 g, 83% yield) was obtained after evaporation of DCM. $^1$H NMR (400 MHz, CDCl$_3$): δ 8.22 (s, 1H), 4.56 (q, J=7.2 Hz, 2H), 2.68 (s, 3H), 2.62 (s, 3H), 1.34 (t, J=7.2 Hz, 3H).

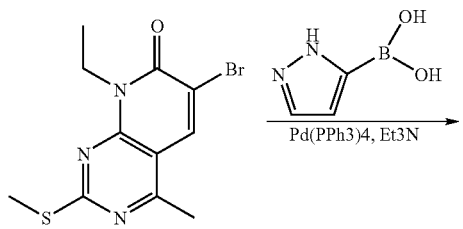

To a solution of 6-bromo-8-ethyl-4-methyl-2-(methylthio)pyrido[2,3-d]pyrimidin-7(8H)-one (0.765 g, 2.43 mmol) in DME-H$_2$O (10:1 11 mL) was added 1H-pyrazol-5-ylboronic acid (Frontier, 0.408 g, 3.65 mmol), [1,1'-bis(diphenylphosphino)ferrocene]dichloropalladium(II) complex with CH$_2$Cl$_2$ (Pd(dpppf), 0.198 g, 0.243 mmol) and triethylamine (0.736 g, 7.29 mmol) at room temperature. Then the reaction mixture was heated to reflux and reacted for 4 h. After cooling down to room temperature, the reaction mixture was partitioned with water and ethyl acetate. After separation, the organic layer was dried with Na$_2$SO$_4$, and the product 8-ethyl-4-methyl-2-(methylthio)-6-(1H-pyrazol-5-yl)pyrido[2,3-d]pyrimidin-7(8H)-one (0.567 g, 77% yield) was obtained by silica gel column chromatography. $^1$H NMR (400 MHz, CDCl$_3$): δ 13.3 (bs, 1H), 8.54 (s, 1H), 7.82-7.07 (m, 2H), 4.45 (q, J=7.2 Hz, 2H), 2.71 (s, 3H), 2.60 (s, 3H), 1.26 (t, J=7.2 Hz, 3H).

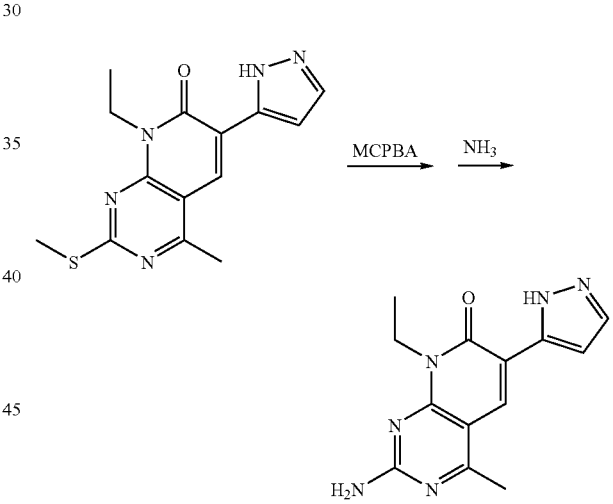

To the solution of 8-ethyl-4-methyl-2-(methylthio)-6-(1H-pyrazol-5-yl)pyrido[2,3-d]pyrimidin-7(8H)-one (0.123 g, 0.41 mmol) in DCM (2 mL) was added MCPBA (0.176 g, 77%, 0.785 mmol) in a small portion at room temperature. Then the reaction mixture was stirred for 4 h. After evaporation of DCM, dioxane (1 mL) and liquid ammonia (1 mL) were introduced. The reaction was stirred at room temperature overnight. The product 2-amino-8-ethyl-4-methyl-6-(1H-pyrazol-5-yl)pyrido[2,3-d]pyrimidin-7(8H)-one (50.4 mg) was obtained by silica gel column chromatography. $^1$H NMR (400 MHz, CD$_3$OD): δ 8.41 (s, 1H), 7.62 (d, J=2.0 Hz, 1H), 6.96 (d, J=2.0 Hz, 1H), 4.51 (q, J=7.2 Hz, 2H), 2.64 (s, 3H), 1.29 (t, J=7.2 Hz, 3H); MS (EI) for C$_{13}$H$_{14}$N$_6$O: 271.3 (MH$^+$).

Using the same or analogous synthetic techniques and substituting with appropriate reagents, the following compounds were prepared:

Example 1a 2-(amino)-8-ethyl-4-ethyl-6-(1H-pyrazol-5-yl)pyrido[2,3-d]pyrimidin-7(8H)-one: $^1$H NMR (400 MHz, DMSO-D6): δ 8.40 (s, 1H), 7.27 (bs, 1H), 7.00 (s, 1H), 4.40 (q, J=7.2 Hz, 2H), 2.95 (d, J=7.20 Hz, 2H), 1.14 (t, J=7.2 Hz, 3H), 1.08 (t, J=7.2 Hz, 3H), 0.89 (m, 1H), 0.24 (m, 2H), 0.01 (m, 2H); MS (EI) for $C_{14}H_{16}N_6O$: 285.2 (MH$^+$).

Example 1b 8-ethyl-4-methyl-2-(methylamino)-6-(1H-pyrazol-5-yl)pyrido[2,3-d]pyrimidin-7(8H)-one: $^1$H NMR (400 MHz, CH$_3$OH-d$_4$): δ 8.39 (s, 1H), 7.60 (bs, 1H), 6.93 (bs, 1H), 4.53 (bs, 12H), 3.02 (s, 3H), 2.84 (bs, 3H), 1.33 (bs, 3H); MS (EI) for $C_{14}H_{16}N_6O$: 285.3 (MH$^+$).

Example 1c

8-Ethyl-2-[(2-fluoroethyl)amino]-4-methyl-6-(1H-pyrazol-5-yl)pyrido[2,3-d]pyrimidin-7(8H)-one: $^1$H NMR (400 MHz, CH$_3$OH-d$_4$): δ 8.34 (bs, 1H), 7.25 (bs, 1H), 6.90 (bs, 1H), 4.60 (dt, J=5.2, 2.2 Hz, 2H), 4.49 (q, J=7.20 Hz, 2H), 3.78 (dt, J=5.2, 2.2 Hz, 2H), 2.64 (s, 3H), 1.30 (t, J=7.2 Hz, 3H); MS (EI) for $C_{15}H_{17}FN_6O$: 317.3 (MH$^+$).

Example 1d

2-Amino-8-cyclopentyl-4-methyl-6-(1H-pyrazol-3-yl)pyrido[2,3-d]pyrimidin-7(8H)-one: $^1$H NMR (400 MHz, DMSO-d$_6$): δ 13.10 (s, 1H), 8.42 (d, 1H), 7.70 (s, 1H), 7.20 (bs, 2H), 6.01 (m, 1H), 2.61 (s, 3H), 2.30 (m, 2H), 2.10 (m, 2H), 1.80 (m, 2H), 1.60 (m, 2H); MS (EI) for $C_{16}H_{18}N_6O$: 311.8 (M+H).

Intermediate 1

Alternate route to (E)-ethyl-3-(4-(ethylamino)-6-methyl-2-(methylthio)pyrimidin-5-yl)acrylate

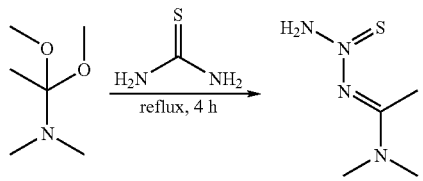

N,N-Dimethyl acetamide dimethyl acetal (75 g, 0.56 mole) was added to a suspension of thiourea (33.0 g, 0.43 mole) in methylene chloride. The mixture was heated under reflux for 4 h. The solvent was removed and the residue was crystallized from 5% MeOH and diethyl ether affording (1E)-N'-(aminocarbonothioyl)-N,N-dimethylethanimidamide (47.8 g, 76% yield).

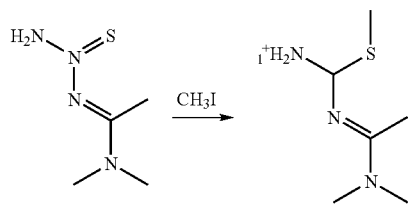

A suspension of (1E)-N'-(aminocarbonothioyl)-N,N-dimethylethanimidamide (47.8 g, 0.33 mole) in methyl iodide (150 mL) and THF (350 mL) was stirred for 18 h at room temperature. The mixture was evaporated under reduced pressure. After addition of 5% MeOH and diethyl ether, the compound precipitated and was collected by filtration affording (1E)-N'-[amino(methylthio)methyl]-N,N-dimethylethanimidamide hydrogen iodide salt (91.0 g, 96% yield).

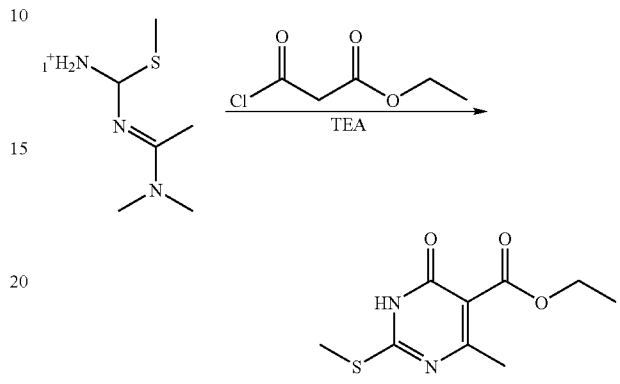

To a solution of (1E)-N'-[amino(methylthio)methyl]-N,N-dimethylethanimidamide hydrogen iodide salt (73.0 g, 0.26 mole) in dry dichloromethane (900 mL), was added ethyl 3-chloro-3-oxopropanoate (44 mL, 95% Lancaster, 0.34 mole) was added under a nitrogen atmosphere. The mixture was stirred for 4 h at room temperature, cooled to 0° C. then triethylamine (107 mL, 0.78 mole) was added. The reaction mixture was stirred overnight. The solvent was removed and H$_2$O was added. The pH was adjusted to pH=5.0 with acetic acid and extracted with ethylacetate then evaporated and crystallized from the appropriate solvent (Ethylacetate-Hexanes mixture solvent, approximately 20% ethylacetate-Hexanes). This afforded ethyl 4-methyl-2-(methylthio)-6-oxo-1,6-dihydropyrimidine-5-carboxylate (36.5 g, 62% yield) after drying under vacuum.

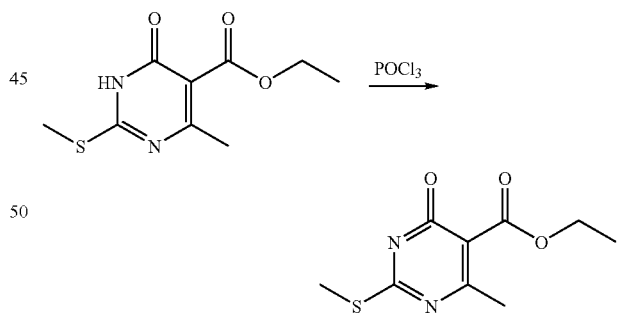

A solution of ethyl 4-methyl-2-(methylthio)-6-oxo-1,6-dihydropyrimidine-5-carboxylate (60 g, 0.26 mole) and phosphorous oxychloride (POCl$_3$, 320 mL) was heated under reflux for 4 to 5 h (monitor reaction by TLC using 30% ethylacetate and hexanes). After completion of reaction, phosphorous oxychloride was removed on a rotary evaporator. The residue was poured on to ice water and extracted with ethylacetate several times. The combined organic layers were evaporated, on a rotary evaporator, to give crude ethyl 4-chloro-6-methyl-2-(methylthio)pyrimidine-5-carboxylate (65 g). This compound was used without purification.

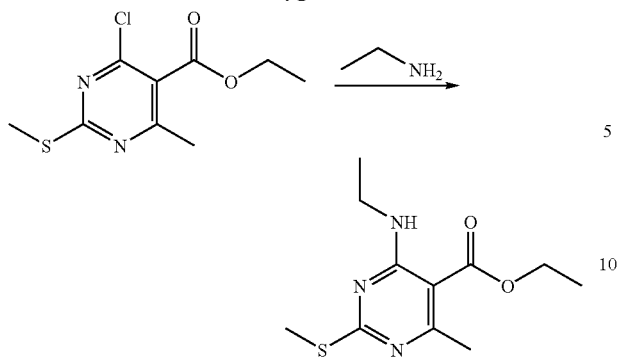

To a solution of ethyl 4-chloro-6-methyl-2-(methylthio)pyrimidine-5-carboxylate (65 g) in THF (1000 mL) and triethylamine (110 mL, 0.81 mole) was added ethylamine (2.0 M in THF, 0.81 mole) at 0° C. This reaction mixture was stirred at room temperature overnight and then solvents were removed on a rotary evaporator. $H_2O$ was added and the mixture extracted with ethyl acetate several times. Solvents from the combined organic layers were removed on a rotary evaporator affording 58 g (86% yield) of ethyl 4-(ethylamino)-6-methyl-2-(methylthio)pyrimidine-5-carboxylate. This material was used as such without further purification.

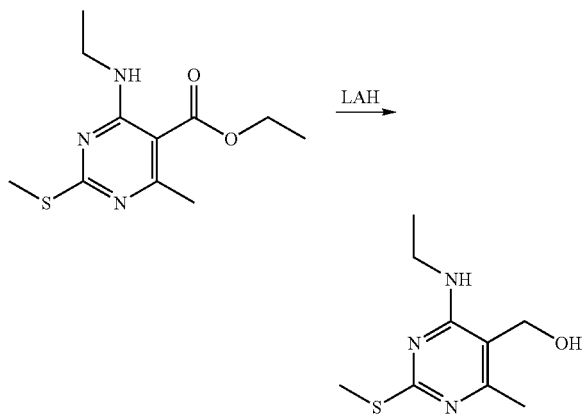

To a lithium aluminum hydride solution (LAH, 1.0 M solution in THF, Aldrich, 450 mL) was added a solution of ethyl 4-(ethylamino)-6-methyl-2-(methylthio)pyrimidine-5-carboxylate (57 g) in THF (1000 mL). The reaction mixture was stirred overnight. After cooling to 0° C., the reaction mixture was cautiously quenched with a 1:9 mixture of $H_2O$/THF until gas evolution has ceased, then diluted with $H_2O$ (500 mL) and stirred well for 2 h. The resulting slurry was extracted with ethylacetate several times. The aqueous layer was then filtered through Celite and washed with ethylacetate again. The combined organic layers were washed with brine, dried and concentrated under reduced pressure to give 41.0 g (85% yield) of [4-(ethylamino)-6-methyl-2-(methylthio)pyrimidin-5-yl]methanol as a light yellow crystal, which was used without purification in the next step.

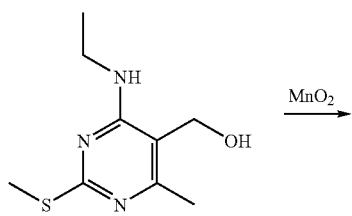

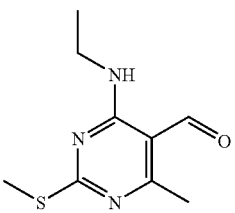

To a solution of [4-(ethylamino)-6-methyl-2-(methylthio)pyrimidin-5-yl]methanol (41.0 g) in chloroform (4000 mL) was added manganese oxide (125 g, 1.4 mole) and stirred for 4 h at room temperature. More manganese oxide was added until the disappearance of alcohol compound was observed. The reaction mixture was filtered through Celite and washed with some chloroform and evaporated all organic solvents to give 38 g (92% yield) of 4-(ethylamino)-6-methyl-2-(methylthio)pyrimidine-5-carbaldehyde as a colorless solid, which was used without purification in the next step.

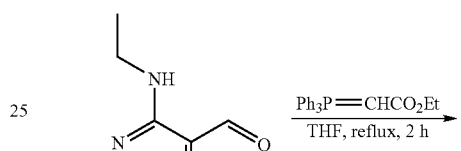

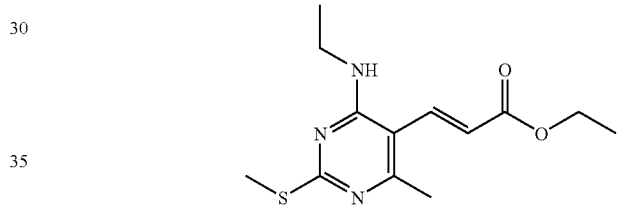

To a solution of 4-(ethylamino)-6-methyl-2-(methylthio)pyrimidine-5-carbaldehyde (38 g, 180 mmol) in THF (500 mL) was added (Carbethoxymethylene) triphenylphosphorane (95%, Aldrich, 85.18 g, 244 mmol). The reaction mixture was heated to reflux for 1.5 h and was monitored by TLC (4:1 hexanes/ethylacetate). The reaction was cooled to room temperature and was concentrated on a rotary evaporator. It was directly subjected to column chromatography (4:1 hexanes/ethylacetate) to give (E)-ethyl-3-(4-(ethylamino)-6-methyl-2-(methylthio)pyrimidin-5-yl)acrylate as a white crystal, 46.14 g (91% yield).

Example 2

2-Amino-6-bromo-8-ethyl-4-methylpyrido[2,3-d]pyrimidin-7(8H)-one

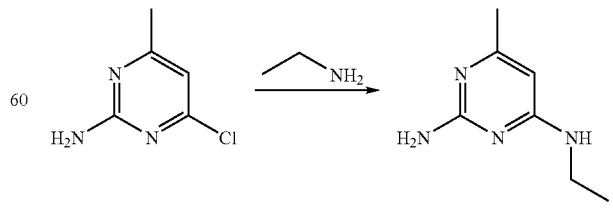

To a 3-necked 3-L flask, that was equipped with an overhead stirrer, was added in order 2-amino-4-chloro-6-methylpyrimidine (Aldrich, 100 g, 0.696 mol, 1 equiv.), ethylamine (70% ethylamine in water, Lancaster, 625 mL), 625 mL H$_2$O, and 125 mL TEA (0.889 mol, 1.28 equiv.). The mixture was stirred and heated at reflux for 20 h, during which time the reaction turned homogeneous. The reaction was allowed to cool to room temperature. The volatile ethylamine was removed on a rotary evaporator. A precipitate formed. The aqueous mixture containing the precipitate was allowed to stand at room temperature for 2 h and then filtered. After drying under vacuum, 106 g (100% yield) of 2-amino-6-ethylaminopyrimidine was obtained as a colorless solid. This material was used as such in the following reaction.

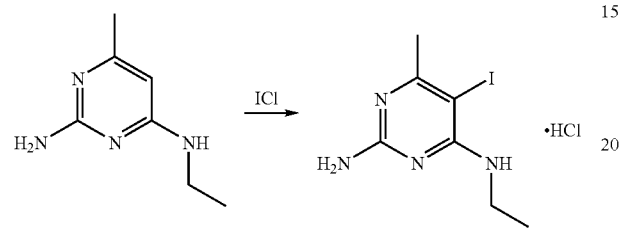

To a solution of 2-amino-6-ethylaminopyrimidine (98 g, 0.64 mol) in methanol (1.6 L) was added ICl (115.0 g, 0.71 mol) in a small portion at 15° C. Then the reaction mixture was stirred at room temperature for 3 h (monitored by LC/MS). After evaporation of solvent by rotary evaporator, the residue was triturated with acetone. 2-amino-6-ethylamino-4-iodopyrimidine hydrochloride (188.5 g, 93% isolated yield) was obtained by vacuum filtration and drying. $^1$H NMR (400 MHz, CD$_3$OD) δ 3.58 (q, 2H), 2.14 (s, 3H), 1.11 (t, 3H); MS (EI) for C$_7$H$_{11}$N$_4$ClI: 279.1 (MH$^+$).

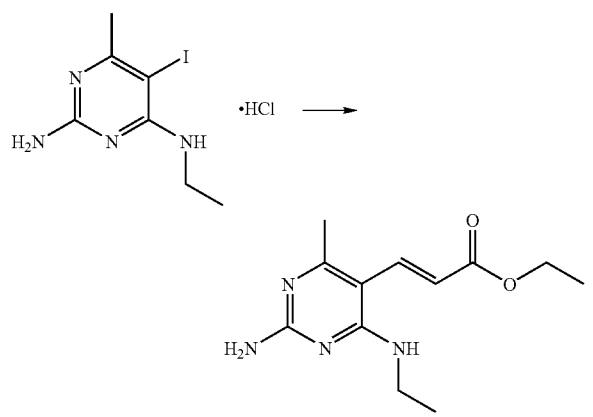

To a three-neck round bottom flask equipped with overhead mechanic stirrer were added 2-amino-6-ethylamino-4-iodopyrimidine hydrochloride (188.5 g, 0.60 mol), ethyl acrylate (221 mL, 2.0 mol), triethylamine (285 mL, 2.0 mol), DMF (1.3 L), and tetrakis(triphenylphosphine)palladium(0) (Pd(PPh$_3$)$_4$, 31.3 g, 0.027 mol). The reaction mixture was heated to 95° C. and stirred for 3 h (monitored by LC/MC). After reaction completion, the reaction mixture was evaporated about to 1/10 of original volume and partitioned with 500 mL of ethyl acetate and 1000 mL of water. The aqueous layer was extracted with ethyl acetate 5 times. (E)-Ethyl 3-(2-amino-4-(ethylamino)-6-methylpyrimidin-5-yl)acrylate (100 g, 67% yield) was obtained by recrystallization from acetone after evaporation of ethyl acetate. $^1$H NMR (400 MHz, CD$_3$OD) δ 7.48 (dd, J1=16.0 Hz, J2=4.0 Hz, 1H), 6.20 (dd, J1=16 Hz, J2=4 Hz, 1H), 4.25 (q, J=7.2 Hz, 2H), 3.51 (q, J=7.6 Hz, 2H), 2.39 (s, 3H), 1.3 (t, J=7.2 Hz, 3H), 1.2 (t, J=7.6 Hz, 3H). MS (EI) for C$_{12}$H$_{18}$N$_4$O$_2$: 251.3 (MH$^+$).

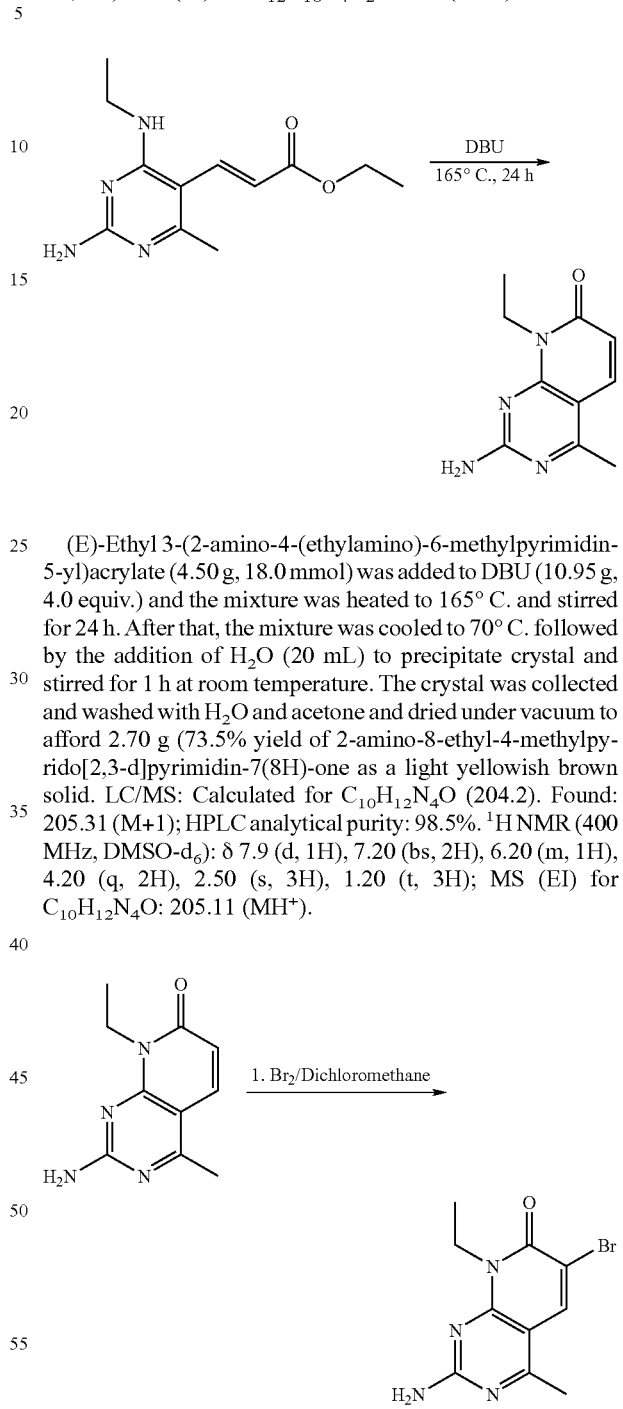

(E)-Ethyl 3-(2-amino-4-(ethylamino)-6-methylpyrimidin-5-yl)acrylate (4.50 g, 18.0 mmol) was added to DBU (10.95 g, 4.0 equiv.) and the mixture was heated to 165° C. and stirred for 24 h. After that, the mixture was cooled to 70° C. followed by the addition of H$_2$O (20 mL) to precipitate crystal and stirred for 1 h at room temperature. The crystal was collected and washed with H$_2$O and acetone and dried under vacuum to afford 2.70 g (73.5% yield of 2-amino-8-ethyl-4-methylpyrido[2,3-d]pyrimidin-7(8H)-one as a light yellowish brown solid. LC/MS: Calculated for C$_{10}$H$_{12}$N$_4$O (204.2). Found: 205.31 (M+1); HPLC analytical purity: 98.5%. $^1$H NMR (400 MHz, DMSO-d$_6$): δ 7.9 (d, 1H), 7.20 (bs, 2H), 6.20 (m, 1H), 4.20 (q, 2H), 2.50 (s, 3H), 1.20 (t, 3H); MS (EI) for C$_{10}$H$_{12}$N$_4$O: 205.11 (MH$^+$).

2-Amino-8-ethyl-4-methylpyrido[2,3-d]pyrimidin-7 (8H)-one (2.70 g, 13.2 mmol) was added to dichloromethane (100 mL), and then bromine (0.75 mL, 1.10 equiv.) was added slowly. This reaction mixture was stirred for 3 h at room temperature. After that, the solvent was evaporated nearly 80% volume of reaction mixture under vacuum, and then acetone was added to give 3.54 g 2-Amino-6-bromo-8-ethyl-4-methylpyrido[2,3-d]pyrimidin-7(8H)-one as a tan solid.

LC/MS: Calculated for $C_{10}H_{11}BrN_4O$ (283.12). Found: 285.15 (M+2). HPLC analytical purity: 97.7%.

Example 3

2-Amino-4-methyl-8-(methylethyl)-6-(1H-pyrazol-3-yl)pyrido[2,3-d]pyrimidin-7(8H)-one

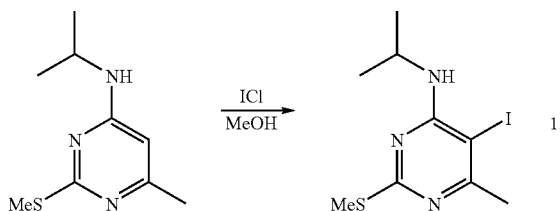

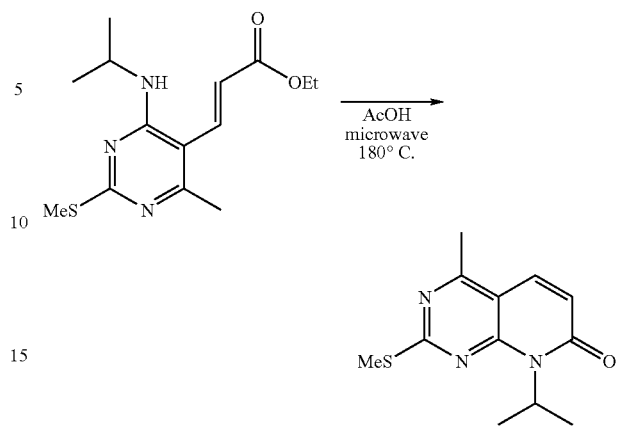

To a crude solution of N-isopropyl-6-methyl-2-(methylthio)pyrimidin-4-amine (44.6 g, 224 mmol), prepared using analogous procedures as described in Example 1, in 400 mL of methanol was added ICl (40.0 g, 246 mmol) in small portions at room temperature. The reaction mixture was then stirred at for 3 h monitoring by LC/MS. After evaporation of solvent by rotary evaporator, the residue was triturated with acetone to yield 5-iodo-N-isopropyl-6-methyl-2-(methylthio)pyrimidin-4-amine. $^1$H NMR (400 MHz, CDCl$_3$) δ 6.37 (br m, 1H), 4.47 (m, 1H), 2.78 (s, 3H), 2.67 (s, 3H), 1.41 (d, J=6.4, 6H).

(E)-Ethyl 3-(4-(isopropylamino)-6-methyl-2-(methylthio)pyrimidin-5-yl)acrylate (2.5 g, 8.46 mmol) was dissolved in acetic acid by gentle warming. Sample was placed in microwave reactor for 6 h at 180° C., 300 W, and 200 PSI. The product was purified by silica gel column chromatography eluting with 20% ethyl acetate/hexane. Desired fractions were combined and reduced into 8-isopropyl-4-methyl-2-(methylthio)pyrido[2,3-d]pyrimidin-7(8H)-one as a yellow powder (1.20 g, 57% yield) which was then dried under heavy vacuum overnight. $^1$H NMR (400 MHz, CDCl$_3$) δ 7.74 (d, J=9.6, 1H), 6.58 (d, J=9.6, 1H), 5.84 (br s, 1H), 2.65 (s, 3H), 2.63 (s, 3H), 1.63 (d, J=6.8, 6H).

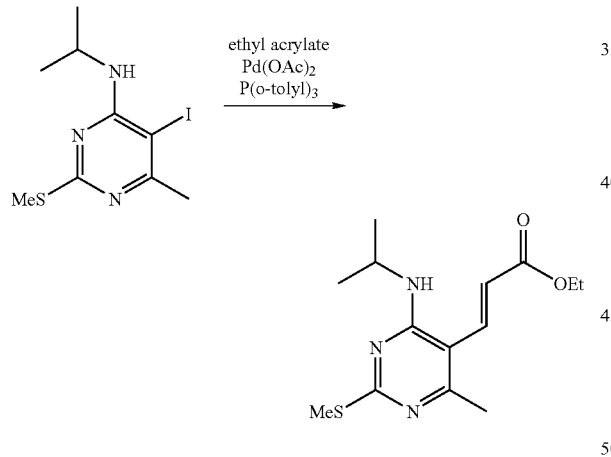

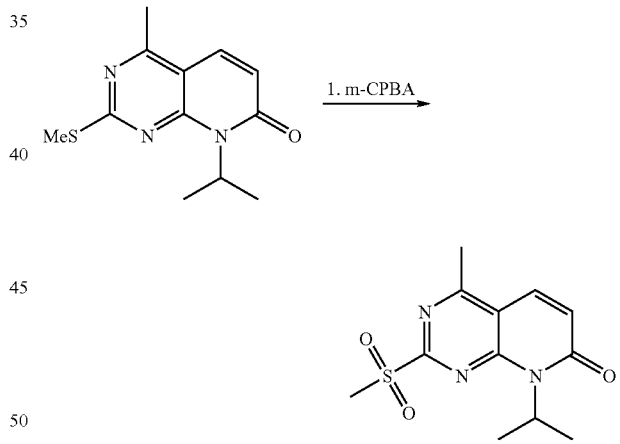

5-Iodo-N-isopropyl-6-methyl-2-(methylthio)pyrimidin-4-amine (8.1 g, 26.2 mmol), ethyl acrylate (5.24 g, 52.4 mmol), triethylamine (10.6 g, 105 mmol), palladium (II) acetate (1.17 g, 5.23 mmol), and tri-o-tolyl phosphine (1.59 g, 5.23 mmol) were added in that order to 10.8 mL of DMA in a pressure tube and sealed. The reaction mixture was heated to 100° C. and allowed to stir overnight. The reaction was quenched by filtration through a short silica plug washing with ACN. The solvent was evaporated and diluted with ethyl acetate then extracted with 10% aqueous LiCl, followed by water and brine. NOTE: Extraction is necessary to remove all DMA giving resolution in chromatography. The sample was purified by silica gel column chromatography using 20% ethyl acetate/hexane as eluent. Desired fractions were combined and reduced to afford 2.5 g (34% yield) of ethyl (2E)-3-[4-(isopropylamino)-6-methyl-2-(methylthio)pyrimidin-5-yl]acrylate as a yellow/orange oil.

8-Isopropyl-4-methyl-2-(methylthio)pyrido[2,3-d]pyrimidin-7(8H)-one (5.38 g, 21.59 mmol) was dissolved in 100 mL DCM. To the stirring solution, m-CPBA (13.97 g, 64.78 mmol) was added. The reaction was allowed to stir for 2.5 h at room temperature. LCMS indicated reaction had gone to completion. Sample was diluted with 300 mL of DCM and 300 mL K$_2$CO$_3$, upon addition of base a white precipitate formed that dissolved in excess H$_2$O. Organic layer was extracted further with H$_2$O and brine, and then dried over Na$_2$CO$_3$. The solvent was evaporated to afford the product 8-isopropyl-4-methyl-2-(methylsulfonyl)pyrido[2,3-d]pyrimidin-7(8H)-one (6.0 g, 99% yield) as a light yellow oil that was used immediately in the next reaction.

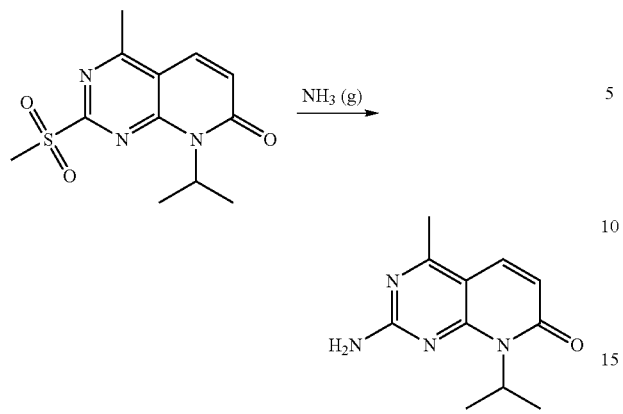

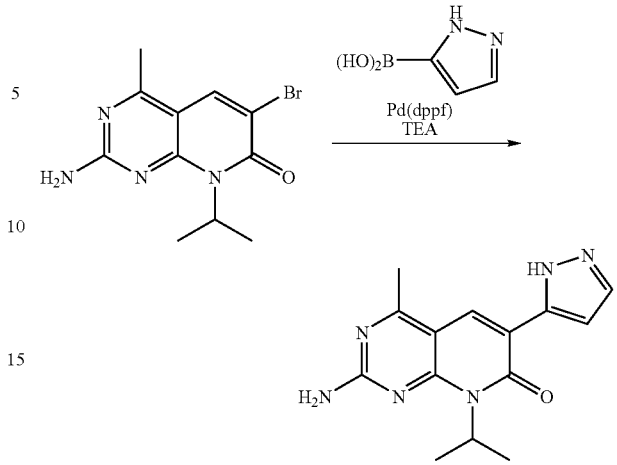

8-isopropyl-4-methyl-2-(methylsulfonyl)pyrido[2,3-d]pyrimidin-7(8H)-one (approximately 3.0 g) was dissolved in 50 mL THF, in a 350 mL pressure tube. While stirring, NH₃ (g) was bubbled in through solution for 1.5 minutes. A color change was observed form light yellow to olive green in about 120 seconds. The tube was sealed and stirred at room temperature overnight. A precipitate had formed. The reaction mixture, including precipitate, was reduced to near dryness, filtered and washed with a minimal volume of cold THF, affording 2.88 g of 2-amino-8-isopropyl-4-methylpyrido[2,3-d]pyrimidin-7(8H)-one.

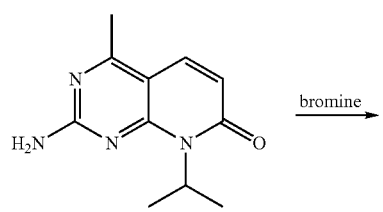

In a 350 mL pressure tube 2-amino-6-bromo-8-isopropyl-4-methylpyrido[2,3-d]pyrimidin-7(8H)-one (1.50 g, 5.05 mmol), 1H-pyrazol-3-yl boronic acid (1.12 g, 10.09 mmol), $K_2CO_3$ (336 mg, 15.1 mmol), and tetrakis(triphenylphosphine) palladium (0) (583 mg, 0.0504 mmol) were dissolved in 50 mL dioxane and 5 mL $H_2O$. The tube was sealed, heated to 100° C. and allowed to react overnight. A color change was observed. LCMS indicated no presence of starting material. Sample was filtered through a syringe filter and evaporated to dryness. Compound was dissolved in ethyl acetate and triturated in hexane. Light yellow powder of 2-amino-8-isopropyl-4-methyl-6-(1H-pyrazol-5-yl)pyrido[2,3-d]pyrimidin-7(8H)-one (195 mg, 13.7% yield) was found to be 98% pure by HPLC. ¹H NMR (400 MHz, CDCl₃) δ 12.97 (br s, 1H), 8.35 (s, 1H), 7.60 (br s, 1H), 7.21 (s, 2H), 6.94 (s, 1H), 5.86 (br s, 1H), 2.50 (m, 6H), 1.54 (s, 3H), MS (EI) for $C_{14}H_{16}N_6O$: 285.0 (MH⁺).

Example 4

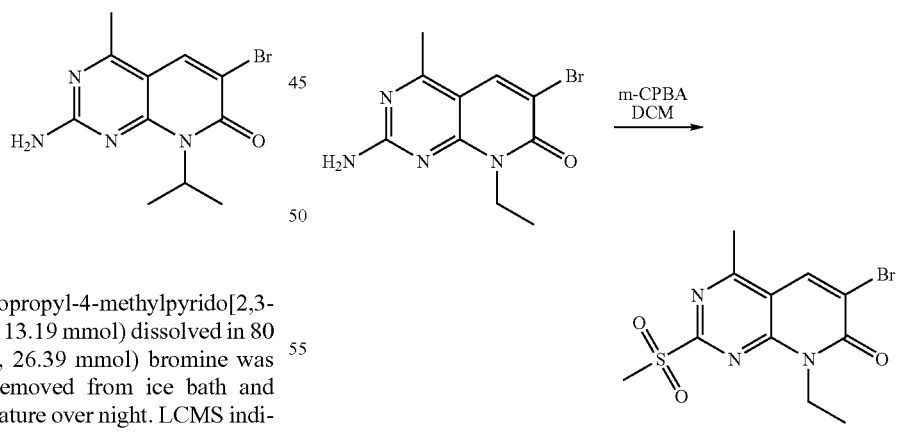

To a solution of 2-amino-8-isopropyl-4-methylpyrido[2,3-d]pyrimidin-7(8H)-one (2.88 g, 13.19 mmol) dissolved in 80 mL of DCM at 0° C., (4.21 g, 26.39 mmol) bromine was added. Reaction vessel was removed from ice bath and allowed to react at room temperature over night. LCMS indicated complete conversion of starting material to product. Sample was evaporated to remove DCM and excess bromine. Orange solid was diluted in ethyl acetate and extracted with 10% NaHSO₃, H₂O, and brine. Organic layer was dried over Na₂SO₄, filtered, and reduced to dryness yielding 2-amino-6-bromo-8-isopropyl-4-methylpyrido[2,3-d]pyrimidin-7(8H)-one as a light yellow powder (2.2 g, 56% yield). ¹H NMR (400 MHz, CDCl₃) δ 8.08 (s, 1H), 5.83 (m, 1H), 5.69 (br s, 2H), 2.60 (s, 3H), 1.58 (d, J=6.8, 6H).

3-Chloroperbenzoic acid (0.565 g, 3.27 mmol) was added to a solution of 6-bromo-8-ethyl-4-methyl-2-(methylthio)pyrido[2,3-d]pyrimidin-7(8H)-one (0.308 g, 0.980 mmol) in dichloromethane (5.0 mL) at room temperature. After 30 minutes, the reaction was diluted with dichloromethane (50 mL) and washed twice with saturated NaHCO₃, followed by brine. The organic phase was separated and dried over Na₂SO₄, filtered, and concentrated in vacuo. The residue was precipitated with ethyl acetate to provide 8-ethyl-4-methyl-2-(methylsulfonyl)pyrido[2,3-d]pyrimidin-7(8H)-one (302 mg, 89% yield) as a yellow solid.

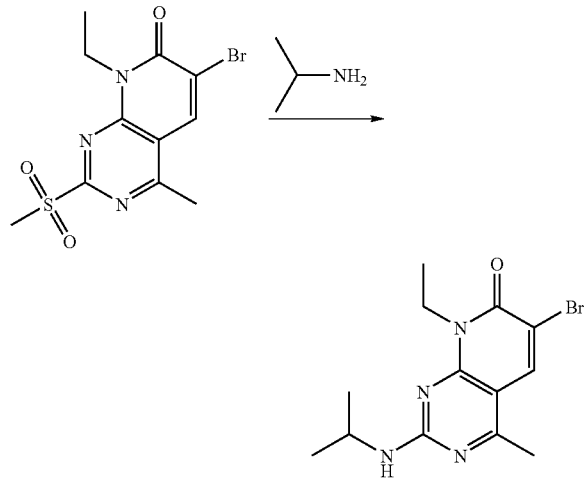

To a stirred solution of (76.5 mg, 0.221 mmol) in 1.5 mL of $CH_2Cl_2$ was added isopropyl amine (709.9 mg, 12.0 mmol, 54 eq.) The reaction was stirred for 15 h at room temperature. The reaction was diluted with $CH_2Cl_2$ and extracted with 2N NaOH, $H_2O$, and brine. The organic layer was dried over $Na_2SO_4$, filtered and concentrated. The crude material was purified using preparative HPLC. Lyophilization of the product containing fractions afforded 19.9 mg (27.6% yield) of 6-bromo-8-ethyl-2-(isopropylamino)-4-methylpyrido[2,3-d]pyrimidin-7(8H)-one: $^1$H NMR (400 MHz, CDCl$_3$): δ 8.08 (s, 1H), 5.30 (bs, 1H), 4.48 (bd, 2H), 4.18 (bs, 1H), 2.52 (s, 3H), 1.62 (bs, 3H), 1.29 (m, 9H), MS (EI) for $C_{13}H_{17}BrN_4O$: 325.2 (MH$^+$).

Using the same or analogous synthetic techniques and substituting with appropriate reagents, the following compounds were prepared:

Example 4b 6-bromo-2-(tert-butylamino)-8-ethyl-4-methylpyrido[2,3-d]pyrimidin-7(8H)-one: $^1$H NMR (400 MHz, CDCl$_3$): δ 8.08 (s, 1H), 5.47 (bs, 1H), 4.48 (m, 2H), 2.50 (s, 3H), 1.58 (bs, 3H), 1.49 (s, 9H), MS (EI) for $C_{14}H_{19}BrN_4O$: 339.2 (MH$^+$)

Example 4c

6-Bromo-2-(cyclopentylamino)-8-ethyl-4-methylpyrido[2,3-d]pyrimidin-7(8H)-one: $^1$H NMR (400 MHz, CDCl$_3$): δ 8.07 (s, 1H), 5.89 (bs, 1H), 4.49 (bd, 2H), 2.51 (s, 3H), 2.07 (m, 2H), 1.71 (m, 2H), 1.58 (m, 2H), 1.31 (t, 3H), MS (EI) for $C_{15}H_{19}BrN_4O$: 351.2 (MH$^+$)

Example 4d

6-Bromo-2-(cyclohexylamino)-8-ethyl-4-methylpyrido[2,3-d]pyrimidin-7(8H)-one: $^1$H NMR (400 MHz, CDCl$_3$): δ 8.07 (s, 1H), 5.41 (bs, 1H), 4.47 (bd, 2H), 3.84 (bs, 1H), 2.51 (s, 3H), 2.05 (d, J=12.4 Hz, 2H), 1.77 (m, 2H), 1.64 (br m, 4H), 1.39 (m, 2H), 1.30 (m, 3H), MS (EI) for $C_{16}H_{21}BrN_4O$: 365.2 (MH$^+$)

Example 4e

6-Bromo-8-ethyl-4-methyl-2-(2-morpholinoethylamino)pyrido[2,3-d]pyrimidin-7(8H)-one: $^1$H NMR (400 MHz, CDCl$_3$): δ 8.08 (s, 1H), 6.22 (bs, 1H), 4.48 (q, J=6.4 Hz, 2H), 3.74 (t, J=4.4 Hz, 1H), 3.57 (q, J=4.8 Hz, 3H), 2.98 (bs, 2H), 2.63 (t, J=6.0 Hz, 2H), 2.53 (s, 3H), 1.30 (t, J=6.8 Hz, 2H), MS (EI) for $C_{16}H_{22}BrN_5O$: 396.2 (MH$^+$)

Example 4f

6-Bromo-8-ethyl-4-methyl-2-[(3-morpholino-4-ylpropyl)amino]pyrido[2,3-d]pyrimidin-7(8H)-one: $^1$H NMR (400 MHz, CDCl$_3$): δ 8.07 (s, 1H), 6.23 (bs, 1H), 4.47 (bs, 1H), 3.75 (m, 4H), 3.57 (m, 2H), 2.52 (m, 4H), 2.48 (m, 2H), 1.82 (m, 2H), 1.28 (s, 3H), MS (EI) for $C_{17}H_{24}BrN_5O$: 410.2 (MH$^+$)

Example 4g

6-Bromo-2-{[3-(dimethylamino)propyl]amino}-8-ethyl-4-methylpyrido[2,3-d]pyrimidin-7(8H)-one: $^1$H NMR (400 MHz, CDCl$_3$): δ 8.08 (s, 1H), 7.26 (bs, 1H), 4.47 (m, 2H), 3.54 (m, 2H), 2.78 (t, J=7.6 Hz, 2H), 2.52 (s, 3H), 2.50 (s, 3H), 2.04 (s, 3H), 2.00 (m, 2H), 1.29 (t, J=7.2 Hz, 3H), MS (EI) for $C_{15}H_{22}BrN_5O$: 369.2 (MH$^+$)

Example 4h

8-Ethyl-2-(ethylamino)-4-methylpyrido[2,3-d]pyrimidin-7(8H)-one: $^1$H NMR (400 MHz, CDCl$_3$): δ 7.67 (d, J=9.2 Hz, 1H), 6.39 (d, J=9.2 Hz, 1H), 5.31 (bs, 1H), 2.54 (s, 3H), 4.32 (q, J=6.8 Hz, 2H), 3.52 (q, J=6.8 Hz, 2H), 2.53 (s, 3H), 1.15 (m, 6H); MS (EI) for $C_{12}H_{16}N_4O$: 233.2 (MH$^+$).

Example 4j

6-Bromo-2-{[2-(dimethylamino)ethyl]amino}-8-ethyl-4-methylpyrido[2,3-d]pyrimidin-7(8H)-one: $^1$H NMR (400 MHz, DMSO-d$_6$): δ 8.37 (s, 1H), 7.83 (bt, J=8.0 Hz, 1H), 4.34 (q, J=8.0 Hz, 2H), 3.42 (q, J=4.0 Hz, 2H), 2.51 (s, 3H), 2.45 (t, J=4.0 Hz, 2H), 1.83 (s, 6H), 1.20 (t, J=8.0 Hz, 3H); MS (EI) for $C_{14}H_{20}BrN_5O$: 354.3 (M$^+$).

Example 4k 6-bromo-2-(ethylamino)-4-methyl-8-(1-methylethyl)pyrido[2,3-d]pyrimidin-7(8H)-one: $^1$H NMR (400 MHz, CDCl$_3$): δ 8.04 (s, 1H), 6.66 (bs, 1H), 5.83 (sept, J=6.8 Hz, 1H), 3.54 (dq, J=12.8, 7.6 Hz, 2H), 2.62 (s, 3H), 1.60 (d, J=6.8 Hz, 6H), 1.34 (t, J=7.2 Hz, 3H); MS (EI) for $C_{13}H_7BrN_4O$: 324.9 (M).

Example 4m

6-Bromo-8-ethyl-4-methyl-2-morpholiN-4-ylpyrido[2,3-d]pyrimidin-7(8H)-one: $^1$H NMR (400 MHz, CDCl$_3$): δ 8.09 (s, 1H), 4.45 (q, J=6.8 Hz, 2H), 3.92 (s, 3H), 3.79 (s, 3H), 2.55 (s, 3H), 1.30 (t, J=6.8 Hz, 3H); MS (EI) for $C_{14}H_{17}BrN_4O_2$: 355.1 (M2H$^+$).

Example 4n

6-Bromo-8-ethyl-4-methyl-2-[(phenylmethyl)amino]pyrido[2,3-d]pyrimidin 7(8H)-one: $^1$H NMR (400 MHz, CDCl$_3$): δ 8.09 (s, 1H), 7.32 (m, 5H), 5.86 ((bs, 1H), 4.68 (s, 2H), 4.43 (q, J=7.2 Hz, 2H), 2.54 (s, 3H), 1.13 (t, J=7.2 Hz, 3H); MS (EI) for $C_{17}H_{17}BrN_4O$: 375.1 (M2H$^+$). Example 4p. 6-Bromo-8-ethyl-2-(ethylamino)-4-methylpyrido[2,3-d]pyrimidin-7(8H)-one: $^1$H NMR (400 MHz, CDCl$_3$): δ 8.09 (s, 1H), 5.71 (bs, 1H), 4.48 (bs, 2H), 3.54 (q, J=6.8 Hz, 2H), 2.53 (s, 3H), 1.16 (m, 6H); MS (EI) for $C_{12}H_{15}BrN_4O$: 311.9 (MH$^+$).

Example 5

2-(Ethylamino)-4-methyl-8-(1-methylethyl)-6-(2-thienyl)pyrido[2,3-a]pyrimidin-7(8H)-one

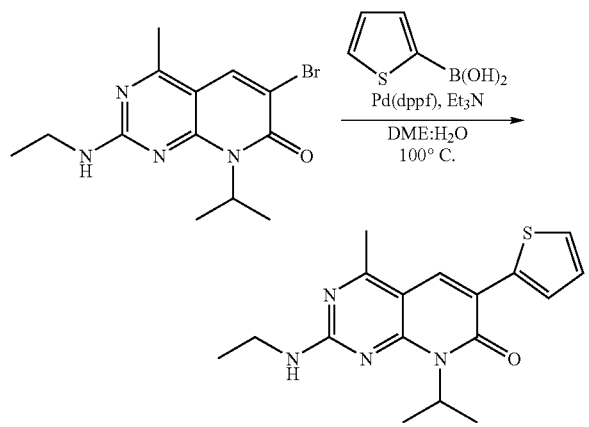

Pd(dppf) dichloromethane adduct (0.077 g, 0.095 mmol) was added to a suspension of 6-bromo-2-(ethylamino)-4-methyl-8-(1-methylethyl)pyrido[2,3-d]pyrimidin-7(8H)-one (0.154 g, 0.474 mmol), 2-thiophene boronic acid (0.079 g, 0.616 mmol), and triethylamine (165 µL, 1.19 mmol) in 10:1 DME:water (1.5 mL). The reaction was heated to 100° C. After 5 h, the reaction was cooled to room temperature, filtered though a Celite plug and concentrated in vacuo. The residue was purified on SiO$_2$ (3:2 hexanes:ethyl acetate) to give 2-(ethylamino)-4-methyl-8-(1-methylethyl)-6-(2-thienyl)pyrido[2,3-d]pyrimidin-7(8H)-one (28 mg, 18% yield) as a light yellow solid: $^1$H NMR (400 MHz, CDCl$_3$): δ 8.06 (s, 1H), 7.60 (dd, J=4.0, 1.2 Hz, 1H), 7.38 (dd, J=5.2, 0.8 Hz, 1H), 7.10 (dd, J=4.8, 3.2 Hz, 1H), 5.93 (bsept, 1H), 5.13 (bs, 1H), 3.54 (pent, J=7.2 Hz, 2H), 2.61 (s, 3H), 1.66 (d, J=6.8 Hz, 6H), 1.28 (t, J=7.6 Hz, 3H); MS (EI) for $C_{17}H_{20}N_4OS$: 329.0

Using the same or analogous synthetic techniques and substituting with appropriate reagents, the following compounds were prepared:

Example 5a 2-(Ethylamino)-6-furan-2-yl-4-methyl-8-(1-methylethyl)pyrido[2,3-d]pyrimidin-7(8H)-one: $^1$H NMR (400 MHZ, CDCL$_3$): δ 8.43 (S, 1H), 7.81 (S, 1H), 7.47 (T, J=2 HZ, 1H), 6.75 (DD, J-2.0, 0.8 HZ, 1H), 5.92 (BSEPT, 1H), 5.25 (BS, 1H), 3.53 (DQ, J=12.5, 7.6 HZ, 2H), 2.60 (S, 3H), 1.65 (D, J=6.8 HZ, 6H), 1.29 (T, J=7.2 HZ, 3H); MS (EI) FOR $C_{17}H_{20}N_4O_2$: 313.1 (MH$^+$).

Example 5b 2-(Ethylamino)-4-methyl-8-(1-methylethyl)-6-(1H-pyrazol-3-yl)pyrido[2,3-d]pyrimidin-7(8H)-one: $^1$H NMR (400 MHz, CDCl$_3$): δ 8.08 (s, 1H), 7.61 (d, J=2.0 Hz, 1H), 6.65 (bs, 1H), 5.93 (bs, 1H), 5.44 (bs, 1H), 3.55 (dq, J=12.8, 6.4 Hz, 2H), 2.62 (s, 3H), 1.66 (d, J=6.4 Hz, 16H), 1.30 (t, J=7.6 Hz, 3H); MS (EI) for $C_{16}H_{20}N_6O$: 313.3 (MH$^+$).

Example 5c 2-(Ethylamino)-4-methyl-6-(1H-pyrazol-3-yl)pyrido[2,3-a]pyrimidin-7(8H)-one: $^1$H NMR (400 MHz, MeOH-d$_4$: TFA-d, 10:1): δ 8.59 (s, 1H), 8.07 (s, 1H), 7.30 (s, 1H), 3.59 (q, J=8.0 Hz, 2H), 2.88 (s, 3H), 1.28 (t, J=8.0 Hz, 3H); MS (EI) for $C_{13}H_{14}N_6O$: 271.0 (MH$^+$).

Example 5e

8-Cyclopentyl-2-(ethylamino)-4-methyl-6-(1H-pyrazol-3-yl)pyrido[2,3-d]pyrimidin-7(8R)-one: $^1$H NMR (400 MHz, DMSO-d$_6$): δ 8.32 (s, 1H), 7.80 (s, 1H), 7.59 (s, 1H), 6.916 (s, 1H), 5.95 (m, 1H), 2.35 (bs, 2H), 1.95 (bs, 2H), 1.73 (bs, 2H), 1.61 (bs, 2H), 1.12 (t, J=6.8 Hz, 3H), MS (EI) for $C_{18}H_{22}N_6O$: 339.1 (MH$^+$)

Example 5f 6-(2,4-Difluorophenyl)-8-ethyl-2-(ethylamino)-4-methylpyrido[2,3-d]pyrimidin-7(8H)-one: $^1$H NMR (400 MHz, CDCl$_3$): δ 7.78 (d, 2H), 7.52 (m, 1H), 6.85 (m, 2H), 5.38 (bs, 1H), 4.48 (m, 2H), 3.56 (m, 2H), 2.57 (s, 3H), 1.39 (m, 6H); MS (EI) for $C_{18H18}F_2N_4O$: 345.1 (MH$^+$).

Example 5g 6-(3-Chloro-4-fluorophenyl)-8-ethyl-2-(ethylamino)-4-methylpyrido[2,3-d]pyrimidin-7(8H)-one: $^1$H NMR (400 MHz, CDCl$_3$): δ 7.79 (s, 2H), 7.57 (m, 1H), 7.19 (m, 1H), 5.41 (bs, 1H), 4.45 (bs, 2H), 3.58 (m, 2H), 2.59 (m, 3H), 1.36 (m, 6H); MS (EI) for $C_{18H18}Cl_2N_4O$: 361.0 (MH$^+$).

Example 5h 6-(2,4-Dichlorophenyl)-8-ethyl-2-(ethylamino)-4-methylpyrido[2,3-d]pyrimidin-7(8H)-one: $^1$H NMR (400 MHz, CDCl$_3$): δ 7.75 (s, 1H), 7.42 (d, 1H), 7.38 (m, 2H), 5.38 (bs, 1H), 4.42 (m, 2H), 3.59 (m, 2H), 2.56 (s, 3H), 1.24 (m, 6H); MS (EI) for $C_{18H18}Cl_2N_4O$: 377.0 (M$^+$), 379.0 (M+2)

Example 5i 6-(3,4-Difluorophenyl)-8-ethyl-2-(ethylamino)-4-methylpyrido[2,3-d]pyrimidin-7(8H)-one: $^1$H NMR (400 MHz, CDCl$_3$): δ 7.79 (s, 1H), 7.59 (m, 1H), 7.39 (m, 1H), 7.18 (m, 1H), 5.39 (bs, 1H), 4.46 (m, 2H), 3.58 (m, 2H), 2.59 (s, 3H), 1.27 (m, 6H); MS (EI) for $C_{18H18}F_2N_4O$: 345.1 (MH$^+$).

Example 5j

8-Ethyl-2-(ethylamino)-4-methyl-6-[4-(phenyloxy)phenyl]pyrido[2,3-d]pyrimidin-7(8H)-one: $^1$H NMR (400 MHz, CDCl$_3$): δ 7.78 (s, 1H), 7.63 (d, 2H), 7.39 (t, 2H), 7.16 (t, 1H), 7.04 (d, 4H), 5.38 (bs, 1H), 4.47 (m, 2H), 3.57 (m, 2H), 2.59 (s, 3H), 1.26 (m, 6H); MS (EI) for $C_{24}H_{24}N_4O_2$: 401.1 (MH$^+$).

Example 5k

8-Ethyl-2-(ethylamino)-4-methyl-6-naphthaleN-1-ylpyrido[2,3-d]pyrimidin-7(8H)-one: $^1$H NMR (400 MHz, CDCl$_3$): δ 7.84 (d, 2H), 7.80 (s, 1H), 7.73 (d, 1H), 7.48 (m, 4H), 539 (bs, 1H), 4.55 (bs, 2H), 3.59 (m, 2H), 2.54 (s, 3H), 1.37 (m, 6H); MS (EI) for $C_{22}H_{22}N_4O$: 359.1 (MH$^+$).

Example 5m

8-Ethyl-2-(ethylamino)-4-methyl-6-[3-(trifluoromethyl)phenyl]pyrido[2,3-d]pyrimidin-7(8H)-one: $^1$H NMR (400 MHz, CDCl$_3$): δ 7.82 (m, 3H), 7.56 (m, 2H), 5.59 (bs, 1H), 4.47 (d, 2H), 3.51 (m, 2H), 2.58 (s, 3H), 1.30 (m, 6H); MS (EI) for $C_{19}H_{19}F_3N_4O$: 377.1 (MH$^+$).

Example 5n

8-Ethyl-2-(ethylamino)-4-methyl-6-(2-thienyl)pyrido[2,3-d]pyrimidin-7(8H)-one: $^1$H NMR (400 MHz, CDCl$_3$): δ 8.09 (s, 1H), 7.64 (dd, J=3.60, 1.20 Hz, 1H), 7.38 (dd, J=5.20, 1.20 Hz, 1H), 7.10 (dd, J=4.78, 3.60 Hz, 2H), 3.54 (qn, 2H), 2.62 (s, 3H), 1.30 (m, 6H); MS (EI) for $C_{16}H_{18}N_4OS$: 315.0 (MH$^+$).

Example 5p 6-(3-Chlorophenyl)-8-ethyl-2-(ethylamino)-4-methylpyrido[2,3-d]pyrimidin-7(8H)-one: $^1$H NMR (400 MHz, CDCl$_3$): δ 7.78 (s, 1H), 7.65 (s, 1H), 7.56 (dd, 1H), 7.34 (m, 2H), 5.39 (bs, 1H), 4.43 (m, 2H), 3.57 (m, 2H), 2.59 (s, 3H), 1.32 (m, 6H); MS (EI) for $C_{18}H_{19}ClN_4O$: 343.0 (MH$^+$).

Example 5q 6-(4-Chlorophenyl)-8-ethyl-2-(ethylamino)-4-methylpyrido[2,3-d]pyrimidin-7(8H)-one: $^1$H NMR (400 MHz, CDCl$_3$): δ 7.77 (s, 1H), 7.62 (dd, 2H), 7.40 (dd, 2H), 5.38 (bs, 1H), 4.47 (m, 2H), 3.58 (m, 2H), 2.59 (s, 3H), 1.39 (m, 6H); MS (EI) for $C_{18}H_{19}ClN_4O$: 343.0 (MH$^+$).

Example 5r

8-Ethyl-2-(ethylamino)-4-methyl-6-[4-(trifluoromethyl)phenyl]pyrido[2,3-d]pyrimidin-7(8H)-one: $^1$H NMR (400 MHz, CDCl$_3$): δ 7.80 (m, 3H), 7.63 (dd, 2H), 5.39 (bs, 1H), 4.51 (m, 2H), 3.58 (m, 2H), 2.58 (s, 3H), 1.33 (m, 6H); MS (EI) for $C_{19}H_{19}F_3N_4O$: 343.0 (MH$^+$).

Example 5s

8-Ethyl-2-(ethylamino)-4-methyl-6-(3-thienyl)pyrido[2,3-d]pyrimidin-7(8H)-one: $^1$H NMR (400 MHz, CDCl$_3$): δ 8.11 (dd, J=2.10, 0.90 Hz, 1H), 7.94 (s, 1H), 7.52 (dd, J=3.90, 1.20 Hz, 1H), 7.35 (qr, 1H), 5.33 (bs, 1H), 4.52 (qr, 2H), 3.54 (m, 2H), 2.58 (s, 3H), 1.28 (m, 6H); MS (EI) for $C_{16}H_{18}N_4OS$: 315.0 (MH$^+$).

Example 5t

8-Ethyl-2-(ethylamino)-4-methyl-6-(4-methyl-2-thienyl)pyrido[2,3-d]pyrimidin-7(8H)-one: $^1$H NMR (400 MHz, CDCl$_3$): δ 8.01 (s, 1H), 7.52 (s, 1H), 6.93 (s, 1H), 5.38 (bs, 1H), 4.58 (qr, 2H), 3.57 (m, 2H), 2.61 (s, 1H), 2.33 (s, 1H), 1.60 (s, 3H); MS (EI) for $C_{17}H_{20}N_4OS$: 329.0 (MH$^+$).

Example 5u

8-Ethyl-2-(ethylamino)-4-methyl-6-(4-methyl-3-thienyl)pyrido[2,3-d]pyrimidin-7(8H)-one: $^1$H NMR (400 MHz, CDCl$_3$): δ 7.69 (s, 1H), 7.38 (d, 1H), 6.99 (m, 1H), 5.35 (bs, 1H), 4.51 (qr, 2H), 3.57 (m, 2H), 2.58 (s, 3H), 2.22 (s, 3H), 1.32 (m, 6H); MS (EI) for $C_{17}H_{20}N_4OS$: 329.0 (MH$^+$).

Example 5v 1,1-Dimethylethyl 2-[8-ethyl-2-(ethylamino)-4-methyl-7-oxo-7,8-dihydropyrido[2,3-d]pyrimidin-6-yl]-1H-pyrrole-1-carboxylate: $^1$H NMR (400 MHz, CDCl$_3$): δ 7.65 (s, 1H), 7.38 (d, 1H), 6.22 (m, 2H), 5.29 (bs, 1H), 4.41 (m, 2H), 3.57 (m, 2H), 2.56 (s, 3H), 1.41 (s, 9H), 1.22 (m, 6H); MS (EI) for $C_{21}H_{27}N_5O_3$: 398.0 (MH$^+$).

Example 5w

8-Ethyl-2-(ethylamino)-4-methyl-6-(1H-pyrrol-2-yl)pyrido[2,3-d]pyrimidin-7(8H)-one: $^1$H NMR (400 MHz, CDCl$_3$): δ 11.1 (bs, 1H), 7.99 (s, 1H), 6.85 (d, 1H), 6.62 (d, 1H), 6.29 (d, 1H), 5.28 (bs, 1H), 4.57 (m, 2H), 3.56 (m, 2H), 2.61 (s, 3H), 1.35 (m, 6H); MS (EI) for $C_{16}H_{19}N_5O$: 298.1 (MH$^+$).

Example 5x

8-Ethyl-2-(ethylamino)-6-furan-3-yl-4-methylpyrido[2,3-d]pyrimidin-7(8H)-one: $^1$H NMR (400 MHz, CDCl$_3$): δ 8.42 (s, 1H), 7.83 (s, 1H), 7.43 (s, 1H), 6.76 (s, 1H), 5.37 (bs, 1H), 4.52 (m, 2H), 3.58 (m, 2H), 2.61 (s, 3H), 1.30 (m, 6H); MS (EI) for $C_{16}H_{18}N_4O_2$: 299.1 (MH$^+$).

Example 5y

8-Ethyl-2-(ethylamino)-4-methyl-6-[1-(phenylmethyl)-1H-pyrazol-4-yl]pyrido[2,3-d]pyrimidin-7(8H)-one: $^1$H NMR (400 MHz, CDCl$_3$): δ 8.39 (s, 1H), 7.98 (d, 1H), 7.96 (d, 1H), 7.35 (m, 5H), 5.39 (s, 2H), 5.35 (bs, 1H), 4.52 (m, 2H), 3.58 (m, 2H), 2.62 (s, 3H), 1.35 (m, 6H); MS (EI) for $C_{22}H_{24}N_6O$: 389.3 (MH$^+$).

Example 5z 6-(3,5-Dimethylisoxazol-4-yl)-8-ethyl-2-(ethylamino)-4-methylpyrido[2,3-d]pyrimidin-7(8H)-one: $^1$H NMR (400 MHz, CDCl$_3$): δ 7.59 (s, 1H), 7.24 (s, 1H), 5.43 (bs, 1H), 4.47 (bs, 2H), 3.56 (m, 2H), 2.58 (s, 3H), 2.39 (s, 3H), 2.25 (s, 3H), 1.29 (m, 6H); MS (EI) for $C_{17}H_{21}N_5O_2$: 328.1 (MH$^+$).

Example 5aa

8-Ethyl-2-(ethylamino)-4-methyl-6-(1H-pyrazol-5-yl)pyrido[2,3-d]pyrimidin-7(8H)-one: $^1$H NMR (400 MHz, CDCl$_3$): δ 8.11 (s, 1H), 7.62 (s, 1H), 6.65 (d, 1H), 5.43 (bs, 1H), 4.58 (m, 2H), 3.59 (m, 2H), 2.62 (s, 3H), 1.38 (m, 6H); MS (EI) for $C_{15}H_{18}N_6O$: 299.1 (MH).

Example 5bb

8-Ethyl-4-methyl-6-(1H-pyrazol-5-yl)-2-[(2,2,2-trifluoroethyl)amino]pyrido[2,3-d]pyrimidin-7(8H)-one: $^1$H NMR (400 MHz, CDCl$_3$): δ 8.18 (s, 1H), 7.63 (d, 1H), 6.73 (d, 1H), 5.62 (bs, 1H), 4.58 (m, 2H), 4.30 (m, 2H), 2.74 (s, 3H), 1.35 (t, 3H); MS (EI) for $C_{15}H_{15}F_3N_6O$: 353.0 (MH$^+$.

Example 5cc

8-Ethyl-2-(ethylamino)-4-methyl-6-(1,3-thiazol-2-yl)pyrido[2,3-d]pyrimidin-7(8H)-one: $^1$H NMR (400 MHz, CDCl$_3$): δ 8.87 (s, 1H), 7.98 (s, 1H), 7.43 (s, 1H), 7.22 (s, 1H), 5.56 (bs, 1H), 4.58 (bs, 2H), 2.72 (s, 3H0, 1.36 (m, 6H); MS (EI) for $C_{15}H_7N_5OS$: 316.0 (MH+).

Example 6

6-Biphenyl-4-yl-8-ethyl-2-(ethylamino)-4-methylpyrido[2,3-d]pyridimidiN-7(8H)-one

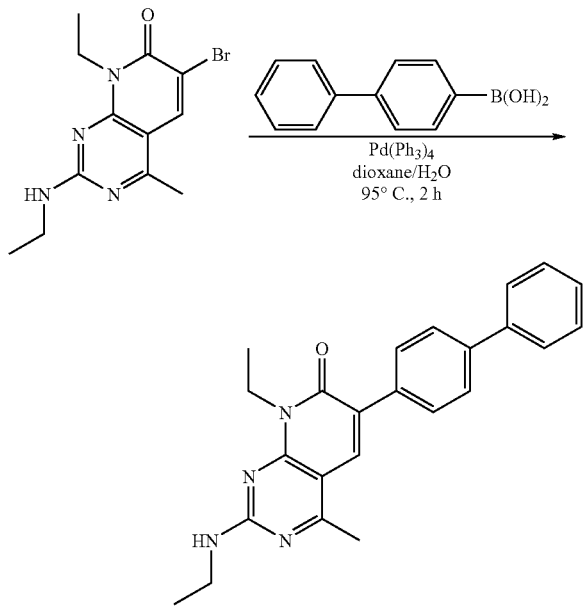

2-Ethylamino-6-bromo-8-ethyl-4-methylpyrido[2,3-d]pyrimidin-7(8H)-one (60 mg, 0.194 mmol), $K_2CO_3$ (81.0 mg, 3.0 equiv.), biphenyl boronic acid (17.8 mg, 1.5 equiv.), and $Pd(PPh_3)_4$ (10 mol %, 225 mg) were added to dioxane/$H_2O$ (10 mL/3 mL). The reaction was heated to 95° C. and stirred for 2 h. The reaction mixture was partitioned between organic and aqueous layers with ethyl acetate (20 mL) and $H_2O$ (10 mL) and saturated aqueous NaCl (5 mL). The organic layer was dried over anhydrous magnesium sulfate, filtered and evaporated to give 6-Biphenyl-4-yl-8-ethyl-2-(ethylamino)-4-methylpyrido[2,3-d]pyridimidiN-7(8H)-one (48.42 mg, 65% yield): $^1$H NMR (400 MHz, CDCl$_3$): δ 7.81 (s, 1H), 7.74 (m, 2H), 7.60 (m, 4H), 7.42 (m, 2H), 7.38 (m, 1H), 4.50 (q, 2H), 3.60 (q, 2H), 2.60 (s, 3H), 1.30 (m, 6H); MS (EI) for $C_{24}H_{24}N_4O$: 385.1 (MH+).

Using the same or analogous synthetic techniques and substituting with appropriate reagents, the following compounds were prepared:

Example 6a

8-Ethyl-2-(ethylamino)-4-methyl-6-[4-(methyloxy)phenyl]pyrido[2,3-d]pyridimidiN-7(8H)-one: $^1$H NMR (400 MHz, CDCl$_3$): δ 7.81 (s, 1H), 7.60 (d, 2H), 6.96 (d, 2H), 4.50 (q, 2H), 3.82 (s, 3H), 3.58 (q, 2H), 2.58 (s, 3H), 1.30 (m, 6H); MS (EI) for $C_{19}H_{22}N_4O_2$: 339.1 (MH+).

Example 6b

8-Ethyl-2-(ethylamino)-4-methyl-6-[2-(methyloxy)phenyl]pyrido[2,3-d]pyridimidiN-7(8H)-one: $^1$H NMR (400 MHz, CDCl$_3$): δ 7.81 (s, 1H), 7.60 (d, 2H), 6.96 (d, 2H), 4.50 (q, 2H), 3.80 (s, 3H), 3.58 (q, 2H), 2.50 (s, 3H), 1.30 (m, 6H); MS (EI) for $C_{19}H_{22}N_4O_2$: 339.1 (MH+).

Example 6c

6-[2,4-Bis(methyloxy)phenyl]-8-ethyl-2-(ethylamino)-4-methylpyrido[2,3-d]pyrimidin-7(8R)-one: $^1$H NMR (400 MHz, CDCl$_3$): δ 7.70 (s, 1H), 7.30 (s, 1H), 6.60 (m, 2H), 4.50 (q, 2H), 3.82 (s, 3H), 3.80 (s, 3H), 3.45 (q, 2H), 2.50 (s, 3H), 1.30 (m, 6H); MS (EI) for $C_{20}H_{24}N_4O_3$: 369.1 (MH+).

Example 6d

8-Ethyl-2-(ethylamino)-4-methyl-6-[3-(methyloxy)phenyl]pyrido[2,3-d]pyridimidiN-7(8H)-one: $^1$H NMR (400 MHz, CDCl$_3$): δ 7.81 (s, 1H), 7.60 (d, 2H), 6.96 (d, 2H), 4.50 (q, 2H), 3.80 (s, 3H), 3.58 (q, 2H), 2.50 (s, 3H), 1.30 (m, 6H); MS (EI) for $C_{19}H_{22}N_4O_2$: 339.1 (MH+).

Example 6e 8-(5-Chloro-2-thienyl)-8-ethyl-2-(ethylamino)-4-methylpyrido[2,3-d]pyrimidin-7(8H)-one: $^1$H NMR (400 MHz, CDCl$_3$): δ 8.00 (s, 1H), 7.38 (d, 2H), 6.96 (d, 2H), 4.50 (q, 2H), 3.58 (q, 2H), 2.60 (s, 3H), 1.30 (m, 6H); MS (EI) for $C_{16}H_{17}ClN_4OS$: 349.2 (MH+).

Example 6f

8-Ethyl-2-(ethylamino)-4-methyl-6-pyrimidin-5-ylpyrido[2,3-d]pyridimidiN-7(8H)-one: $^1$H NMR (400 MHz, DMSO-d$_6$): δ 9.19 (s, 1H), 9.16 (s, 1H), 8.23 (s, 1H), 8.00 (m, 1H), 4.38 (q, 2H), 3.40 (q, 2H), 2.50 (s, 3H), 1.30 (m, 6H); MS (EI) for $C_{16}H_{18}N_6O$: 311.3 (MH+).

Example 6g

8-Ethyl-2-(ethylamino)-6-(3-fluoropyridiN-4-yl)-4-methylpyrido[2,3-d]pyrimidin-7(8H)-one: $^1$H NMR (400 MHz, CDCl$_3$): δ 8.58 (s, 1H), 8.42 (d, 1H), 7.98 (s, 1H), 7.60 (t, 1H), 4.50 (q, 2H), 3.58 (q, 2H), 2.60 (s, 3H), 1.30 (m, 6H); MS (EI) for $C_{17}H_{18}FN_5O$: 328.3 (MH+).

Example 6h

8-Ethyl-2-(ethylamino)-6-(1H-indole-6-yl)-4-methylpyrido[2,3-d]pyrimidin-7(8H)-one: $^1$H NMR (400 MHz, DMSO-d$_6$): δ 11.2 (s, 1H), 7.90 (s, 1H), 7.88 (s, 1H), 7.42 (s, 2H), 7.38 (s, 1H), 6.50 (s, 1H), 4.40 (q, 2H), 3.40 (q, 2H), 2.42 (s, 3H), 1.30 (m, 6H); MS (EI) for $C_{20}H_{21}N_5O$: 348.3 (MH+).

Example 6i

8-Ethyl-2-(ethylamino)-4-methyl-6-(5-phenyl-2-thienyl)pyrido[2,3-d]pyrimidin-7(8H)-one: $^1$H NMR (400 MHz, DMSO-d$_6$): δ 8.40 (s, 1H), 7.81 (d, 1H), 7.70 (d, 2H), 7.50 (d, 1H), 7.42 (m, 2H), 7.30 (m, 1H), 4.40 (q, 2H), 3.40 (q, 2H), 2.42 (s, 3H), 1.30 (m, 6H); MS (EI) for $C_{22}H_{22}N_4OS$: 391.3 (f).

Example 6j

8-Ethyl-2-(ethylamino)-4-methyl-6-phenylpyrido[2,3-d]pyrimidin-7(8H)-one $^1$H NMR (400 MHz, CDCl$_3$): δ 7.78 (s, 1H), 7.46 (m, 5H), 5.41 (bs, 1H), 4.50 (q, J=6.8 Hz, 2H), 3.60 (m, 2H), 2.57 (s, 3H), 1.30 (m, 6H); MS (EI) for $C_{18H}20N_4O$: 309.2 (MH+).

Example 6k

8-Ethyl-2-(ethylamino)-6-(3-fluorophenyl)-4-methylpyrido[2,3-d]pyrimidin-7(8H)-one: $^1$H NMR (400 MHz, CDCl$_3$): δ 7.79 (s, 1H), 7.46-7.02 (m, 4H), 5.41 (bs, 1H), 4.51 (q, J=6.4 Hz, 2H), 3.55 (q, J=6.8 Hz, 2H), 2.58 (s, 3H), 1.34 (t, J=6.80 Hz, 3H), 1.29 (t, J=6.40 Hz, 3H); MS (EI) for C$_{18}$H$_{19}$FN$_4$O: 327.3 (MH$^+$).

Example 6m 8-ethyl-2-(ethylamino)-6-(2-fluorophenyl)-4-methylpyrido[2,3-d]pyrimidin-7(8H)-one: $^1$H NMR (400 MHz, CDCl$_3$): δ 7.80 (s, 1), 7.52-7.12 (m, 4H), 5.33 (bs, 1H), 4.49 (q, J=6.8 Hz, 2H), 3.53 (q, J=7.2 Hz, 2H), 2.55 (s, 3H), 1.34 (t, J=7.20 Hz, 3H), 1.28 (t, J=6.80 Hz, 3H); MS (EI) for C$_{18}$H$_{19}$FN$_4$O: 327.3 (MH$^+$).

Example 6n 8-ethyl-2-(ethylamino)-6-(4-fluorophenyl)-4-methylpyrido[2,3-d]pyrimidin-7(8H)-one: $^1$H NMR (400 MHz, CDCl$_3$): δ 7.75 (s, 1H), 7.66-7.08 (m, 4H), 5.30 (bs, 1H), 4.52 (q, J=6.4 Hz, 2H), 3.54 (q, J=6.8 Hz, 2H), 2.58 (s, 3H), 1.34 (t, J=6.80 Hz, 3H), 1.29 (t, J=6.40 Hz, 3H); MS (EI) for C$_{18}$H$_{19}$FN$_4$O: 327.3 (MH$^+$).

Intermediate 2

3-Chloroperbenzoic acid (1.78 g, 10.4 mmol) was added to a solution of 6-bromo-4-methyl-8-(1-methylethyl)-2-(methylthio)pyrido[2,3-d]pyrimidin-7(8H)-one (1.33 g, 4.14 mmol), prepared using procedures similar to those described in Example 1, in dichloromethane (30.0 mL) at room temperature. After 1, the reaction was diluted with dichloromethane (50 mL) and washed twice with saturated NaHCO$_3$, followed by brine. The organic phase was separated and dried over Na$_2$SO$_4$, filtered, and concentrated in vacuo. The residue was precipitated with ethyl acetate/hexanes to provide the corresponding sulfone (1.31 g, 93% yield) as an off-white solid.

Example 8

2-Amino-4-methyl-8-(phenylmethyl)-6-(1H-pyrazol-3-yl)pyrido[2,3-d]pyrimidin-7(8H)-one

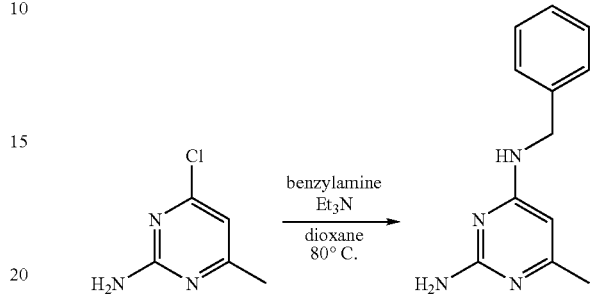

Triethylamine (3.4 mL, 24.6 mmol) was added to a suspension of 2-amino-4-chloro-6-methylpyrimidine (Aldrich, 1.77 g, 12.3 mmol) and benzylamine (1.98 g, 18.5 mmol) in anhydrous dioxane (20 mL). The reaction was heated to 80° C. and allowed to run for 12 h. Upon cooling to room temperature, a white precipitate formed which was collected by vacuum filtration. The solid was recrystallized from acetone:hexanes to afford N$^4$-benzyl-6-methylpyrimidine-2,4-diamine (2.33 g, 89% yield) as a white solid.

Iodine (3.04 g, 12.0 mmol) was added to a solution of N$^4$-benzyl-6-methylpyrimidine-2,4-diamine (2.33 g, 10.9 mmol) in anhydrous MeOH (50 mL) at 0° C. The reaction was allowed to warm to room temperature overnight. After 12 hours, an additional 0.5 equiv of iodine was added, and the reaction warmed to 50° C. After four hours, the reaction was cooled to room temperature and concentrated in vacuo. The residue was diluted with ethyl acetate (200 mL) and washed with 10% NaHSO$_3$ (200 mL). The aqueous phase was separated and washed once more with ethyl acetate (200 mL). The organic phases were combined, washed with brine, separated and dried over Na$_2$SO$_4$. The filtrate was concentrated in vacuo to afford the product N$^4$-benzyl-5-iodo-6-methylpyrimidine-2,4-diamine (3.14 g, 85% yield).

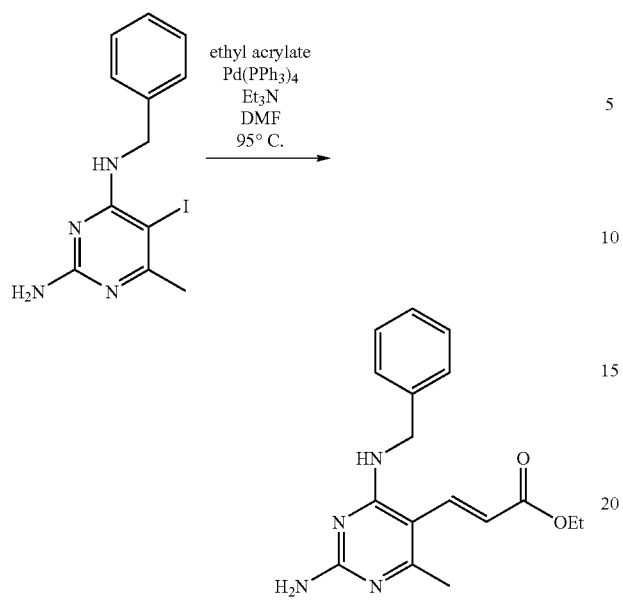

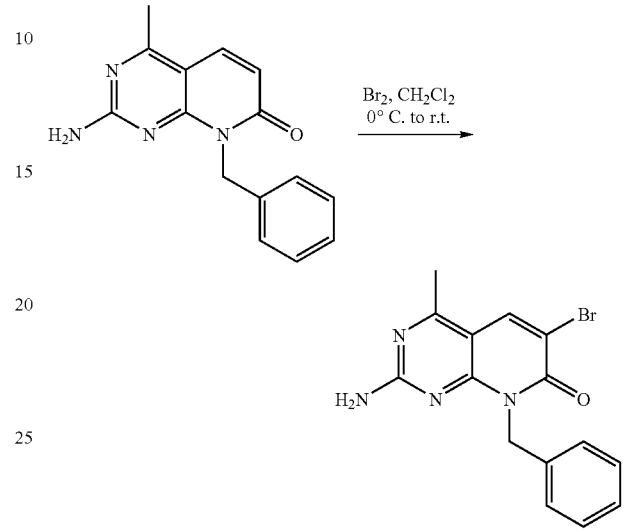

late (0.954 g, 3.05 mmol) and the reaction refluxed at 160° C. under a nitrogen atmosphere. After 20 hours, the reaction was cooled to room temperature and concentrated in vacuo. Purification on $SiO_2$ (1:1 methylene chloride:ethyl acetate) afforded the product (0.508 g, 62% yield) as an off-white solid.

Triethylamine (7.60 mL, 54.5 mmol) was added to a suspension of $N^4$-benzyl-5-iodo-6-methylpyrimidine-2,4-diamine (3.14 g, 10.9 mmol), ethyl acrylate (3.55 mL, 32.7 mmol) and $Pd(PPh_3)_4$ (629 mg, 0.545 mmol) in anhydrous DMF (20 mL). The reaction was heated to 95° C. under nitrogen. After 24 h, the reaction was allowed to cool to room temperature and concentrated in vacuo. The residue was poured into a 10% solution of LiCl and washed with ethyl acetate (100 mL). The organic phase was separated and washed with brine, separated and dried over $Na_2SO_4$. The filtrate was concentrated in vacuo and purified on $SiO_2$ (3:2 methylene chloride:ethyl acetate) to afford (E)-ethyl-3-(2-amino-4-(benzylamino)-6-methylpyrimidin-5-yl)acrylate (0.954 g, 28% yield) as a light yellow solid.

Bromine (72 μL, 1.40 mmol) was added to a suspension of 2-amino-4-methyl-8-(phenylmethyl)pyrido[2,3-d]pyrimidin-7(8H)-one (0.340 g, 1.27 mmol) in methylene chloride (20 mL) at 0° C. The reaction was allowed to warm to room temperature over one hour and the resulting precipitate collected by vacuum filtration to afford 2-amino-6-bromo-4-methyl-(8-phenylmethyl)pyrido[2,3-a]pyrimidin-7(8H)-one (0.435 g, 99% yield) after drying. The yellow solid was used in the next step without further purification.

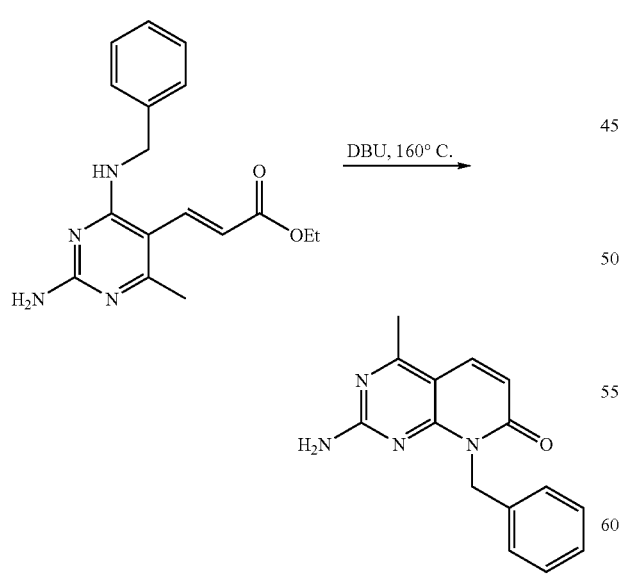

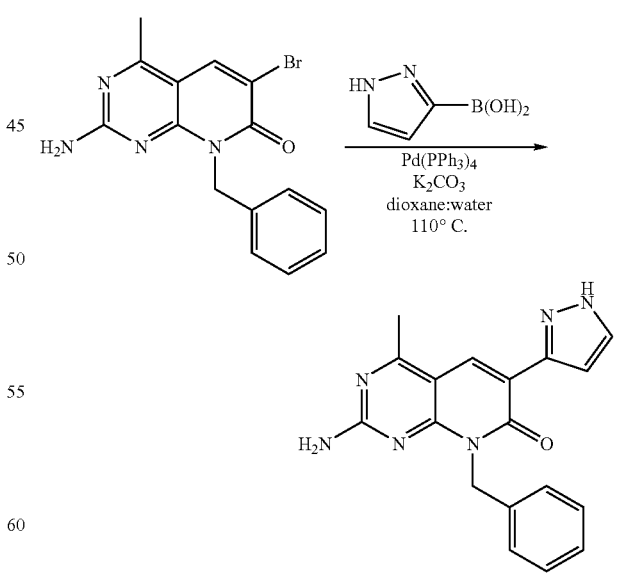

2-amino-4-methyl-8-(phenylmethyl)pyrido[2,3-d]pyrimidin-7(8H)-one Diazabicyclo[5.4.0]undec-7-ene (DBU) (1.83 mL, 12.2 mmol) was added to a flask charged with (E)-ethyl-3-(2-amino-4-(benzylamino)-6-methylpyrimidin-5-yl)acry- A 10:1 solution of dioxane and water (1.1 mL) was added to a flask charged with 2-amino-6-bromo-4-methyl-(8-phenylmethyl)pyrido[2,3-d]pyrimidin-7(8H)-one (0.435 g, 1.27 mmol), 1H-pyrazole-5-boronic acid (0.284 g, 2.54 mmol), Pd(PPh$_3$)$_4$ (0.073 mg, 0.063 mmol), and K$_2$CO$_3$ (0.527 g, 3.81 mmol). The flask was flushed with nitrogen and fitted with a reflux condenser and heated to 110° C. After 12 h the reaction was cooled to room temperature and diluted with ethyl acetate (100 mL) and washed with water. The aqueous phase was acidified to pH 1.0 and washed with ethyl acetate (100 mL). The organic phases were combined and washed with brine, separated and dried over Na$_2$SO$_4$, filtered and concentrated in vacuo. The residue was precipitated with ethyl acetate to give 2-Amino-4-methyl-8-(phenylmethyl)-6-(1H-pyrazol-3-yl)pyrido[2,3-d]pyrimidin-7(8H)-one (0.062 g, 15% yield) as a yellow solid: $^1$H NMR (400 MHz, DMSO-d$_6$): δ 13.10 (bs, 1H), 12.93 (bs, 1H), 8.47 (s, 1H), 7.76 (bs, 1H), 7.51 (bs, 1H), 7.28 (m, 5H), 6.97 (s, 1H), 5.55 (s, 2H), 2.55 (bs, 3H); MS (EI) for C$_{18}$H$_{16}$N$_6$O: 333.1 (MH$^+$).

Example 9

2-Amino-8-ethyl-4-methyl-6-(4-methyl-3-thienyl)pyrido[2,3-d]pyrimidin-7(8H)-one

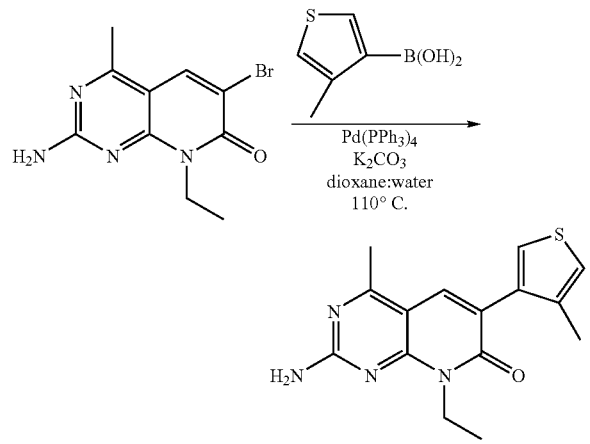

A 3:1 solution of dioxane and water (4 mL) was added to a flask charged with 2-amino-6-bromo-8-ethyl-4-methylpyrido[2,3-d]pyrimidin-7(8H)-one (0.140 g, 0.495 mmol) from above, 4-methylthiophene-3-boronic acid (0.140 g, 0.989 mmol), Pd(PPh$_3$)$_4$ (0.057 mg, 0.050 mmol), and K$_2$CO$_3$ (0.205 g, 1.48 mmol). The flask was flushed with nitrogen and fitted with a reflux condenser and heated to 100° C. After 12 hours the reaction was cooled to room temperature and diluted with ethyl acetate (70 mL) and washed with water. The aqueous phase was separated and washed with an additional amount of ethyl acetate (70 mL). The organic phases were combined and washed with brine, separated and dried over Na$_2$SO$_4$, filtered and concentrated in vacuo. The residue was purified on SiO$_2$ (1:1 methylene chloride:ethyl acetate) to give 2-Amino-8-ethyl-4-methyl-6-(4-methyl-3-thienyl)pyrido[2,3-d]pyrimidin-7(8H)-one (0.081 g, 55% yield) as an off-white solid: $^1$H NMR (400 MHz, DMSO-d$_6$): δ 7.84 (s, 1H), 7.46 (d, J=4.0 Hz, 1H), 7.19 (m, 3H), 4.32 (q, J=8.0 Hz, 2H), 2.52 (s, 3H), 2.11 (bs, 3H), 1.19 (t, J=8.0 Hz, 3H); MS (EI) for C$_{15}$H$_{16}$N$_4$OS: 301.1 (MH$^+$).

Using the same or analogous synthetic techniques and substituting with appropriate reagents, the following compounds were prepared:

Example 9a

2-Amino-8-ethyl-4-methyl-6-(3-thienyl)pyrido[2,3-d]pyrimidin-7(8B-one $^1$H NMR (400 MHz, CDCl$_3$): δ 8.11 (dd, J=2.8, 1.2 Hz, 1H), 7.95 (s, 1H), 7.51 (dd, J=5.2, 1.2 Hz, 1H), 7.37 (dd, J=4.8, 3.2 Hz, 1H), 5.21, (bs, 2H), 4.48 (q, J=6.8 Hz, 2H), 2.63 (s, 3H), 1.32 (t, J=7.2 Hz, 3H); MS (EI) for C$_{14}$H$_{14}$N$_4$OS: 287.0 (MH$^+$).

Example 9b

2-Amino-8-ethyl-6-furan-3-yl-4-methylpyrido[2,3-d]pyrimidin-7(8H)-one: $^1$H NMR (400 MHz, CDCl$_3$): δ 8.47 (bs, 1H), 7.85 (s, 1H), 7.49 (t, J=1.6 Hz, 1H), 6.77 (dd, J=2.0, 0.8 Hz, 1H), 5.19, (bs, 2H), 4.48 (q, J=6.8 Hz, 2H), 2.64 (s, 3H), 1.31 (t, J=7.2 Hz, 3H); MS (EI) for C$_{14}$H$_{14}$N$_4$O$_2$: 271.1 (MH$^+$).

Example 9c

2-Amino-6-(3,5-dimethylisoxazol-4-yl)-8-ethyl-4-methylpyrido[2,3-d]pyrimidin-7(8H)-one: $^1$H NMR (400 MHz, CDCl$_3$): δ 7.62 (s, 1H), 5.27, (bs, 2H), 4.44 (q, J=7.2 Hz, 2H), 2.59 (s, 3H), 2.38 (s, 3H), 2.25 (s, 3H), 1.31 (t, J=6.8 Hz, 3H); MS (EI) for C$_{15}$H$_{17}$N$_5$O$_2$: 300.1 (MH$^+$).

Example 9d

2-Amino-8-ethyl-6-isoxazol-4-yl-4-methylpyrido[2,3-d]pyrimidin-7(8H)-one $^1$H NMR (400 MHz, CDCl$_3$): δ 9.36 (s, 1H), 8.71 (s, 1H), 7.91 (s, 1H), 5.30, (bs, 2H), 4.48 (q, J=7.2 Hz, 2H), 2.67 (s, 3H), 1.32 (t, J=6.8 Hz, 3H); MS (EI) for C$_{13}$H$_{13}$N$_5$O$_2$: 272.0 (MH$^+$).

Example 9e

2-Amino-8-ethyl-6-furan-2-yl-4-methylpyrido[2,3-d]pyrimidin-7(8H)-one: $^1$H NMR (400 MHz, CDCl$_3$): δ 8.19 (s, 1H), 7.48 (d, J=0.8 Hz, 1H), 7.37 (d, J=3.6 Hz, 1H), 6.53 (dd, J=3.6, 2.0 Hz 1H), 5.21, (bs, 2H), 4.48 (q, J=7.2 Hz, 2H), 2.66 (s, 3H), 1.32 (t, J=6.8 Hz, 3H); MS (EI) for C$_{14}$H$_{14}$N$_4$O$_2$: 271.0 (MH$^+$).

Example 9f 5-(2-Amino-8-ethyl-4-methyl-7-oxo-7,8-dihydropyrido[2,3-d]pyrimidin-6-yl)thiophene-2-carbonitrile: $^1$H NMR (400 MHz, CDCl$_3$): δ 8.24 (s, 1H), 7.61 (d, J=4.4 Hz, 1H), 7.55 (d, J=4.4 Hz, 1H), 5.33, (bs, 2H), 4.48 (q, J=7.2 Hz, 2H), 2.68 (s, 3H), 1.33 (t, J=6.8 Hz, 3H); MS (EI) for C$_{15}$H$_{13}$N$_5$OS: 312.0 (MH$^+$).

Example 9g

2-Amino-8-ethyl-4-methyl-6-(1H-pyrazol-4-yl)pyrido[2,3-d]pyrimidin-7(8H)-one: $^1$H NMR (400 MHz, DMSO-d$_6$): δ 12.88 (s, 1H), 8.38 (s, 1H), 8.17 (s, 2H), 7.10 (bs, 2H), 4.35 (q, J=7.2 Hz, 2H), 2.59 (s, 3H), 1.20 (t, J=7.2 Hz, 3H); MS (EI) for C$_{13}$H$_{14}$N$_6$O: 271.0 (MH$^+$).

Example 9h

2-Amino-8-ethyl-4-methyl-6-(1,3-thiazol-2-yl)pyrido[2,3-d]pyrimidin-7(8H)-one: $^1$H NMR (400 MHz, CDCl$_3$): δ 8.94 (s, 1H), 7.94 (d, J=3.2 Hz, 1H), 7.46 (d, J=3.2 Hz, 1H), 5.34 (bs, 2H), 4.54 (q, J=7.2 Hz, 2H), 2.73 (s, 3H), 1.35 (t, J=7.2 Hz, 3H); MS (EI) for C$_{13}$H$_{13}$N$_5$OS: 288.0 (MH$^+$).

Example 9i

2-Amino-8-ethyl-4-methyl-6-(1-methyl-1H-pyrrol-2-yl)pyrido[2,3-d]pyrimidin-7(8H)-one: $^1$H NMR (400 MHz, DMSO-d$_6$): δ 7.81 (s, 1H), 7.20 (bs, 2H), 6.81 6.11 (dd, J=3.6, 2.0 Hz, 1H), 6.02 (t, J=3.2 Hz, 1H), 4.32 (q, J=7.2 Hz, 2H), 3.49 (s, 3H), 2.52 (s, 3H), 1.19 (t, J=7.2 Hz, 3H); MS (EI) for C$_{15}$H$_{17}$N$_5$O: 284.1 (MH$^+$).

Example 9j

2-Amino-8-ethyl-4-methyl-6-phenylpyrido[2,3-d]pyrimidin-7(8H)-one: $^1$H NMR (400 MHz, CDCl$_3$): δ 7.79 (s, 1H), 7.65 (d, J=6.8 Hz, 2H), 7.43 (d, J=7.2 Hz, 2H), 7.36 (d, J=7.2 Hz, 1H), 5.24 (bs, 2H), 4.47 (q, J=7.2 Hz, 2H), 2.60 (s, 3H), 1.31 (d, J=7.2 Hz, 3H), MS (EI) for C$_{16}$H$_{16}$N$_4$O: 281.2 (MH$^+$).

Example 9k

2-Amino-8-ethyl-6-(4-methoxyphenyl)-4-methylpyrido[2,3-d]pyrimidin-7(8H)-one: $^1$H NMR (400 MHz, CDCl$_3$): δ 7.75 (s, 1H), 7.62 (d, J=8.8 Hz, 2H), 6.96 (d, J=8.8 Hz, 2H), 5.17 (bs, 2H), 4.47 (q, J=6.8 Hz, 2H), 3.85 (s, 3H), 2.60 (s, 3H), 1.31 (d, J=7.2 Hz, 3H), MS (EI) for C$_{17}$H$_{18}$N$_4$O$_2$: 311.2 (MH$^+$)

Example 9m

2-Amino-8-ethyl-6-(2-methoxyphenyl)-4-methylpyrido[2,3-d]pyrimidin-7(8,H)-one: $^1$H NMR (400 MHz, CDCl$_3$): δ 7.75 (m, 1H), 7.36 (m, 2H), 7.01 (m, 2H), 5.20 (bs, 2H), 4.45 (m, 2H), 3.82 (s, 3H), 2.56 (s, 3H), 1.31 (m, 3H), MS (EI) for C$_{17}$H$_{18}$N$_4$O$_2$: 311.2 (MH$^+$)

Example 9n

2-Amino-6-(4-chlorophenyl)-8-ethyl-4-methylpyrido[2,3-d]pyrimidin-7(8H)-one: $^1$H NMR (400 MHz, CDCl$_3$): δ 7.78 (s, 1H), 7.61 (d, J=8.8 Hz, 2H), 7.39 (d, J=8.8 Hz, 2H), 5.23 (bs, 2H), 4.46 (q, J=7.2 Hz, 2H), 2.61 (s, 3H), 1.31 (d, J=6.8 Hz, 3H), MS (EI) for C$_{16}$H$_{15}$ClN$_4$O: 315.1 (MH$^+$)

Example 9p

2-Amino-6-(3-chlorophenyl)-8-ethyl-4-methylpyrido[2,3-d]pyrimidin-7(8H)-one: $^1$H NMR (400 MHz, CDCl$_3$): δ 7.79 (s, 1H), 7.66 (m, 1H), 7.56 (m, 1H), 7.35 (m, 2H), 5.25 (bs, 2H), 4.46 (q, J=5.6 Hz, 2H), 2.61 (s, 3H), 1.31 (d, J=7.2 Hz, 3H), MS (EI) for C$_{16}$H$_{15}$ClN$_4$O: 315.1 (MH$^+$)

Example 9q

2-Amino-6-(2-chlorophenyl)-8-ethyl-4-methylpyrido[2,3-d]pyrimidin-7(8H)-one: $^1$H NMR (400 MHz, CDCl$_3$): δ 7.75 (s, 1H), 7.67 (m, 1H), 7.54 (m, 2H), 7.38 (m, 1H), 7.333 (m, 1H), 5.22 (bs, 2H), 4.46 (q, J=6.8 Hz, 2H), 2.57 (s, 3H), 1.31 (d, J=6.8 Hz, 3H), MS (EI) for C$_{16}$H$_{15}$ClN$_4$O: 315.1 (MH$^+$)

Example 9r

2-Amino-6-(2,4-dichlorophenyl)-8-ethyl-4-methylpyrido[2,3-d]pyrimidin-7(8H)-one: $^1$H NMR (400 MHz, CDCl$_3$): δ 7.77 (s, 1H), 7.67 (m, 1H), 7.49 (m, 1H), 7.32 (m, 1H), 5.24 (bs, 2H), 4.45 (q, J=6.8 Hz, 2H), 2.58 (d, J=7.2 Hz, 3H), 1.30 (d, J=7.2 Hz, 3H), MS (EI) for C$_{16}$H$_{14}$Cl$_2$N$_4$O: 349.1 (MH$^+$)

Example 9t

2-Amino-8-ethyl-4-methyl-6-(2-thienyl)pyrido[2,3-d]pyrimidin-7(8H)-one: $^1$H NMR (400 MHz, DMSO-d$_6$): δ 8.39 (s, 1H), 7.85-7.13 (m, 5H), 4.37 (q, J=7.2 Hz, 2H), 2.62 (s, 3H), 1.18 (t, J=7.2 Hz, 3H); MS (EI) for C$_{14}$H$_{14}$N$_4$OS: 287.1 (MH$^+$).

Example 9u

2-Amino-8-ethyl-6-(4-fluorophenyl)-4-methylpyrido[2,3-d]pyrimidin-7(8H)-one: $^1$H NMR (400 MHz, DMSO-d$_6$): δ 7.99 (s, 1H), 7.76-7.22 (m, 6H), 4.34 (q, J=7.2 Hz, 2H), 2.56 (s, 3H), 1.20 (t, J=7.2 Hz, 3H); MS (EI) for C$_{16}$H$_{15}$FN$_4$O: 299.2 (MH$^+$).

Example 9v

2-Amino-8-ethyl-6-(3-fluorophenyl)-4-methylpyrido[2,3-d]pyrimidin-7(8H)-one: $^1$H NMR (400 MHz, DMSO-d$_6$): δ 8.06 (s, 1H), 7.61-7.44 (m, 3H), 7.29 (bs, 2H), 7.20 7.15 (m, 1H), 4.34 (q, J=7.2 Hz, 2H), 2.58 (s, 3H), 1.20 (t, J=7.2 Hz, 3H); MS (EI) for C$_{16}$H$_{15}$FN$_4$O: 299.2 (MH$^+$).

Example 9w

2-Amino-8-ethyl-6-(2-fluorophenyl)-4-methylpyrido[2,3-d]pyrimidin-7(8H)-one: $^1$H NMR (400 MHz, DMSO-d$_6$): δ 7.96 (s, 1H), 7.50-7.23 (m, 6H), 4.32 (q, J=6.8 Hz, 2H), 2.52 (s, 3H), 1.19 (t, J=6.8 Hz, 3H); MS (EI) for C$_{16}$H$_{15}$FN$_4$O: 299.2 (MH$^+$).

Example 9x

Methyl 3-(2-amino-8-ethyl-4-methyl-7-oxo-7,8-dihydropyrido[2,3-d]pyrimidin-6-yl)benzoate: $^1$H NMR (400 MHz, DMSO-d$_6$): δ 8.34 (s, 1H), 8.06 (s, 1H), 7.95-7.55 (m, 3H), 7.28 (bs, 1H), 4.35 (q, J=6.8 Hz, 2H), 3.89 (s, 3H), 2.58 (s, 3H), 1.21 (t, J=6.8 Hz, 3H); MS (EI) for C$_{18}$H$_{18}$N$_4$O$_3$: 339.2 (MH$^+$).

Example 9y

2-Amino-8-ethyl-4-methyl-6-pyrimidin-5-ylpyrido[2,3-d]pyrimidin-7(8H)-one: $^1$H NMR (400 MHz, DMSO-d$_6$): δ 8.39 (s, 1H), 7.65-7.30 (m, 5H), 4.31 (q, J=7.2 Hz, 2H), 2.50 (s, 3H), 1.17 (t, J=7.2 Hz, 3H); MS (EI) for C$_{14}$H$_{14}$N$_6$O: 283.2 (MH$^+$).

Example 10

2-Amino-8-ethyl-6-(1H-imidazol-5-yl)-4-methylpyrido[2,3-d]pyrimidin-7(8H)-one

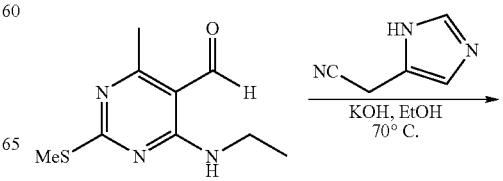

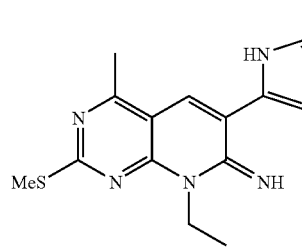

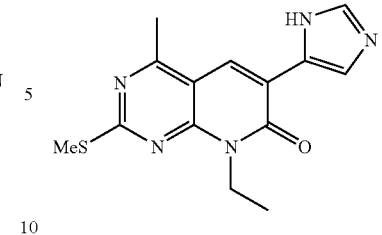

A solution of potassium hydroxide (0.139 g, 2.48 mmol) in absolute ethanol (3.0 mL) was added to a pressure tube charged with 4-(ethylamino)-6-methyl-2-(methylthio)pyrimidine-5-carbaldehyde (0.229 g, 1.08 mmol), prepared using procedures similar to those described for Intermediate 1, and 2-(1H-imidazol-5-yl)acetonitrile (0.174 g, 162 mmol) and heated to 70° C. After 12 h, the reaction was allowed to cool to room temperature and concentrated in vacuo affording 8-ethyl-6-(1H-imidazol-5-yl)-4-methyl-2-(methylthio)pyrido[2,3-d]pyrimidin-7(8H)-imine as a solid. The product was used in the subsequent step without further purification.

3-Chloroperbenzoic acid (0.299 g, 1.73 mmol) was added to a solution of crude 8-ethyl-6-(1H-imidazol-5-yl)-4-methyl-2-(methylthio)pyrido[2,3-d]pyrimidin-7(8H)-one (0.260 g, 0.866 mmol) in dichloromethane (10.0 mL) at room temperature. After 1.5 h, the reaction was diluted with dichloromethane (50 mL) and washed twice with saturated NaHCO$_3$, followed by brine. The organic phase was separated and dried over Na$_2$SO$_4$, filtered, and concentrated in vacuo. The corresponding sulfone was used in the subsequent step without further purification.

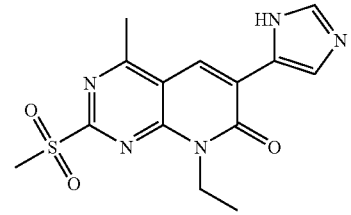

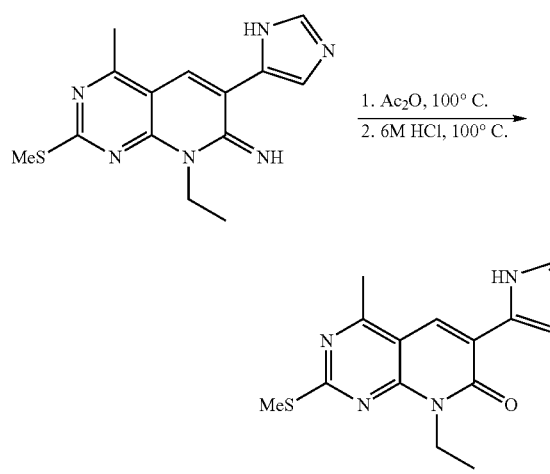

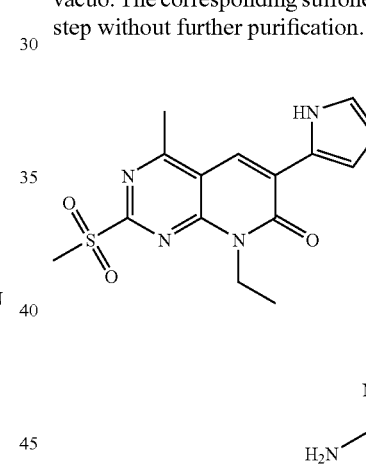

Acetic anhydride (15.0 mL) was added to a flask charged with crude 8-ethyl-6-(1H-imidazol-5-yl)-4-methyl-2-(methylthio)pyrido[2,3-d]pyrimidin-7(8H)-imine and heated to 100° C. After 30 minutes, the reaction was allowed to cool to room temperature and concentrated in vacuo. The acetylated residue was then treated with 6 N HCl (16 mL) and heated to 95° C. for 30 minutes then transferred to a large flask. A saturated solution of NaHCO$_3$ (150 mL) was added at 0° C. to about pH=8.0. The aqueous phase was washed thrice with ethyl acetate (100 mL) and the organic layers combined, then washed with brine and dried over Na$_2$SO$_4$. The drying agent was filtered off and the organic layers were concentrated in vacuo to afford crude 8-ethyl-6-(1H-imidazol-5-yl)-4-methyl-2-(methylthio)pyrido[2,3-d]pyrimidin-7(8H)-one which was used in the subsequent step without further purification.

Concentrated aqueous ammonium hydroxide (400 µL) was added to a solution of the sulfone in dioxane (10 mL) at 0° C. The reaction flask sealed, and allowed to warm to room temperature upon standing overnight. The reaction was concentrated in vacuo and purified on reverse phase HPLC (acetonitrile: water 0.1% TFA, 20-60% gradient). The fractions containing product were collected and concentrated to one half volume and poured into saturated NaHCO$_3$ (50 mL). The aqueous phase was washed trice with ethyl acetate (50 mL) and dried over Na$_2$SO$_4$, filtered, and concentrated in vacuo. The residue was triturated with methylene chloride and ethyl acetate to afford 2-amino-8-ethyl-6-(1H-imidazol-5-yl)-4-methylpyrido[2,3-d]pyrimidin-7(8H)-one (29 mg, 12% yield) as a light yellow solid: $^1$H NMR (400 MHz, CH$_3$OH-d$_4$): δ 8.52 (bs, 1H), 7.88 (bs, 1H), 7.76 (s, 1H), 4.30 (q, J=6.8 Hz, 2H), 2.65 (s, 3H), 1.29 (t, J=6.8 Hz, 3H); MS (EI) for C$_{13}$H$_{14}$N$_6$O: 271.0 (MH$^+$).

Example 11

2-Amino-8-ethyl-4-methyl-6-(1H-1,2,3-triazol-5-yl)pyrido[2,3-d]pyrimidin-7(8H)-one

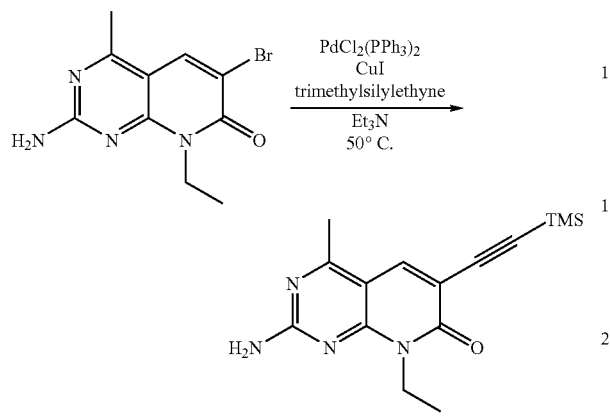

Trimethylsilylethyne (1.44 mL, 10.2 mmol) was added to a pressure tube charged with 2-amino-6-bromo-8-ethyl-4-methylpyrido[2,3-d]pyrimidin-7(8H)-one (1.58 g, 5.59 mmol) from above, CuI (0.053 g, 0.279 mmol), and PdCl$_2$(PPh$_3$)$_2$ (0.211 g, 0.279 mmol) in triethylamine (20 mL). The pressure tube was sealed under nitrogen and heated to 50° C. 96 h. The reaction was cooled to room temperature and poured into a saturated solution of NaHCO$_3$ (150 mL), then washed four times with ethyl acetate (50 mL). The organic layers were pooled and dried over Na$_2$SO$_4$, filtered and concentrated in vacuo. The residue was purified on SiO$_2$ (2:1, methylene chloride:ethyl acetate) to afford 2-amino-8-ethyl-4-methyl-6-((trimethylsilyl)ethynyl)pyrido[2,3-d]pyrimidin-7(8H)-one (1.09 g, 65% yield) as an off white solid.

Potassium carbonate (1.00 g, 7.28 mmol) was added to a flask charged with 2-amino-8-ethyl-4-methyl-6-((trimethylsilyl)ethynyl)pyrido[2,3-d]pyrimidin-7(8H)-one (1.09 g, 3.64 mmol) in anhydrous methanol (15 mL). The reaction was stirred at room temperature under nitrogen for 16 h. The reaction was concentrated to one half volume and the yellow precipitate collected by vacuum filtration to afford 2-amino-8-ethyl-6-ethynyl-4-methylpyrido[2,3-d]pyrimidin-7(8H)-one.

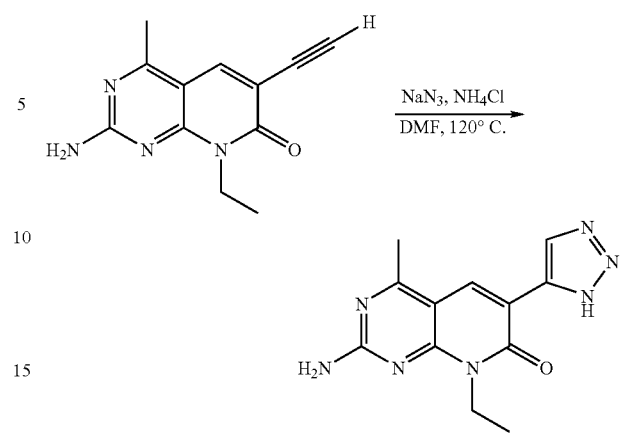

Anhydrous DMF (5.0 mL) was added to a flask charged with 2-amino-8-ethyl-6-ethynyl-4-methylpyrido[2,3-d]pyrimidin-7(8H)-one (0.204 g, 0.894 mmol), sodium azide (0.070 g, 1.07 mmol), and ammonium chloride (0.057 g, 1.07 mmol). The reaction was capped under nitrogen and heated to 120° C. After 48 h, the reaction was cooled to room temperature and concentrated in vacuo. The residue was purified on reverse phase HPLC (acetonitrile: water 0.1% TFA, 20-60% gradient). The fractions containing product were collected and concentrated to one half volume and poured into saturated NaHCO$_3$ (50 mL). The aqueous phase was washed trice with ethyl acetate (50 mL) and dried over Na$_2$SO$_4$, filtered, and concentrated in vacuo. The residue was triturated with methylene chloride and ethyl acetate to afford 2-amino-8-ethyl-4-methyl-6-(1H-1,2,3-triazol-5-yl)pyrido[2,3-d]pyrimidin-7(8H)-one (14 mg, 6% yield) as a light yellow solid: $^1$H NMR (400 MHz, DMSO-d$_6$): δ 8.55 (bs, 1H), 8.41 (bs, 1H), 7.32 (bs, 2H), 4.37 (q, J=7.2 Hz, 2H), 2.60 (s, 3H), 1.21 (t, J=7.2 Hz, 3H); MS (EI) for C$_{12}$H$_{13}$N$_7$O: 272.0 (MH$^+$).

Example 12

2-Amino-8-ethyl-4-methyl-6-(1H-tetrazol-5-yl)pyrido[2,3-d]pyrimidin-7(8H)-one

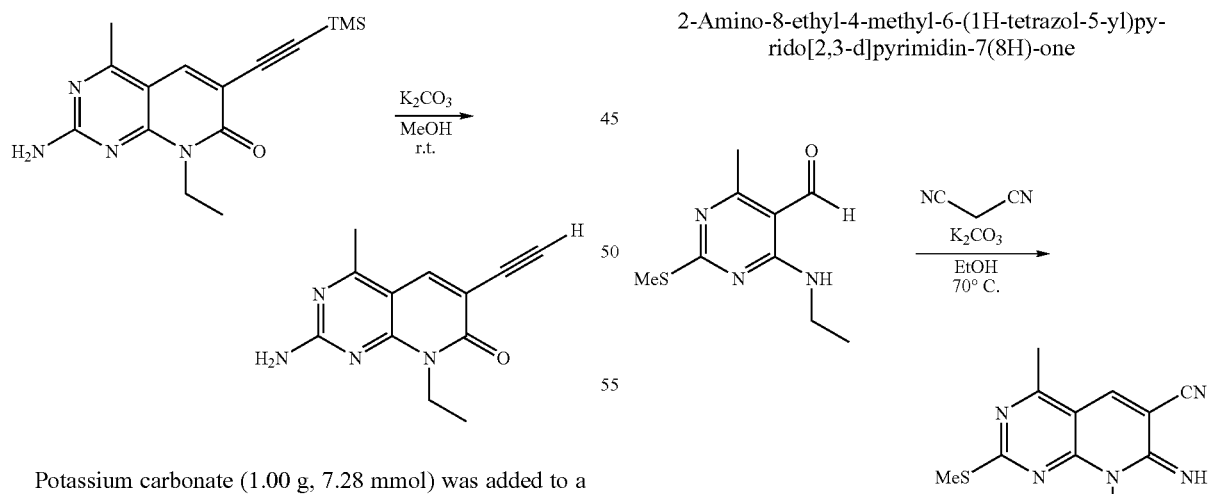

Potassium carbonate (0.539 g, 3.90 mmol) was added to a suspension of 4-(ethylamino)-6-methyl-2-(methylthio)pyrimidine-5-carbaldehyde (0.413 g, 1.95 mmol) from above, and malononitrile (0.194 g, 2.93 mmol) in absolute ethanol (15.0 mL) and heated to 70° C. After one h, the reaction was allowed to cool to room temperature and concentrated in vacuo. The residue was diluted with ethyl acetate (50 mL) and washed with saturated NaHCO₃ (50 mL), and brine. The organic phase was separated and concentrated in vacuo. The residue was precipitated with ethyl acetate and hexanes to give 8-ethyl-7-imino-4-methyl-2-(methylthio)-7,8-dihydropyrido[2,3-d]pyrimidine-6-carbonitrile as a brown solid that was used in the subsequent step without further purification.

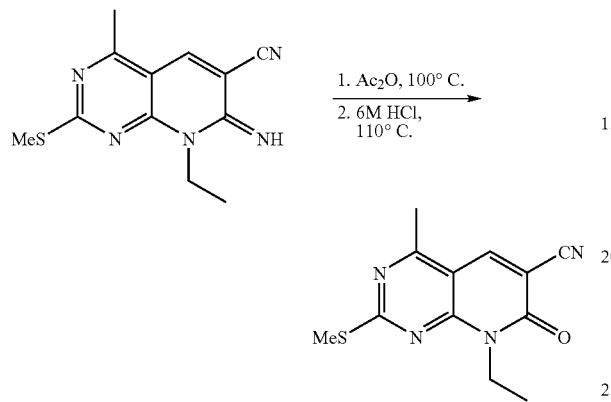

Acetic anhydride (10.0 mL) was added to a flask charged with 8-ethyl-7-imino-4-methyl-2-(methylthio)-7,8-dihydropyrido[2,3-d]pyrimidine-6-carbonitrile (0.506 g, 1.95 mmol) and heated to 100° C. After one h, the reaction was allowed to cool to room temperature and concentrated in vacuo. The acetylated residue was then treated with 6 N HCl (40 mL) and heated to 95° C. for one hour then transferred to a large flask. A saturated solution of NaHCO₃ (500 mL) was added slowly at 0° C. until a pH 8.0 was achieved. The aqueous phase was washed thrice with ethyl acetate (100 mL) and the organic layers combined, then washed with brine and dried over Na₂SO₄. The drying agent was filtered and concentrated in vacuo to afford crude 8-ethyl-4-methyl-2-(methylthio)-7-oxo-7,8-dihydropyrido[2,3-d]pyrimidine-6-carbonitrile which was used in the subsequent step without further purification.

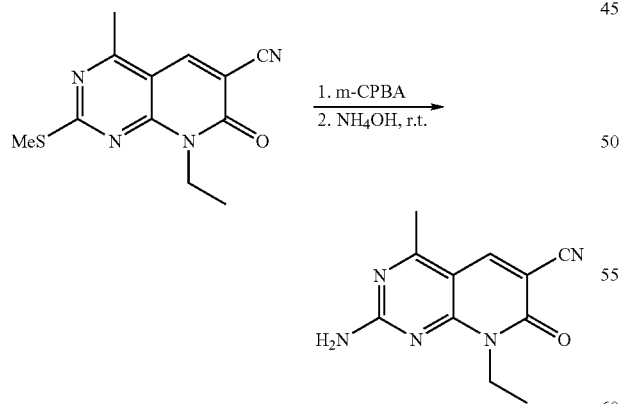

3-Chloroperbenzoic acid (1.00 g, 5.85 mmol) was added to a solution of crude 8-ethyl-4-methyl-2-(methylo)-7-oxo-7,8-dihydropyrido[2,3-d]pyrimidine-6-carbonitrile (0.507 g, 1.95 mmol) in dichloromethane (30.0 mL) at room temperature. After 2.5 hours, the reaction was diluted with dichloromethane (50 mL) and washed twice with saturated NaHCO₃, followed by brine. The organic phase was separated and dried over Na₂SO₄, filtered, and concentrated in vacuo. 2-Amino-8-ethyl-4-methyl-7-oxo-7,8-dihydropyrido[2,3-d]pyrimidine-6-carbonitrile was used in the subsequent step without further purification.

Ammonium hydroxide (500 μL) was added to a solution of the above sulfone in dioxane (10 mL) at 0° C. The reaction flask sealed, and allowed to warm to room temperature upon standing overnight. The reaction was concentrated in vacuo triturated with ethyl acetate to afford the product which was used in the subsequent step without further purification.

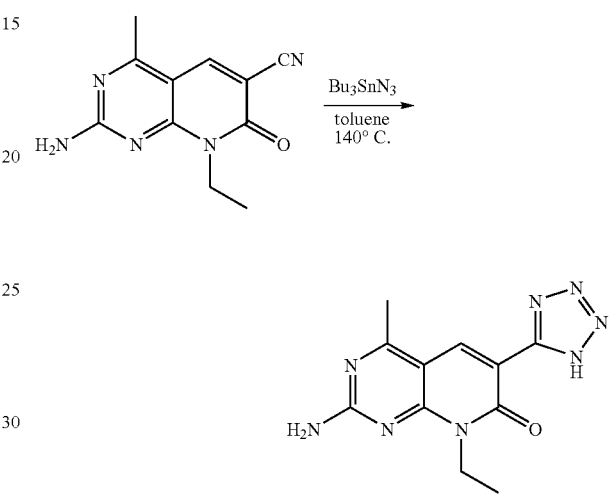

Tributyltin azide (660 μL, 2.41 mmol) was added to a flask charged with 2-amino-8-ethyl-4-methyl-7-oxo-7,8-dihydropyrido[2,3-d]pyrimidine-6-carbonitrile (0.184 g, 0.803 mmol) in anhydrous toluene (5.0 mL). The reaction was fitted with a reflux condenser and heated to 140° C. under a nitrogen atmosphere. After 20 h, the reaction was cooled to room temperature and the precipitate collected by vacuum filtration and washed with absolute ethanol to give 2-amino-8-ethyl-4-methyl-6-(1H-tetrazol-5-yl)pyrido[2,3-d]pyrimidin-7(8H)-one (98 mg, 45% yield) as a light brown solid: ¹H NMR (400 MHz, 20% DCl in D₂O): δ 6.97 (s, 1H), 2.42 (q, J=7.2 Hz, 2H), 0.953 (s, 3H), −0.73 (t, J=7.2 Hz, 3H); MS (EI) for $C_{11}H_{11}N_8O$: 271.0 (MH⁺).

Example 13

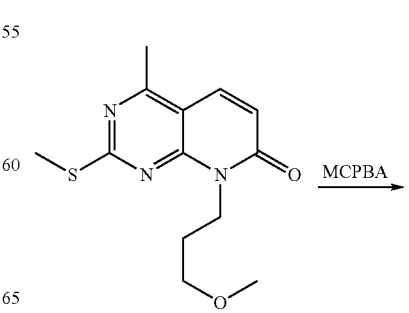

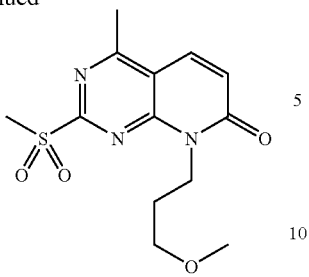

A mixture of 8-(3-methoxypropyl)-4-methyl-2-(methylthio)pyrido[2,3-d]pyrimidin-7(8H)-one (0.36 g, 1.29 mmol), prepared using procedures similar to those described in Example 1, dichloromethane (10 mL), and 77% 3-chloroperbenzoic acid with water (0.723 g, 3.23 mmol) was stirred for 1 h. The mixture was diluted with dichloromethane, washed with sat. sodium bicarbonate (3 times), brine, dried over sodium sulfate, and DCM was removed under reduced pressure. The crude 8-(3-methoxypropyl)-4-methyl-2-(methylsulfonyl)pyrido[2,3-d]pyrimidin-7(8H)-one was used without further purification for subsequent step.

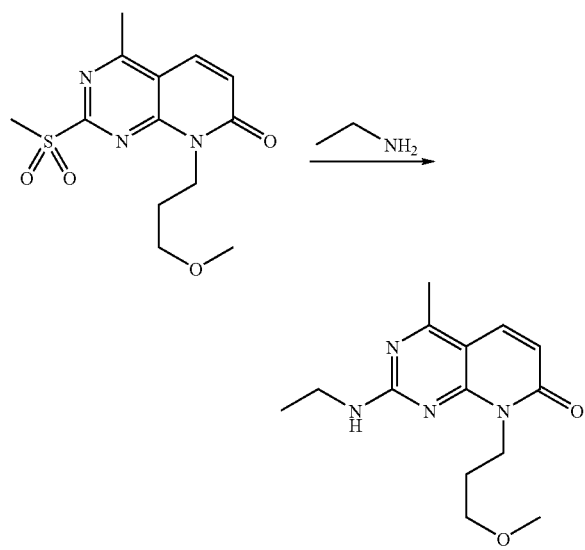

8-(3-methoxypropyl)-4-methyl-2-(methylsulfonyl)pyrido[2,3-d]pyrimidin-7(8H)-one, and a solution of 2M ethylamine in THF (20 mL) was stirred for 2 h. THF was removed under reduced pressure and the crude product was purified by flash column chromatography to give 2-(ethylamino)-8-(3-methoxypropyl)-4-methylpyrido[2,3-d]pyrimidin-7(8H)-one (0.18 g, 50% yield over 2 steps).

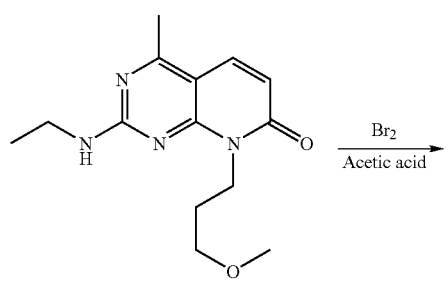

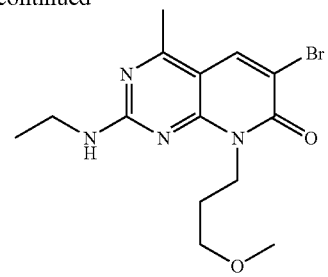

To a solution of 2-(ethylamino)-8-(3-methoxypropyl)-4-methylpyrido[2,3-d]pyrimidin-7(8H)-one (0.18 g, 0.65 mmol), acetic acid (5 mL) and dichloromethane (3 mL) was added bromine (36 ul, 0.7 mmol). The mixture was stirred for 5 minutes, and then diluted with DCM and water. The organic layer was washed with sat. sodium bicarbonate (3 times), brine, dried over sodium sulfate, filtered and concentrated under reduced pressure. The crude product was purified by flash column chromatography to gave 0.13 g (56% yield) of 6-bromo-2-(ethylamino)-8-(3-methoxypropyl)-4-methylpyrido[2,3-d]pyrimidin-7(8H)-one. $^1$H NMR (400 MHz, CDCl$_3$) δ 8.09 (s, 1H), 5.44 (Br. s, 1H), 4.55 (m, 2H), 3.54-3.47 (m, 4H), 3.33 (s, 3H), 2.53 (s, 3H), 2.05-2.00 (m, 2H), 1.30-1.23 (m, 3H); MS (E) for C$_{14}$H$_{19}$BrN$_4$O$_2$: 355 (MH$^+$).

Using the same or analogous synthetic techniques and substituting with appropriate reagents, the following compounds were prepared:

Example 13a 6-bromo-8-(2-ethoxyethyl)-2-(ethylamino)-4-methylpyrido[2,3-d]pyrimidin-7(8H)-one: $^1$H NMR (400 MHz, CDCl$_3$) δ 8.09 (s, 1H), 5.37 (Br. s, 1H), 4.67 (m, 2H), 3.74 (m, 2H), 3.61-3.56 (t, 2H), 3.51 (m, 2H), 2.53 (s, 3H), 1.29-1.25 (t, 3H), 1.19-1.15 (t, 3H); MS (EI) for C$_{14}$H$_{19}$BrN$_4$O$_2$: 355 (MH+).

Example 13b 6-bromo-8-(3-ethoxypropyl)-2-(ethylamino)-4-methylpyrido[2,3-d]pyrimidin-7(8H)-one: $^1$H NMR (400 MHz, CDCl$_3$) δ 8.09 (s, 1H), 5.37 (Br. s, 1H), 4.53 (m, 2H), 3.52 (m, 4H), 3.48-3.43 (m, 2H), 2.53 (s, 3H), 2.04-2.00 (m, 2H), 1.29-1.25 (t, 3H), 1.19-1.15 (t, 3H); MS (EI) for C$_{15}$H$_{21}$BrN$_4$O$_2$: 369 (MH+).

Example 13c 6-bromo-2-(ethylamino)-8-(3-isopropoxypropyl)-4-methylpyrido[2,3-d]pyrimidin-7(8H)-one: $^1$H NMR (400 MHz, CDCl$_3$) δ 8.09 (s, 1H), 5.37 (Br. s, 1H), 4.53 (m, 2H), 3.59-3.49 (m, 5H), 2.52 (s, 3H), 2.01-1.98 (m, 2H), 1.28-1.25 (t, 3H), 1.13-1.11 (t, 6H); MS (EI) for C$_{16}$H$_{23}$BrN$_4$O$_2$: 383 (MH+).

Example 14

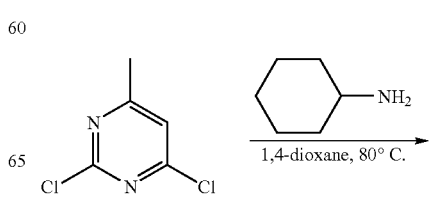

-continued

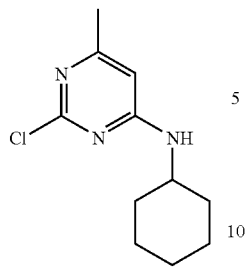

A mixture of 2,4-dichloro-6-methylpyrimidine (Aldrich, 5 g, 30 mmol), cyclohexylamine (3 g, 30 mmol) and DIEA (10 mL) was stirred at 80° C. for 12 h. The volatile material was removed under reduced pressure. The residue was loaded on a silica gel column, and was eluted with hexanes/ethyl acetate (3:1). 8-cyclohexyl-2-(ethylamino)-4-methyl-6-(thiopheN-2-yl)pyrido[2,3-d]pyrimidin-7(8H)-one was obtained as colorless oil (2.8 g, 41% yield).

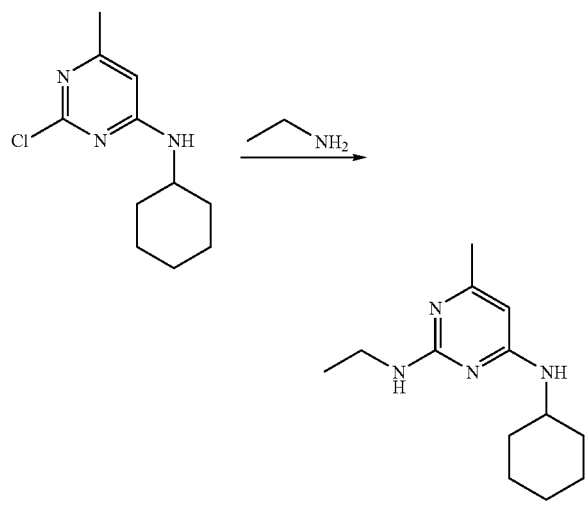

The product was reacted with a solution of ethylamine (10 equiv.) in THF at 100° C. for 12 h. The crude 2-ethylamino-4-cyclohexylamino-6-methylpyrimidine was obtained from a standard workup and was used in the next step.

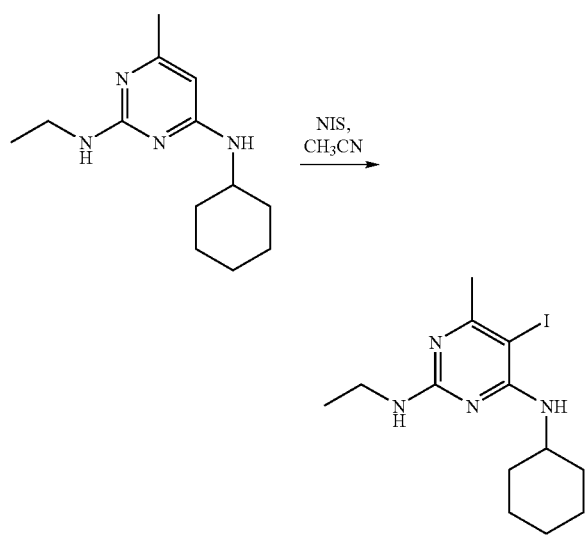

To a solution of 2-ethylamino-4-cyclohexylamino-6-methylpyrimidine (600 mg, 2.56 mmol) in CH$_3$CN (10 mL) was added N-iodosuccinimide (NIS, 658 mg, 2.92 mmol). The reaction was stirred for 2 h at room temperature. After removal of the solvent, the residue was dissolved in EtOAc. The organic phase was then washed with sodium bisulfite, brine, and dried over Na$_2$SO$_4$. Purification by flash column chromatography gave 660 mg (73% yield) of 2-ethylamino-4-cyclohexylamino-5-iodo-6-methylpyrimidine.

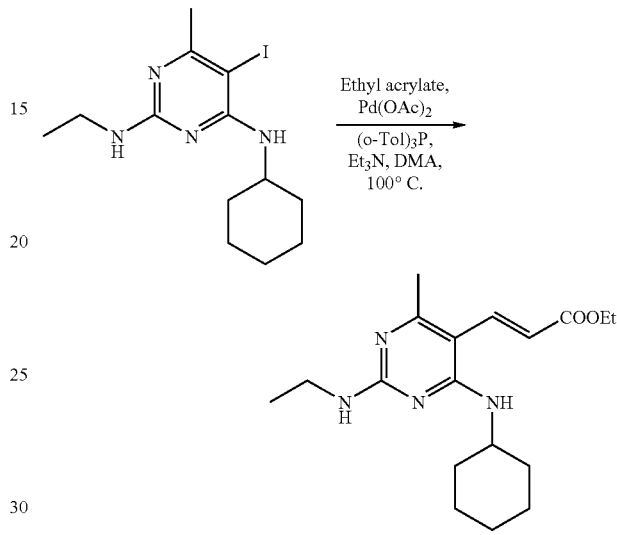

To a solution of 2-ethylamino-4-cyclohexylamino-5-iodo-6-methylpyrimidine (660 mg, 1.83 mmol) in DMA (7 mL) was added ethyl acrylate (458 mg, 4.58 mmol), Pd(OAc)$_2$ (121 mg, 0.18 mmol), (o-Tol)$_3$P (110 mg, 0.37 mmol), and Et$_3$N (740 mg, 7.32 mmol). The mixture was then stirred at 100° C. for 12 h under N$_2$. Standard workup and purification by column chromatography gave 411 mg (67% yield) of (E)-ethyl 3-(4-(cyclohexylamino)-2-(ethylamino)-6-methylpyrimidin-5-yl)acrylate

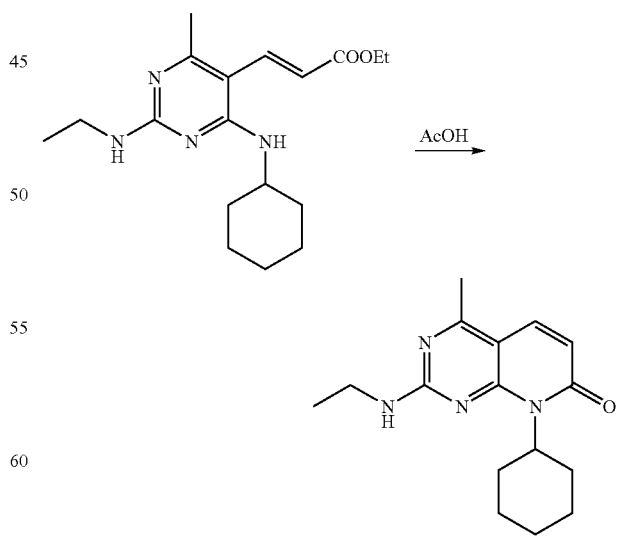

(E)-ethyl 3-(4-(cyclohexylamino)-2-(ethylamino)-6-methylpyrimidin-5-yl)acrylate (200 mg, 0.6 mmol) was dissolved in AcOH (2 mL). This solution was heated in a sealed tube at 186° C. for 17 h. Standard workup and purification by column chromatography gave 65 mg (38% yield) of 8-cyclohexyl-2-(ethylamino)-4-methylpyrido[2,3-d]pyrimidin-7(8H)-one.

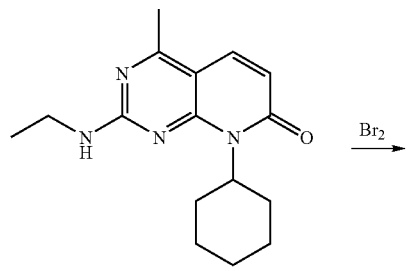 

To 8-cyclohexyl-2-(ethylamino)-4-methylpyrido[2,3-d]pyrimidin-7(8H)-one in AcOH and CH₂Cl₂ was added Br₂ (22 uL, 0.42 mmol) at 80° C. Standard workup and purification by column chromatography gave 65 mg (0.17 mmol, 80% yield) of 6-bromo-8-cyclohexyl-2-(ethylamino)-4-methylpyrido[2,3-d]pyrimidin-7(8H)-one.

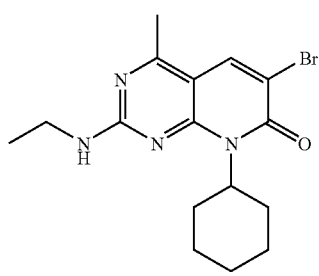

The bromide (65 mg, 0.17 mmol) obtained above was reacted with 2-thiopheneboronic acid (45 mg, 0.36 mmol) in the presence of Pd(PPh₃)₄ (20 mg, 0.018 mmol) and Na₂CO₃ (38 mg, 0.36 mmol) in 1,4-dioxane/H₂O (1:1) at 100° C. for 2 h. Removal of solvents and purification by column chromatography gave 33 mg (50% yield) of 8-cyclohexyl-2-(ethylamino)-4-methyl-6-(thiopheN-2-yl)pyrido[2,3-d]pyrimidin-7(8H)-one. ¹H NMR (400 MHz, DMSO-d₆) δ8.01 (br s, 1H), 7.60 (m, 1H), 7.37 (m, 1H), 7.10 (m, 1H), 5.60-5.40 (m, 1H), 3.55 (m, 2H), 2.85 (m, 1H), 2.61 (s, 3H), 1.90 (m, 2H), 1.71 (m, 4H), 1.43 (m, 2H), 1.30-1.2 (m, 2H), 1.30 (t, 3H); MS (EI) for C₂₀H₂₄N₄OS: 369 (MH+).

Using the same or analogous synthetic techniques and substituting with appropriate reagents, the following compound was prepared:

Example 14a 6-bromo-8-cyclopropyl-2-(ethylamino)-4-methylpyrido[2,3-d]pyrimidin-7(8H)-one: ¹H NMR (400 MHz, CDCl₃) δ8.06 (s, 1H), 5.37 (br s, 1H), 3.54 (m, 2H), 2.94 (br s, 1H), 2.51 (s, 3H), 1.31-1.25 (m, 5H), 0.91 (br s, 2H); MS (EI) for C₁₃H₁₅BrN₄O: 323 (MH+).

Example 15

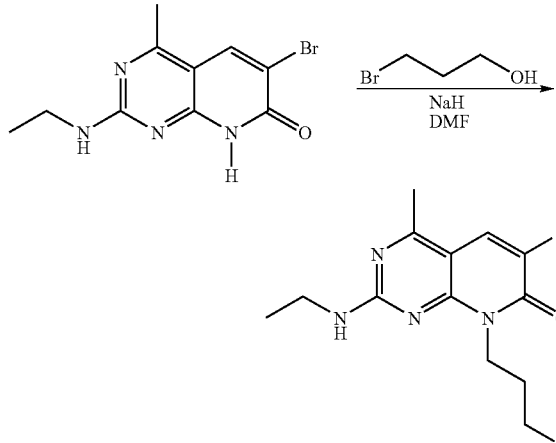

To a solution of 6-bromo-2-(ethylamino)-4-methylpyrido[2,3-d]pyrimidin-7(8H)-one (100 mg, 0.35 mmol) in DMF (2 mL), prepared using procedures analogous to those described in Example 14, was added NaH (30 mg, 60%, 0.7 mmol). The mixture was stirred for 30 min at room temperature and was warmed to 70° C. 3-Bromopropanol (48 mg, 0.35 mmol) was then added. The stirring was continued for 12 h. Standard workup and purification by column chromatography gave 33 mg (27% yield) of 6-bromo-2-(ethylamino)-8-(3-hydroxypropyl)-4-methylpyrido[2,3-d]pyrimidin-7(8H)-one. ¹H NMR (400 MHz, CDCl₃) δ 8.13 (s, 1H), 5.42 (br s, 1H), 4.59 (br s, 2H), 3.50-3.47 (m, 5H), 2.55 (s, 3H), 2.02 (br s, 2H), 1.28 (t, 3H); MS (EI) for C₁₃H₁₇BrN₄O₂: 341 (MH⁺).

Using the same or analogous synthetic techniques and substituting with appropriate reagents, the following compounds were prepared:

Example 15a 6-bromo-2-(ethylamino)-8-(2-hydroxyethyl)-4-methylpyrido[2,3-d]pyrimidin-7(8H)-one: ¹H NMR (400 MHz, DMSO-d6) δ 8.38 (s, 1H), 4.82 (br s, 1H), 4.40 (br s, 2H), 3.62-3.55 (m, 2H), 3.40-3.20 (m, 3H), 2.55 (s, 3H), 1.15 (t, 3H); MS (EI) for C₁₂H₁₅BrN₄O₂: 327 (MH⁺).

Example 15b 6-bromo-2-(ethylamino)-4-methyl-8-(2-(piperidin-1-yl)ethyl)pyrido[2,3-d]pyrimidin-7(8H)-one: ¹H NMR (400 MHz, CDCl₃) δ 8.08 (s, 1H), 5.39 (br s, 1H), 4.59 (br s, 2H),

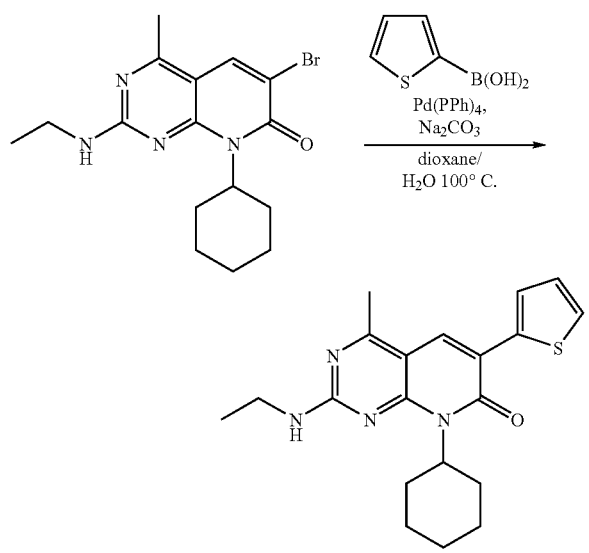

3.55-3.40 (m, 2H), 2.70-2.50 (m, 6H), 2.52 (s, 3H), 1.62-1.58 (m, 4H), 1.46-1.40 (m, 2H), 1.27 (t, 3H); MS (EI) for $C_{17}H_{24}BrN_5O$: 394 (MH+).

BIOLOGICAL EXAMPLES

Biological Example 1

PI3Kalpha Luciferase-Coupled Chemiluminescence Assay Protocol

PI3Kα activity is measured as the percent of ATP consumed following the kinase reaction using luciferase-luciferiN-coupled chemiluminescence. Reactions were conducted in 384-well white, medium binding microtiter plates (Greiner). Kinase reactions were initiated by combining test compounds, ATP, substrate (PIP2), and kinase in a 20 µL volume in a buffer solution. The standard PI3Kalpha assay buffer is composed 50 mM Tris, pH 7.5, 1 mM EGTA, 10 mM $MgCl_2$, 1 mM DTT and 0.03% CHAPS. The standard assay concentrations for enzyme, ATP, and substrate are 0.5-1.1 nM, 1 M, and 7.5 µM, respectively. The reaction mixture was incubated at ambient temperature for approximately 2 h. Following the kinase reaction, a 10 µL aliquot of luciferase-luciferin mix (Promega Kinase-Glo) was added and the chemiluminescence signal measured using a Victor2 plate reader (Perkin Elmer). Total ATP consumption was limited to 40-60% and IC50 values of control compounds correlate well with literature references.

Certain compounds of the invention were tested in this assay and demonstrated the ability to bind to PI3K. For example, in one embodiment of the invention, the PI3K inhibitor is selected from the compounds in Table 1 having a PI3K-binding affinity of about 9 µM or less. In another embodiment, the PI3K inhibitor is selected from the compounds in Table 1 having a PI3K-binding affinity of about 5 µM or less. In another embodiment, the PI3K inhibitor is selected from the compounds in Table 1 having a PI3K-binding affinity of about 3 µM or less. In another embodiment, the PI3K inhibitor is selected from the compounds in Table 1 having a PI3K-binding affinity of about 1.5 µM or less. In another embodiment, the PI3K inhibitor is selected from the compounds in Table 1 having a PI3K-binding affinity of about 1 µM or less. In another embodiment, the PI3K inhibitor is selected from the compounds in Table 1 having a PI3K-binding affinity of about 0.6 µM or less. In another embodiment, the PI3K inhibitor is selected from the compounds in Table 1 having a PI3K-binding affinity of about 0.3 µM or less. In another embodiment, the PI3K inhibitor is selected from the compounds in Table 1 having a PI3K-binding affinity of about 0.2 µM or less. In another embodiment, the PI3K inhibitor is selected from the compounds in Table 1 having a PI3K-binding affinity of about 0.1 µM or less. In another embodiment, the PI3K inhibitor is selected from the compounds in Table 1 having a PI3K-binding affinity of about 0.04 µM or less. In another embodiment, the PI3K inhibitor is selected from the compounds in Table 1 having a PI3K-binding affinity of about 0.020 µM or less.

Biological Example 2

Phospho AKT assayPC3 cells were seeded on 6-well plates at 150,000 cells/well. Cells were cultured for 3 days, then treated with compounds in serum-free medium for 3 hr. EGF (100 ng/mL) was added for the last 10 min. Cells were lysed in TENN buffer. Phospho T308 Akt and total Akt were quantified by ELISA performed according to the Biosource assay protocol. The readings of phospho Akt were normalized to total Akt readings.

Biological Example 3

Phospho S6 Assay

PC3 cells were seeded on 96-well plates at 8,000 cells/well. For each experiment, cells were seeded and treated in duplicated plates: one plate for phospho S6 CellELISA, and one plate for total S6 CellELISA. Cells were cultured on the plates for 3 days, then treated with compounds in serum-free medium for 3 hr in triplicate. Cells were fixed with 4% formaldehyde, quenched with 0.6% $H_2O_2$, blocked with 5% BSA, incubated with either phospho S6 antibody or total S6 antibody overnight, incubated with goat-anti-rabbit-IgG-HRP for 1 hr, and developed in chemiluminescent substrate.

Biological Example 4

$PIP_3$ Assay

MCF-7 cells grown in 10-cm dishes were starved for 3 hours in DMEM, and then treated with compounds for 20 minutes. In the last 2 minutes of the incubation with the compounds, EGF (100 ng/mL) was added to stimulate the production of PIP3. The medium was aspirated and the cells were scraped with 10% trichloroacetic acid. The lipids were extracted from the pellet after the cell lysates were centrifuged. PIP3 in the cellular lipid extraction was quantified with the AlphaScreen assay in which Grp1-PH is used as the PIP3 specific probe. The amount of cellular PIP3 was calculated from the standard curve of $diC_8$ PI (3,4,5) P3.

Biological Example 5-10

In Vivo Models

Female and male athymic nude mice (NCr) 5-8 weeks of age and weighing approximately 20 g were used in the following model. Prior to initiation of a study, the animals were allowed to acclimate for a minimum of 48 h. During these studies, animals were provided food and water ad libitum and housed in a room conditioned at 70-75° F. and 60% relative humidity. A 12 h light and 12 h dark cycle was maintained with automatic timers. All animals were examined daily for compound-induced or tumor-related deaths.

PC-3 human prostate adenocarcinoma cells were cultured in vitro in DMEM (Mediatech) supplemented with 20% Fetal Bovine Serum (Hyclone), PenicilliN-Streptomycin and non-essential amino acids at 37° C. in a humidified 5% $CO_2$ atmosphere. On day 0, cells were harvested by trypsinization and $3×10^6$ cells (passage 13, 99% viability) in 0.1 mL of ice-cold Hank's balanced salt solution were implanted subcutaneously into the hindflank of 5-8 week old male nude mice. A transponder was implanted in each mouse for identification, and animals were monitored daily for clinical symptoms and survival. Body weights were recorded daily.

U-87 MG human glioblastoma cells were cultured in vitro in DMEM (Mediatech) supplemented with 10% Fetal Bovine Serum (Hyclone), PenicilliN-Streptomycin and non-essential amino acids at 37° C. in a humidified 5% $CO_2$ atmosphere. On day 0, cells were harvested by trypsinization and $2×10^6$ cells (passage 5, 96% viability) in 0.1 mL of ice-cold Hank's balanced salt solution were implanted intradermally into the hindflank of 5-8 week old female nude mice. A transponder was implanted in each mouse for identification, and animals were monitored daily for clinical symptoms and survival. Body weights were recorded daily.

A549 human lung carcinoma cells were cultured in vitro in DMEM (Mediatech) supplemented with 10% Fetal Bovine Serum (Hyclone), PenicilliN-Streptomycin and non-essential amino acids at 37° C. in a humidified 5% $CO_2$ atmosphere. On day 0, cells were harvested by trypsinization and $10 \times 10^6$ cells (passage 12, 99% viability) in 0.1 mL of ice-cold Hank's balanced salt solution were implanted intradermally into the hindflank of 5-8 week old female nude mice. A transponder was implanted in each mouse for identification, and animals were monitored daily for clinical symptoms and survival. Body weights were recorded daily.

A2058 human melanoma cells were cultured in vitro in DMEM (Mediatech) supplemented with 10% Fetal Bovine Serum (Hyclone), PenicilliN-Streptomycin and non-essential amino acids at 37° C. in a humidified, 5% $CO_2$ atmosphere. On day 0, cells were harvested by trypsinization and $3 \times 10^6$ cells (passage 3, 95% viability) in 0.1 mL ice-cold Hank's balanced salt solution were implanted intradermally in the hind-flank of 5-8 week old female athymic nude mice. A transponder was implanted in each mouse for identification, and animals were monitored daily for clinical symptoms and survival. Body weights were recorded daily.

WM-2664 human melanoma cells were cultured in vitro in DMEM (Mediatech) supplemented with 10% Fetal Bovine Serum (Hyclone), PenicilliN-Streptomycin and non-essential amino acids at 37° C. in a humidified, 5% $CO_2$ atmosphere. On day 0, cells were harvested by trypsinization and $3 \times 10^6$ cells (passage 5, 99% viability) in 0.1 mL ice-cold Hank's balanced salt solution were implanted intradermally in the hind-flank of 5-8 week old female athymic nude mice. A transponder was implanted in each mouse for identification, and animals were monitored daily for clinical symptoms and survival. Body weights were recorded daily.

For subcutaneous or intradermal tumors, the mean tumor weight of each animal in the respective control and treatment groups was determined twice weekly during the study. Tumor weight (TW) was determined by measuring-perpendicular diameters with a caliper, using the following formula:

$$\text{tumor weight(mg)} = [\text{tumor volume} = \text{length(mm)} \times \text{width}^2(\text{mm}^2)]/2$$

These data were recorded and plotted on a tumor weight vs. days post-implantation line graph and presented graphically as an indication of tumor growth rates. Percent inhibition of tumor growth (TGI) is determined with the following formula:

$$\left(1 - \left(\frac{(X_f - X_0)}{(Y_f - X_0)}\right)\right) * 100$$

where $X_0$=average TW of all tumors on group day
$X_f$=TW of treated group on Day f
$Y_f$=TW of vehicle control group on Day f If tumors regress below their starting sizes, then the percent tumor regression is determined with the following formula:

$$\left(\frac{(X_0 - X_f)}{X_0}\right) * 100$$

Tumor size is calculated individually for each tumor to obtain a mean±SEM value for each experimental group. Statistical significance is determined using the 2-tailed Student's t-test (significance defined as P<0.05).

PHARMACEUTICAL COMPOSITION EXAMPLES

The following are representative pharmaceutical formulations containing a compound of Formula I.

Tablet Formulation
The following ingredients are mixed intimately and pressed into single scored tablets.

| Ingredient | Quantity per tablet, mg |
| --- | --- |
| compound of this invention | 400 |
| Cornstarch | 50 |
| croscarmellose sodium | 25 |
| Lactose | 120 |
| magnesium stearate | 5 |

Capsule Formulation
The following ingredients are mixed intimately and loaded into a hard-shell gelatin capsule.

| Ingredient | Quantity per tablet, mg |
| --- | --- |
| compound of this invention | 200 |
| lactose, spray-dried | 148 |
| magnesium stearate | 2 |

Suspension Formulation
The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| Flavoring | 0.035 mL |
| Colorings | 0.5 mg |
| distilled water | q.s. to 100 mL |

Injectable Formulation
The following ingredients are mixed to form an injectable formulation.

| Ingredient | Amount |
| --- | --- |
| compound of this invention | 1.2 g |
| sodium acetate buffer solution | 0.4 M 2.0 mL |
| HCl (1 N) or NaOH (1 M) | q.s. to suitable pH |
| water (distilled, sterile) | q.s. to 20 mL |

All of the above ingredients, except water, are combined and heated to 60-70.degree. C. with stirring. A sufficient quantity of water at 60.degree. C. is then added with vigorous stirring to emulsify the ingredients, and water then added q.s. to 100 g.

| Suppository Formulation |
|---|
| A suppository of total weight 2.5 g is prepared by mixing the compound of the invention with Witepsol.RTM. H-15 (triglycerides of saturated vegetable fatty acid; Riches-Nelson, Inc., New York), and has the following composition: |

| Ingredient | Quantity per tablet, mg |
|---|---|
| compound of this invention | 500 |
| Witepsol ® H-15 | balance |

The foregoing invention has been described in some detail by way of illustration and example, for purposes of clarity and understanding. The invention has been described with reference to various specific embodiments and techniques. However, it should be understood that many variations and modifications may be made while remaining within the spirit and scope of the invention. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

What is claimed is:
1. A Compound of Formula

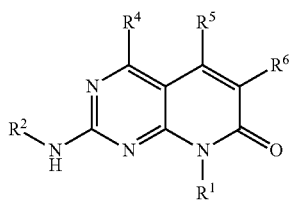

I or a pharmaceutically acceptable salt thereof, wherein
$R^1$ is alkyl, cycloalkyl, cycloalkylalkyl, aryl, arylalkyl, heterocycloalkyl, heterocycloalkylalkyl, heteroaryl or heteroarylalkyl;
$R^2$ is hydrogen or alkyl
$R^4$ is alkyl;
$R^5$ is hydrogen; and
$R^6$ is phenyl, acyl, or heteroaryl wherein the phenyl and heteroaryl are is optionally substituted with 1, 2, 3, 4, or 5 $R^9$ groups;
each $R^8$, when present, is independently hydroxy, halo, alkoxy, haloalkoxy, amino, alkylamino, dialkylaminoalkyl, or alkoxyalkylamino; and
each $R^9$, when present, is independently halo, alkyl, haloalkyl, alkoxy, haloalkoxy, cyano, amino, alkylamino, dialkylamino, alkoxyalkyl, carboxyalkyl, alkoxycarbonyl, aminoalkyl, cycloalkyl, aryl, arylalkyl, aryloxy, heterocycloalkyl, or heteroaryl and where the cycloalkyl, aryl, heterocycloalkyl, and heteroaryl, each either alone or as part of another group within R9, are independently optionally substituted with 1, 2, 3, or 4 groups selected from halo, alkyl, haloalkyl, hydroxy, alkoxy, haloalkoxy, amino, alkylamino, and dialkylamino.

2. The Compound of claim 1 where $R^1$ is alkyl, cycloalkyl, heterocycloalkylalkyl, or arylalkyl; X is —NH—; $R^2$ is hydrogen or alkyl $R^4$ is alkyl; $R^5$ is hydrogen; $R^6$ is phenyl or heteroaryl wherein the phenyl and heteroaryl are is optionally substituted with one, two, or three $R^9$ groups; each $R^8$, when present, is independently amino, alkylamino, dialkylamino, or halo; and each $R^8$, when present, is independently alkyl, arylalkyl, cyano, aryl, alkoxycarbonyl.

3. The Compound of claim 1 where $R^4$ is methyl.

4. The Compound of claim 1 where $R^1$ is alkyl, cycloalkyl, or heterocycloalkyl.

5. The Compound of claim 3 where $R^1$ is alkyl.

6. The Compound of claim 1 where $R^6$ is heteroaryl optionally substituted with 1, 2, or 3 $R^9$ groups.

7. The Compound of claim 6 where each $R^9$, when present, is independently alkyl, arylalkyl, cyano, aryl, alkoxycarbonyl, or halo.

8. The Compound of claim 1 where $R^6$ is pyrazolyl, imidazolyl, thienyl, thiazolyl, oxazolyl, isoxazolyl, oxadiazolyl, furanyl, pyrrolyl, triazolyl, or tetrazolyl; each of which is optionally substituted with 1, 2, or 3 $R^9$ groups.

9. The Compound of claim 1 where $R^6$ is pyrazol-3-yl, pyrazol-4-yl, pyrazol-5-yl, imidazol-2-yl, imidazol-4-yl, imidazol-5-yl, thien-2-yl, thien-3-yl, thiazol-2-yl, thiazol-4-yl, thiazol-5-yl, oxazol-2-yl, oxazol-4-yl, oxazol-5-yl, isoxazol-3-yl, isoxazol-4-yl, isoxazol-5-yl, 1,2,3-oxadiazol-4-yl, 1,2,3-oxadiazol-5-yl, 1,3,4-oxadiazol-2-yl, 1,2,4-oxadiazol-3-yl, 1,2,4-oxadiazol-5-yl, furan-2-yl, furan-3-yl, pyrrol-2-yl, pyrrol-3-yl, triazol-4-yl, triazol-5-yl, or tetrazol-5-yl; each of which is optionally substituted with 1, 2, or 3 $R^9$ groups.

10. The Compound of claim 8 where $R^4$ is methyl.

11. The Compound of claim 1 where $R^6$ is pyrazinyl, pyrimidinyl, or pyridazinyl each of which is optionally substituted with 1, 2, or 3 $R^9$ groups.

12. The Compound of claim 11 where $R^4$ is methyl.

13. The Compound of claim 1 where $R^2$ is hydrogen, $R^4$ is methyl, $R^1$ is optionally substituted alkyl, cycloalkyl, or heterocycloalkyl, and $R^6$ is heteroaryl optionally substituted with 1, 2, or 3 $R^9$ groups.

14. The Compound of claim 1 where $R^1$ is heterocycloalkyl and $R^4$ is methyl; or a single stereoisomer or mixture of stereoisomers thereof and optionally as a pharmaceutically acceptable salt thereof.

15. The Compound of claim 14 where $R^6$ is heteroaryl optionally substituted with 1, 2, or 3 $R^9$ groups.

16. The Compound of claim 1 where $R^1$ is heterocycloalkylalkyl and $R^4$ is methyl.

17. The Compound of claim 16 where $R^6$ is heteroaryl optionally substituted with 1, 2, or 3 $R^9$ groups.

18. The Compound of claim 1 where $R^2$ is alkyl optionally substituted with 1, 2, or 3 $R^9$ groups.

19. The Compound of claim 18 where $R^4$ is methyl.

20. The Compound of claim 18 where $R^1$ is alkyl or cycloalkyl.

21. The Compound of claim 18 where $R^1$ is alkyl.

22. The Compound of claim 18 where $R^6$ is heteroaryl optionally substituted with 1, 2, or 3 $R^9$ groups.

23. The Compound of claim 22 where each $R^9$, when present, is independently alkyl, arylalkyl, cyano, aryl, alkoxycarbonyl, or halo.

24. The Compound of claim 18 where $R^6$ is pyrazolyl, imidazolyl, thienyl, thiazolyl, oxazolyl, isoxazolyl, oxadiazolyl, furanyl, pyrrolyl, triazolyl, or tetrazolyl; each of which is optionally substituted with 1, 2, or 3 $R^9$ groups.

25. The Compound of claim 18 where $R^6$ is pyrazol-3-yl, pyrazol-4-yl, pyrazol-5-yl, imidazol-2-yl, imidazol-4-yl, imidazol-5-yl, thien-2-yl, thien-3-yl, thiazol-2-yl, thiazol-4-yl, thiazol-5-yl, oxazol-2-yl, oxazol-4-yl, oxazol-5-yl, isoxazol-3-yl, isoxazol-4-yl, isoxazol-5-yl, 1,2,3-oxadiazol-4-yl, 1,2,3-oxadiazol-5-yl, 1,3,4-oxadiazol-2-yl, 1,2,4-oxadiazol-3-yl, 1,2,4-oxadiazol-5-yl, furan-2-yl, furan-3-yl, pyrrol-2-yl, pyrrol-3-yl, triazol-4-yl, triazol-5-yl, or tetrazol-5-yl; each of which is optionally substituted with 1, 2, or 3 $R^9$ groups.

26. The Compound of claim 24 where $R^4$ is methyl.

27. The Compound of claim 18 where $R^6$ is pyrazinyl, pyrimidinyl, or pyridazinyl each of which is optionally substituted with 1, 2, or 3 $R^9$ groups.

28. The Compound of claim 27 where $R^4$ is methyl.

29. The Compound of claim 1 where $R^2$ is hydrogen, $R^4$ is methyl, $R^1$ is optionally substituted alkyl or cycloalkyl, and $R^6$ is heteroaryl optionally substituted with 1, 2, 3, 4, or 5 $R^2$ groups.

30. The Compound of claim 18 where $R^1$ is heterocycloalkyl or heterocycloalkylalkyl and $R^2$ is methyl.

31. The Compound of claim 30 where $R^6$ is heteroaryl optionally substituted with 1, 2, or 3 $R^9$ groups.

32. A Compound selected from
6-bromo-8-ethyl-4-methyl-2-[(1-methylethyl)amino]pyrido[2,3-d]pyrimidin-7(8H)-one;
6-bromo-2-[(1,1-dimethylethyl)amino]-8-ethyl-4-methylpyrido[2,3-d]pyrimidin-7(8H)-one;
6-bromo-2-{[3-(dimethylamino)propyl]amino}-8-ethyl-4-methylpyrido[2,3-d]pyrimidin-7(8H)-one;
6-bromo-2-(ethylamino)-4-methyl-8-(1-methylethyl)pyrido[2,3-d]pyrimidin-7(8H)-one;
6-bromo-2-(ethylamino)-4-methyl-8-[3-(methyloxy)propyl]pyrido[2,3-d]pyrimidin-7(8H)-one;
6-bromo-2-(ethylamino)-8-[2-(ethyloxy)ethyl]-4-methylpyrido[2,3-d]pyrimidin-7(8H)-one;
6-bromo-2-(ethylamino)-4-methyl-8-(2-piperidin-1-ylethyl)pyrido[2,3-d]pyrimidin-7(8H)-one;
6-bromo-2-(ethylamino)-8-[3-(ethyloxy)propyl]-4-methylpyrido[2,3-d]pyrimidin-7(8H)-one;
6-bromo-2-(ethylamino)-4-methyl-8-{3-[(1-methylethyl)oxy]propyl}pyrido[2,3-d]pyrimidin-7(8H)-one;
6-bromo-2-(ethylamino)-8-(3-hydroxypropyl)-4-methylpyrido[2,3-d]pyrimidin-7(8H)-one;
6-bromo-2-(ethylamino)-8-(2-hydroxyethyl)-4-methylpyrido[2,3-d]pyrimidin-7(8H)-one;
6-bromo-8-cyclopropyl-2-(ethylamino)-4-methylpyrido[2,3-d]pyrimidin-7(8H)-one;
6-bromo-8-cyclopentyl-2-(ethylamino)-4-methylpyrido[2,3-d]pyrimidin-7(8H)-one;
8-ethyl-4-methyl-6-(1H-pyrazol-5-yl)-2-[(2,2,2-trifluoroethyl)amino]pyrido[2,3-d]pyrimidin-7(8H)-one.

33. The Compound of claim 1 selected from
8-ethyl-2-(ethylamino)-4-methyl-6-phenylpyrido[2,3-d]pyrimidin-7(8H)-one;
6-biphenyl-4-yl-8-ethyl-2-(ethylamino)-4-methylpyrido[2,3-d]pyrimidin-7(8H)-one;
6-(2,4-difluorophenyl)-8-ethyl-2-(ethylamino)-4-methylpyrido[2,3-d]pyrimidin-7(8H)-one;
6-(3-chloro-4-fluorophenyl)-8-ethyl-2-(ethylamino)-4-methylpyrido[2,3-d]pyrimidin-7(8H)-one;
8-ethyl-2-(ethylamino)-4-methyl-6-[4-(methyloxy)phenyl]pyrido[2,3-d]pyrimidin-7(8H)-one;
6-(2,4-dichlorophenyl)-8-ethyl-2-(ethylamino)-4-methylpyrido[2,3-d]pyrimidin-7(8H)-one;
6-(3,4-difluorophenyl)-8-ethyl-2-(ethylamino)-4-methylpyrido[2,3-d]pyrimidin-7(8H)-one;
8-ethyl-2-(ethylamino)-4-methyl-6-[2-(methyloxy)phenyl]pyrido[2,3-d]pyrimidin-7(8H)-one;
8-ethyl-2-(ethylamino)-4-methyl-6-[4-(phenyloxy)phenyl]pyrido[2,3-d]pyrimidin-7(8H)-one;
6-[2,4-bis(methyloxy)phenyl]-8-ethyl-2-(ethylamino)-4-methylpyrido[2,3-d]pyrimidin-7(8H)-one;
8-ethyl-2-(ethylamino)-6-(3-fluorophenyl)-4-methylpyrido[2,3-d]pyrimidin-7(8H)-one;
8-ethyl-2-(ethylamino)-6-(2-fluorophenyl)-4-methylpyrido[2,3-d]pyrimidin-7(8H)-one;
8-ethyl-2-(ethylamino)-4-methyl-6-[3-(trifluoromethyl)phenyl]pyrido[2,3-d]pyrimidin-7(8H)-one;
8-ethyl-2-(ethylamino)-6-(4-fluorophenyl)-4-methylpyrido[2,3-d]pyrimidin-7(8H)-one;
8-ethyl-2-(ethylamino)-4-methyl-6-(2-thienyl)pyrido[2,3-d]pyrimidin-7(8H)-one;
8-ethyl-2-(ethylamino)-4-methyl-6-[3-(methyloxy)phenyl]pyrido[2,3-d]pyrimidin-7(8H)-one;
6-(3-chlorophenyl)-8-ethyl-2-(ethylamino)-4-methylpyrido[2,3-d]pyrimidin-7(8H)-one;
6-(4-chlorophenyl)-8-ethyl-2-(ethylamino)-4-methylpyrido[2,3-d]pyrimidin-7(8H)-one;
8-ethyl-2-(ethylamino)-4-methyl-6-(3-thienyl)pyrido[2,3-d]pyrimidin-7(8H)-one;
8-ethyl-2-(ethylamino)-4-methyl-6-(4-methyl-2-thienyl)pyrido[2,3-d]pyrimidin-7(8H)-one;
8-ethyl-2-(ethylamino)-4-methyl-6-(4-methyl-3-thienyl)pyrido[2,3-d]pyrimidin-7(8H)-one;
1,1-dimethylethyl 2-[8-ethyl-2-(ethylamino)-4-methyl-7-oxo-7,8-dihydropyrido[2,3-d]pyrimidin-6-yl]-1H-pyrrole-1-carboxylate;
8-ethyl-2-(ethylamino)-4-methyl-6-(1H-pyrrol-2-yl)pyrido[2,3-d]pyrimidin-7(8H)-one;
6-(5-chloro-2-thienyl)-8-ethyl-2-(ethylamino)-4-methylpyrido[2,3-d]pyrimidin-7(8H)-O-one;
8-ethyl-2-(ethylamino)-4-methyl-6-pyrimidin-5-ylpyrido[2,3-d]pyrimidin-7(8H)-one;
8-ethyl-2-(ethylamino)-6-(3-fluoropyridin-4-yl)-4-methylpyrido[2,3-d]pyrimidin-7(8H)-one;
8-ethyl-2-(ethylamino)-6-furan-3-yl-4-methylpyrido[2,3-d]pyrimidin-7(8H)-one;
8-ethyl-2-(ethylamino)-4-methyl-6-[1-(phenylmethyl)-1H-pyrazol-4-yl]pyrido[2,3-d]pyrimidin-7(8H)-one;
2-(ethylamino)-4-methyl-8-(1-methylethyl)-6-(2-thienyl)pyrido[2,3-d]pyrimidin-7(8H)-one;
8-ethyl-2-(ethylamino)-6-(1H-indol-6-yl)-4-methylpyrido[2,3-d]pyrimidin-7(8H)-one;
8-ethyl-2-(ethylamino)-4-methyl-6-(5-phenyl-2-thienyl)pyrido[2,3-d]pyrimidin-7(8H)-one;
2-(ethylamino)-6-furan-3-yl-4-methyl-8-(1-methylethyl)pyrido[2,3-d]pyrimidin-7(8H)-one;
8-ethyl-2-(ethylamino)-4-methyl-6-(1H-pyrazol-5-yl)pyrido[2,3-d]pyrimidin-7(8H)-one;
8-cyclohexyl-2-(ethylamino)-4-methyl-6-(2-thienyl)pyrido[2,3-d]pyrimidin-7(8H)-one;
8-ethyl-2-(ethylamino)-4-methyl-6-(1,3-thiazol-2-yl)pyrido[2,3-d]pyrimidin-7(8H)-one;
8-cyclopentyl-2-(ethylamino)-4-methyl-6-(1H-pyrazol-3-yl)pyrido[2,3-d]pyrimidin-7 (8H)-one;
2-(ethylamino)-4-methyl-8-(1-methylethyl)-6-(1H-pyrazol-5-yl)pyrido[2,3-d]pyrimidin-7(8H)-one;
8-ethyl-2-(ethylamino)-4-methyl-6-(1H-pyrazol-1-yl)pyrido[2,3-d]pyrimidin-7(8H)-one;
2-(ethylamino)-4-methyl-8-(1-methylethyl)-6-(1H-pyrazol-1-yl)pyrido[2,3-d]pyrimidin-7(8H)-one;
8-cyclopentyl-2-(ethylamino)-4-methyl-6-(1H-pyrazol-1-yl)pyrido[2,3-d]pyrimidin-7(8H)-one;

8-ethyl-4-methyl-6-(1H-pyrazol-5-yl)-2-[(2,2,2-trifluoro-ethyl)amino]pyrido[2,3d]pyrimidin-7(8H)-one;
2-amino-8-ethyl-4-methyl-6-(1H-pyrazol-5-yl)pyrido[2,3-d]pyrimidin-7(8H)-one;
2-(ethylamino)-4-methyl-6-(1H-pyrazol-3-yl)pyrido[2,3-d]pyrimidin-7(8H)-one;
8-ethyl-4-methyl-2-(methylamino)-6-(1H-pyrazol-5-yl)pyrido[2,3-d]pyrimidin-7(8H)-one;
2-amino-8-cyclopentyl-4-methyl-6-(1H-pyrazol-3-yl)pyrido[2,3-d]pyrimidin-7(8H)-one;
8-ethyl-2-[(2-fluoroethyl)amino]-4-methyl-6-(1H-pyrazol-5-yl)pyrido[2,3-d]pyrimidin-7(8H)-one;
2-amino-4-methyl-8-(1-methylethyl)-6-(1H-pyrazol-3-yl)pyrido[2,3-d]pyrimidin-7(8H)-one;
2-amino-4-methyl-8-(phenylmethyl)-6-(1H-pyrazol-3-yl)pyrido[2,3-d]pyrimidin-7(8H)-one;
2-amino-8-ethyl-4-methyl-6-(4-methyl-3-thienyl)pyrido[2,3-d]pyrimidin-7(8H)-one;
2-amino-8-ethyl-4-methyl-6-(2-thienyl)pyrido[2,3-c]pyrimidin-7(8H)-one;
2-amino-8-ethyl-6-(4-fluorophenyl)-4-methylpyrido[2,3-d]pyrimidin-7(8H)-one;
2-amino-8-ethyl-6-(3-fluorophenyl)-4-methylpyrido[2,3-d]pyrimidin-7(8H)-one;
2-amino-8-ethyl-6-(2-fluorophenyl)-4-methylpyrido[2,3-d]pyrimidin-7(8H)-one;
2-amino-8-ethyl-4-methyl-6-(3-thienyl)pyrido[2,3-d]pyrimidin-7(8H)-one;
2-amino-8-ethyl-6-furan-3-yl-4-methylpyrido[2,3-d]pyrimidin-7(8H)-one;
2-amino-8-ethyl-4-methyl-6-phenylpyrido[2,3-d]pyrimidin-7(8H)-one;
2-amino-8-ethyl-4-methyl-6-[4-(methyloxy)phenyl]pyrido[2,3-c]pyrimidin-7(81)-one;
2-amino-6-(4-chlorophenyl)-8-ethyl-4-methylpyrido[2,3-d]pyrimidin-7(8H)-one;
2-amino-6-(3-chlorophenyl)-8-ethyl-4-methylpyrido[2,3-d]pyrimidin-7(8H)-one;
2-amino-8-ethyl-6-isoxazol-4-yl-4-methylpyrido[2,3-d]pyrimidin-7(8H)-one;
2-amino-8-ethyl-6-furan-2-yl-4-methylpyrido[2,3-c]pyrimidin-7(8H)-one;
2-amino-6-(2,4-dichlorophenyl)-8-ethyl-4-methylpyrido[2,3-a]pyrimidin-7(8H)-one;
5-(2-amino-8-ethyl-4-methyl-7-oxo-7,8-dihydropyrido[2,3-d]pyrimidin-6-yl)thiophene-2-carbonitrile;
2-amino-8-ethyl-4-methyl-6-pyrimidin-5-ylpyrido[2,3-d]pyrimidin-7(8H)-one;
2-amino-8-ethyl-6-(1H-imidazol-5-yl)-4-methylpyrido[2,3-d]pyrimidin-7(81)-one;
2-amino-8-ethyl-4-methyl-6-(1H-1,2,3-triazol-5-yl)pyrido[2,3-d]pyrimidin-7(8H)-one;
2-amino-8-ethyl-4-methyl-6-(1H-pyrazol-4-yl)pyrido[2,3-d]pyrimidin-7(8H)-one;
2-amino-8-ethyl-4-methyl-6-(1,3-thiazol-2-yl)pyrido[2,3-d]pyrimidin-7(8H)-one;
2-amino-8-ethyl-4-methyl-6-(1H-tetrazol-5-yl)pyrido[2,3-d]pyrimidin-7(8H)-one;
2-amino-8-ethyl-4-methyl-6-(1-methyl-1H-pyrrol-2-yl)pyrido[2,3-d]pyrimidin-7(8H)-one;
2-amino-4,8-diethyl-6-(1H-pyrazol-5-yl)pyrido[2,3-d]pyrimidin-7(8H)-one; and
2-amino-8-cyclopentyl-4-methyl-6-(1,3-thiazol-5-yl)pyrido[2,3-d]pyrimidin-7(8H)-one.

34. A pharmaceutical composition which comprises a compound of claim 1 or a pharmaceutically acceptable salt thereof and a pharmaceutically acceptable carrier, excipient, or diluent.

35. The Compound of claim 1 selected from
8-ethyl-2-(ethylamino)-4-methyl-6-(2-thienyl)pyrido[2,3-d]pyrimidin-7(8H)-one;
8-ethyl-2-(ethylamino)-4-methyl-6-(3-thienyl)pyrido[2,3-d]pyrimidin-7(8H)-one;
8-ethyl-2-(ethylamino)-4-methyl-6-(4-methyl-2-thienyl)pyrido[2,3-d]pyrimidin-7(8H)-one;
8-ethyl-2-(ethylamino)-4-methyl-6-(4-methyl-3-thienyl)pyrido[2,3-d]pyrimidin-7(8H)-one;
1,1-dimethylethyl 2-[8-ethyl-2-(ethylamino)-4-methyl-7-oxo-7,8-dihydropyrido[2,3-d]pyrimidin-6-yl]-1H-pyrrole-1-carboxylate
8-ethyl-2-(ethylamino)-4-methyl-6-(1H-pyrrol-2-yl)pyrido[2,3-d]pyrimidin-7(8H)-one;
6-(5-chloro-2-thienyl)-8-ethyl-2-(ethylamino)-4-methylpyrido[2,3-d]pyrimidin-7(8H)-one;
8-ethyl-2-(ethylamino)-4-methyl-6-pyrimidin-5-ylpyrido[2,3-d]pyrimidin-7(8H)-one;
8-ethyl-2-(ethylamino)-6-(3-fluoropyridin-4-yl)-4-methylpyrido[2,3-d]pyrimidin-7(8H)-one;
8-ethyl-2-(ethylamino)-6-furan-3-yl-4-methylpyrido[2,3-d]pyrimidin-7(8H)-one;
2-(ethylamino)-4-methyl-8-(1-methylethyl)-6-(2-thienyl)pyrido[2,3-d]pyrimidin-7(8H)-one;
8-ethyl-2-(ethylamino)-6-(1H-indol-6-yl)-4-methylpyrido[2,3-d]pyrimidin-7(8H)-one;
8-ethyl-2-(ethylamino)-4-methyl-6-(5-phenyl-2-thienyl)pyrido[2,3-d]pyrimidin-7(8H)-one;
2-(ethylamino)-6-furan-3-yl-4-methyl-8-(1-methylethyl)pyrido[2,3-d]pyrimidin-7(8H)-one;
8-ethyl-2-(ethylamino)-4-methyl-6-(1H-pyrazol-5-yl)pyrido[2,3-d]pyrimidin-7(8H)-one;
8-cyclohexyl-2-(ethylamino)-4-methyl-6-(2-thienyl)pyrido[2,3-d]pyrimidin-7(8H)-one;
8-ethyl-2-(ethylamino)-4-methyl-6-(1,3-thiazol-2-yl)pyrido[2,3-d]pyrimidin-7(8H)-one;
8-cyclopentyl-2-(ethylamino)-4-methyl-6-(1H-pyrazol-3-yl)pyrido[2,3-d]pyrimidin-7(8H)-one;
2-(ethylamino)-4-methyl-8-(1-methylethyl)-6-(1H-pyrazol-5-yl)pyrido[2,3-d]pyrimidin-7(8H)-one;
8-ethyl-2-(ethylamino)-4-methyl-6-(1H-pyrazol-1-yl)pyrido[2,3-d]pyrimidin-7(8H)-one;
2-(ethylamino)-4-methyl-8-(1-methylethyl)-6-(1H-pyrazol-1-yl)pyrido[2,3-d]pyrimidin-7(8H)-one;
8-cyclopentyl-2-(ethylamino)-4-methyl-6-(1H-pyrazol-1-yl)pyrido[2,3-d]pyrimidin-7(8H)-one;
8-ethyl-4-methyl-6-(1H-pyrazol-5-yl)-2-[(2,2,2-trifluoroethyl)amino]pyrido[2,3-d]pyrimidin-7(8H)-one;
2-(ethylamino)-4-methyl-6-(1H-pyrazol-3-yl)pyrido[2,3-d]pyrimidin-7(8H)-one;
8-ethyl-4-methyl-2-(methylamino)-6-(1H-pyrazol-5-yl)pyrido[2,3-d]pyrimidin-7(8H)-one; and
8-ethyl-2-[(2-fluoroethyl)amino]-4-methyl-6-(1H-pyrazol-5-yl)pyrido[2,3-c]pyrimidin-7(8H)-one;
or a pharmaceutically acceptable salt thereof.

36. The Compound of claim 1 selected from
2-amino-8-ethyl-4-methyl-6-(1H-pyrazol-5-yl)pyrido[2,3-d]pyrimidin-7(8H)-one;
2-amino-8-cyclopentyl-4-methyl-6-(1H-pyrazol-3-yl)pyrido[2,3-d]pyrimidin-7(8H)-one;
2-amino-4-methyl-8-(1-methylethyl)-6-(1H-pyrazol-3-yl)pyrido[2,3-d]pyrimidin-7(8H)-one;

2-amino-4-methyl-8-(phenylmethyl)-6-(1H-pyrazol-3-yl)pyrido[2,3-d]pyrimidin-7(8H)-one;
2-amino-8-ethyl-4-methyl-6-(4-methyl-3-thienyl)pyrido[2,3-d]pyrimidin-7(8H)-one;
2-amino-8-ethyl-4-methyl-6-(2-thienyl)pyrido[2,3-d]pyrimidin-7(8H)-one;
2-amino-8-ethyl-4-methyl-6-(3-thienyl)pyrido[2,3-d]-pyrimidin-7(8H)-one;
2-amino-8-ethyl-6-furan-3-yl-4-methylpyrido[2,3-d]pyrimidin-7(8H)-one;
2-amino-8-ethyl-4-methyl-6-phenylpyrido[2,3-d]pyrimidin-7(8H)-one;
2-amino-8-ethyl-6-isoxazol-4-yl-4-methylpyrido[2,3-d]pyrimidin-7(8H)-one;
2-amino-8-ethyl-6-furan-2-yl-4-methylpyrido[2,3-d]pyrimidin-7(8H)-one;
5-(2-amino-8-ethyl-4-methyl-7-oxo-7,8-dihydropyrido[2,3-d]pyrimidin-6-yl)thiophene-2-carbonitrile;
2-amino-8-ethyl-4-methyl-6-pyrimidin-5-ylpyrido[2,3-d]pyrimidin-7(8H)-one;
2-amino-8-ethyl-6-(1H-imidazol-5-yl)-4-methylpyrido[2,3-d]pyrimidin-7(8H)-one;
2-amino-8-ethyl-4-methyl-6-(1H-1,2,3-triazol-5-yl)pyrido[2,3-d]pyrimidin-7(8H)-one;
2-amino-8-ethyl-4-methyl-6-(1H-pyrazol-4-yl)pyrido[2,3-d]pyrimidin-7(8H)-one;
2-amino-8-ethyl-4-methyl-6-(1,3-thiazol-2-yl)pyrido[2,3-d]pyrimidin-7(8H)-one;
2-amino-8-ethyl-4-methyl-6-(1H-tetrazol-5-yl)pyrido[2,3-d]pyrimidin-7(8H)-one;
2-amino-8-ethyl-4-methyl-6-(1-methyl-1H-pyrrol-2-yl)pyrido[2,3-d]pyrimidin-7(8H)-one;
2-amino-4,8-diethyl-6-(1H-pyrazol-5-yl)pyrido[2,3-d]pyrimidin-7(8H)-one; and
2-amino-8-cyclopentyl-4-methyl-6-(1,3-thiazol-5-yl)pyrido[2,3-d]pyrimidin-7(8H)-one;
or a pharmaceutically acceptable salt thereof.

37. The Compound of claim 1, wherein the compound is 2-amino-8-ethyl-4-methyl-6-(1H-pyrazol-5-yl)pyrido[2,3-d]pyrimidin-7(8H)-one or a pharmaceutically acceptable salt thereof.

* * * * *